US011266688B2

(12) United States Patent
Fan et al.

(10) Patent No.: US 11,266,688 B2
(45) Date of Patent: Mar. 8, 2022

(54) SINGLE-CHAIN ANTIBODY SPECIFICALLY BINDING MG7, HIGHLY GLYCOSYLATED CEA AND USE THEREOF IN DETECTION AND THERAPY

(71) Applicants: THE FOURTH MILITARY MEDICAL UNIVERSITY, Shaanxi (CN); SHANGHAI GENBASE BIOTECH CO., LTD., Shanghai (CN)

(72) Inventors: Daiming Fan, Shaanxi (CN); Yongzhan Nie, Shaanxi (CN); Kaichun Wu, Shaanxi (CN); Yueqiong Cao, Shanghai (CN); Jijun Yuan, Shanghai (CN); Xuejun Yu, Shanghai (CN)

(73) Assignees: THE FOURTH MILITARY MEDICAL UNIVERSITY XI'AN, Shaanxi (CN); SHANGHAI GENBASE BIOTECH CO., LTD., Shanghai (CN)

( * ) Notice: Subject to any disclaimer, the term of this patent is extended or adjusted under 35 U.S.C. 154(b) by 415 days.

(21) Appl. No.: 16/321,529

(22) PCT Filed: Jul. 27, 2017

(86) PCT No.: PCT/CN2017/094755
§ 371 (c)(1),
(2) Date: Jan. 29, 2019

(87) PCT Pub. No.: WO2018/019275
PCT Pub. Date: Feb. 1, 2018

(65) Prior Publication Data

US 2019/0167721 A1 Jun. 6, 2019

(30) Foreign Application Priority Data

Jul. 29, 2016 (CN) ........................ 201610614701.3

(51) Int. Cl.

| | |
|---|---|
| ***C07K 16/30*** | (2006.01) |
| ***A61P 35/00*** | (2006.01) |
| ***C07K 19/00*** | (2006.01) |
| ***A61K 35/17*** | (2015.01) |
| ***C12N 15/62*** | (2006.01) |
| ***G01N 33/574*** | (2006.01) |
| ***C12N 5/10*** | (2006.01) |
| ***C07K 16/40*** | (2006.01) |

(52) U.S. Cl.
CPC .............. *A61K 35/17* (2013.01); *A61P 35/00* (2018.01); *C07K 16/30* (2013.01); *C07K 16/40* (2013.01); *C07K 19/00* (2013.01); *C12N 5/10* (2013.01); *C12N 15/62* (2013.01); *G01N 33/574* (2013.01)

(58) Field of Classification Search
CPC ............ A61K 39/001182; A61K 35/17; C07K 14/7051; C07K 14/70517; C07K 14/70521; C07K 14/70575; C07K 14/70596; C07K 16/40; C07K 16/30; C07K 16/3007; C12N 15/62; G01N 33/574; A61P 35/00
See application file for complete search history.

(56) References Cited

U.S. PATENT DOCUMENTS

| | | | |
|---|---|---|---|
| 5,872,215 A | 2/1999 | Osbourne et al. | |
| 7,674,605 B2 * | 3/2010 | Lin .................. | G01N 33/57492 435/69.1 |

FOREIGN PATENT DOCUMENTS

| | | |
|---|---|---|
| CN | 1878562 A | 12/2006 |
| CN | 102741293 A | 10/2012 |
| CN | 104628859 A | 5/2015 |
| CN | 104829733 A | 8/2015 |
| CN | 104910279 A | 9/2015 |
| CN | 104910279 A | 9/2015 |
| CN | 105330750 A | 2/2016 |
| EP | 1505076 | 2/2005 |
| EP | 3034514 | 6/2016 |
| WO | 2007071422 | 6/2007 |
| WO | 2007071426 | 6/2007 |
| WO | 2007146172 | 12/2007 |
| WO | 2011163401 | 12/2011 |
| WO | 2015153685 | 10/2015 |
| WO | 2015164594 A1 | 10/2015 |

OTHER PUBLICATIONS

Malia et al., Proteins 2016; 84;427-434 (Year: 2016).*
De Genst et al., Developmental and Comparative Immunology, 2006, 30:187-198 (Year: 2006).*
Ward et al. Nature, 1989, 341:544-546 (Year: 1989).*
Barthelemy et al. Journal of Biological Chemistry, 2008, 283:3639-3654 (Year: 2008).*
Choi & Deane, Molecular BioSystems, 2011, 7:3327-3334 (Year: 2011).*
Griffiths et al. EMBO Journal, 1993, 12:725-734 (Year: 1993).*
Klimka et al., British Journal of Cancer, 2000, 83:252-260 (Year: 2000).*
Beiboer et al. Journal of Molecular Biology, 2000, 296:833-849 (Year: 2000).*
Hammarstrom, S., Seminars in Cancer Biology, vol. 9, 1999: pp. 67-81 (Year: 1999).*
Shirasu et al. Anticancer Research, 2010, 30: 2731-2738 (Year: 2010).*

(Continued)

*Primary Examiner* — Julie Wu
*Assistant Examiner* — Cheom-Gil Cheong
(74) *Attorney, Agent, or Firm* — Robin L. Teskin; Baker, Donelson, Bearman, Caldwell & Berkowitz PC

(57) ABSTRACT

The present invention provides a glycosylated CEA-specific single-chain antibody, and a chimeric antigen receptor (CAR) targeting a glycosylated CEA, which can be used in manufacture of an agent or a medicament for diagnosis or treatment of a tumor overexpressing glycosylated CEA.

16 Claims, 8 Drawing Sheets

Specification includes a Sequence Listing.

(56) References Cited

OTHER PUBLICATIONS

Dotti, et al., 2014, Immunological Reviews, 257(1), 107-126 (Year: 2014).*
Gyobu et al. Cancer Research, 2004, 64(4): 1490-1495 (Year: 2004).*
Hornbach et al. Journal of Immunology 2001, 167(11): 6123-6131 (Year: 2001).*
Int'l Search Report of Int'l Appl. No. WO 2007/14672 A3 published Mar. 19, 2008.
Abstract of published Int'l Appl. No. WO 2007/14672 A8 published Dec. 21, 2007.
Osbourn et al. "Isolation of a panel of human anti-CEA single chain Fv from a large phage display library." Tumor Targeting. 1999;4:150-7.
Blat et al. "Suppression of murine colitis and its associated cancer by carcinoembryonic antigen-specific regulatory T cells." Molecular Therapy. May 1, 2014;22(5):1018-28.
Chmielewski et al. "IL-12 release by engineered T cells expressing chimeric antigen receptors can effectively Muster an antigen-independent macrophage response on tumor cells that have shut down tumor antigen expression." Cancer research. Sep. 1, 2011;71(17):5697-706.
Dotti et al. "Design and development of therapies using chimeric antigen receptor-expressing T cells." Immunological reviews. Jan. 2014;257(1):107-26.
"16C3 antibody light chain protein, SEQ:76." XP002797325, Feb. 16, 2012, retrieved from EBI accession No. GSP: AZR20053.
"Humanized 16C3 antibody light chain (cdr16C3) protein, SEQ:86." XP002797324, Feb. 16, 2012, retrieved from EBI accession No. GSP:AZR20063.
Int'l Search Report of Int'l Appl. No. WO 2011/163401 A3 published Mar. 13, 2012.
"Anti-pertussis toxin humanized antibody (sdr11E6) VH region, SEQ 16", Dec. 3, 2015, retrieved from EBI accession No. GSP:BCF33096.
Int'l Search Report of Int'l Appl. No. WO 2007/071422 A3 published Jul. 30, 2007.

* cited by examiner

SEQUENCE LISTING

```
<160> NUMBER OF SEQ ID NOS: 181

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Gly Phe Thr Phe Ser Arg Tyr
1               5


<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Ser Asn Ser Gly Ser Tyr
1               5
```

<210> SEQ ID NO 3
<211> LENGTH: 3
<212> TYPE: PRT
<213> ORGANISM: Artificial Sequence
<220> FEATURE:
<223> OTHER INFORMATION: Synthetic

<400> SEQUENCE: 3

Gly Ser Pro
1

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Gly Ala Ser Glu Asn Ile Tyr Gly Ala Leu Asn
1 5 10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gly Ala Thr Lys Leu Ala Asp
1 5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Asn Val Leu Ser Lys Pro Tyr Ala
1 5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Gly Tyr Thr Phe Ser Thr Tyr
1 5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Tyr Pro Gly Asp Gly Asp
1 5

```
<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Gly Gly Leu Tyr Tyr Gly Tyr Asp Ile Ala Tyr
1               5                   10


<210> SEQ ID NO 10
<211> LENGTH: 16
<212> TYPE: PRT
<213> ORGANISM: Artificial Sequence
<220> FEATURE:
<223> OTHER INFORMATION: Synthetic

<400> SEQUENCE: 10

Arg Ser Ser Gln Ser Ile Val His Ser Asn Gly Asn Thr Tyr Leu Glu
1               5                   10                  15


<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Lys Val Ser Asn Arg Phe Ser
1               5


<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Phe Gln Gly Ser His Val Pro Phe Thr
1               5


<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Gly Phe Thr Phe Thr Asp Tyr
1               5


<210> SEQ ID NO 14
<211> LENGTH: 8
<212> TYPE: PRT
<213> ORGANISM: Artificial Sequence
<220> FEATURE:
<223> OTHER INFORMATION: Synthetic

<400> SEQUENCE: 14

Arg Asn Lys Val Asn Gly Asp Thr
1               5
```

```
<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Gly Gly Leu Tyr Tyr Gly Tyr Asp Ile Ala Tyr
1               5                   10


<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Asp Lys Gly Ile Ala Tyr Tyr Phe Asp Tyr
1               5                   10


<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Gly Thr Ser Asn Leu Ala Ser
1               5


<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln Gln Trp Ser Ser Asn Leu Ser Thr
1               5


<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Gly Phe Ser Leu Thr Ser Tyr
1               5


<210> SEQ ID NO 20
<211> LENGTH: 5
<212> TYPE: PRT
<213> ORGANISM: Artificial Sequence
<220> FEATURE:
<223> OTHER INFORMATION: Synthetic

<400> SEQUENCE: 20

Trp Thr Gly Gly Gly
1               5


<210> SEQ ID NO 21
```

<211> LENGTH: 7
<212> TYPE: PRT
<213> ORGANISM: Artificial Sequence
<220> FEATURE:
<223> OTHER INFORMATION: Synthetic

<400> SEQUENCE: 21

Gly Val Tyr Tyr Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Lys Ala Ser Gln Asp Val Thr Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Trp Ala Ser Thr Arg His Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Gln Gln Tyr Tyr Arg Thr Pro Arg Thr
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Gly Tyr Thr Phe Asn Asp Tyr Asn Met Asp Tyr
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Asn Pro Asn Tyr Asp Ser
1               5

<210> SEQ ID NO 27
<211> LENGTH: 13

```
<212> TYPE: PRT
<213> ORGANISM: Artificial Sequence
<220> FEATURE:
<223> OTHER INFORMATION: Synthetic

<400> SEQUENCE: 27

Arg Asp Tyr Asp Gly Arg Arg Gly Ala Trp Phe Ser Tyr
1               5                   10


<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Thr Ala Ser Ser Ser Val Ser Tyr Met Tyr Trp Tyr
1               5                   10


<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

Leu Thr Ser Asn Leu Ala Ser
1               5


<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Gln Gln Trp Asp Ser Asn Pro Leu Thr
1               5


<210> SEQ ID NO 31
<211> LENGTH: 116
<212> TYPE: PRT
<213> ORGANISM: Artificial Sequence
<220> FEATURE:
<223> OTHER INFORMATION: Synthetic

<400> SEQUENCE: 31

Gly Val Gln Cys Asp Val Lys Leu Val Glu Ser Gly Gly Gly Leu Val
1               5                   10                  15

Lys Pro Gly Gly Ser Leu Lys Leu Ser Cys Ala Ala Ser Gly Phe Thr
            20                  25                  30

Phe Ser Arg Tyr Thr Met Ser Trp Val Arg Gln Thr Pro Glu Lys Arg
        35                  40                  45

Leu Glu Trp Val Ala Thr Ile Ser Asn Ser Gly Ser Tyr Thr Tyr Tyr
    50                  55                  60

Arg Asp Ser Val Lys Gly Arg Phe Thr Ile Ser Arg Asp Asn Ala Lys
65                  70                  75                  80

Asn Thr Leu Tyr Leu Gln Met Ser Ser Leu Lys Ser Glu Asp Thr Ala
                85                  90                  95

Met Tyr Tyr Cys Thr Arg Gly Ser Pro Trp Gly Gln Gly Thr Leu Val
            100                 105                 110
```

```
Thr Val Ser Ala
        115


<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Asp Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Lys Leu Ala Asp Gly Met Ser Ser Arg Phe Ser Gly
    50                  55                  60

Ser Gly Ser Asn Arg Gln Tyr Ser Leu Lys Ile Ser Ser Leu His Pro
65                  70                  75                  80

Asp Asp Val Ala Thr Tyr Tyr Cys Gln Asn Val Leu Ser Lys Pro Tyr
                85                  90                  95

Ala Phe Gly Gly Gly Thr Lys Leu Glu Ile Lys
            100                 105


<210> SEQ ID NO 33
<211> LENGTH: 120
<212> TYPE: PRT
<213> ORGANISM: Artificial Sequence
<220> FEATURE:
<223> OTHER INFORMATION: Synthetic

<400> SEQUENCE: 33

Glu Val Lys Leu Gln Gln Ser Gly Ala Asp Leu Ala Thr Pro Gly Ala
1               5                   10                  15

Ser Val Lys Leu Ser Cys Lys Ala Ser Gly Tyr Thr Phe Ser Thr Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala His
65                  70                  75                  80

Met Gln Leu Ser Ser Leu Ala Ser Glu Asp Ser Ala Val Tyr Tyr Cys
                85                  90                  95

Ala Arg Gly Gly Leu Tyr Tyr Gly Tyr Asp Ile Ala Tyr Trp Gly Gln
            100                 105                 110

Gly Thr Leu Val Thr Val Ser Ala
        115                 120


<210> SEQ ID NO 34
<211> LENGTH: 112
<212> TYPE: PRT
<213> ORGANISM: Artificial Sequence
<220> FEATURE:
<223> OTHER INFORMATION: Synthetic

<400> SEQUENCE: 34
```

Asp Ile Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Pro Leu Ile Lys Lys Val Ser Asn Arg Phe Ser Gly Val Pro
50 55 60

Asp Arg Phe Ser Gly Ser Gly Ser Gly Thr Glu Phe Thr Leu Lys Ile
65 70 75 80

Ser Arg Val Glu Ala Glu Asp Leu Gly Val Tyr Tyr Cys Phe Gln Gly
85 90 95

Ser His Val Pro Phe Thr Phe Gly Ser Gly Thr Lys Leu Glu Ile Lys
100 105 110

<210> SEQ ID NO 35
<211> LENGTH: 121
<212> TYPE: PRT
<213> ORGANISM: Artificial Sequence
<220> FEATURE:
<223> OTHER INFORMATION: Synthetic

<400> SEQUENCE: 35

Glu Val Lys Leu Val Glu Ser Gly Gly Gly Leu Val Gln Pro Gly Gly
1 5 10 15

Ser Leu Arg Leu Ser Cys Ser Ile Ser Gly Phe Thr Phe Thr Asp Tyr
20 25 30

Tyr Met Asn Trp Val Arg Gln Ser Pro Gly Lys Ala Leu Glu Trp Leu
35 40 45

Gly Phe Ile Arg Asn Lys Val Asn Gly Asp Thr Thr Glu Tyr Ser Ala
50 55 60

Ser Val Lys Gly Arg Phe Thr Ile Ser Arg Asp Ile Ser Gln Ser Ile
65 70 75 80

Leu Tyr Leu Gln Met Asn Thr Leu Arg Thr Glu Asp Ser Ala Thr Tyr
85 90 95

Tyr Cys Ala Arg Asp Lys Gly Ile Ala Tyr Tyr Phe Asp Tyr Trp Gly
100 105 110

Gln Gly Thr Thr Leu Thr Val Ser Ser
115 120

<210> SEQ ID NO 36
<211> LENGTH: 106
<212> TYPE: PRT
<213> ORGANISM: Artificial Sequence
<220> FEATURE:
<223> OTHER INFORMATION: Synthetic

<400> SEQUENCE: 36

Gln Ile Val Leu Ser Gln Ser Pro Ala Ile Leu Phe Ala Ser Pro Gly
1 5 10 15

Glu Lys Val Thr Met Thr Cys Arg Ala Ser Ser Ser Val Ser Tyr Ile
20 25 30

His Trp Tyr Gln Gln Lys Pro Gly Ser Ser Pro Lys Pro Trp Ile His
35 40 45

Gly Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

```
Asp Ala Ala Thr Tyr Tyr Cys Gln Gln Trp Ser Ser Asn Leu Ser Thr
                85                  90                  95

Phe Gly Gly Gly Thr Lys Leu Glu Ile Lys
            100                 105


<210> SEQ ID NO 37
<211> LENGTH: 115
<212> TYPE: PRT
<213> ORGANISM: Artificial Sequence
<220> FEATURE:
<223> OTHER INFORMATION: Synthetic

<400> SEQUENCE: 37

Gln Val Gln Leu Lys Glu Ser Gly Pro Gly Leu Val Ala Pro Ser Gln
1               5                   10                  15

Asn Leu Ser Ile Thr Cys Thr Val Ser Gly Phe Ser Leu Thr Ser Tyr
            20                  25                  30

Ala Ile Asn Trp Val Arg Gln Pro Pro Gly Lys Gly Leu Glu Trp Leu
        35                  40                  45

Gly Ile Ile Trp Thr Gly Gly Gly Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Ser Gly Val Tyr Tyr Phe Asp Tyr Trp Gly Leu Gly Thr Thr Leu Thr
            100                 105                 110

Val Ser Ser
        115


<210> SEQ ID NO 38
<211> LENGTH: 107
<212> TYPE: PRT
<213> ORGANISM: Artificial Sequence
<220> FEATURE:
<223> OTHER INFORMATION: Synthetic

<400> SEQUENCE: 38

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Val Leu Ile
        35                  40                  45

Phe Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln Tyr Tyr Arg Thr Pro Arg
                85                  90                  95

Thr Phe Gly Gly Gly Thr Lys Leu Glu Ile Lys
            100                 105


<210> SEQ ID NO 39
<211> LENGTH: 122
<212> TYPE: PRT
<213> ORGANISM: Artificial Sequence
<220> FEATURE:
<223> OTHER INFORMATION: Synthetic
```

```
<400> SEQUENCE: 39

Glu Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Asn Asp Tyr
            20                  25                  30

Asn Met Asp Tyr Leu Lys Gln Ser His Gly Lys Ser Leu Glu Trp Ile
        35                  40                  45

Gly Asp Ile Asn Pro Asn Tyr Asp Ser Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Asp Tyr Asp Gly Arg Arg Gly Ala Trp Phe Ser Tyr Trp
            100                 105                 110

Gly Gln Gly Thr Leu Val Thr Val Ser Ala
        115                 120


<210> SEQ ID NO 40
<211> LENGTH: 106
<212> TYPE: PRT
<213> ORGANISM: Artificial Sequence
<220> FEATURE:
<223> OTHER INFORMATION: Synthetic

<400> SEQUENCE: 40

Gln Ile Val Leu Thr Gln Ser Pro Ala Leu Met Ser Ala Ser Pro Gly
1               5                   10                  15

Glu Lys Val Thr Val Thr Cys Thr Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Thr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asp Ser Asn Pro Leu Thr
                85                  90                  95

Phe Gly Ala Gly Thr Lys Leu Glu Leu Lys
            100                 105


<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

Gly Gly Gly Gly Ser Gly Gly Gly Gly Ser Gly Gly Gly Gly Ser
1               5                   10                  15


<210> SEQ ID NO 42
<211> LENGTH: 348
<212> TYPE: DNA
<213> ORGANISM: Artificial Sequence
<220> FEATURE:
<223> OTHER INFORMATION: Synthetic
```

<400> SEQUENCE: 42
ggtgtccagt gtgacgtgaa gttggtggag tctgggggag gcttagtgaa gcctggaggg 60
tccctgaaac tctcctgtgc agcctctgga ttcactttca gtagatacac catgtcttgg 120
gttcgccaga ctccggagaa gaggctggag tgggtcgcaa ccattagtaa tagtggtagt 180
tatacctact atcgagacag tgtgaagggc cgattcacca tctccagaga caatgccaag 240
aacaccctgt acctgcaaat gagcagtctg aagtctgagg acacagccat gtattactgt 300
acaagggggt cgccctgggg ccaagggact ctggtcactg tctctgca 348

<210> SEQ ID NO 43
<211> LENGTH: 321
<212> TYPE: DNA
<213> ORGANISM: Artificial Sequence
<220> FEATURE:
<223> OTHER INFORMATION: Synthetic

<400> SEQUENCE: 43
gacatccaga tgactcagtc tccagattca ctgtctgcat ctgtgggaga aactgtcacc 60
atcacatgtg gagcaagtga gaacatttac ggtgctttaa attggtatca gcggaaacag 120
ggaaaatctc ctcagctcct gatctatggt gcaaccaagt tggcagatgg catgtcatcg 180
aggttcagtg gcagtggatc taatagacag tattctctca agatcagtag cctgcatcct 240
gacgatgttg caacgtatta ctgtcaaaat gtgttaagta agccgtacgc gttcggaggg 300
gggaccaaac tggaaataaa a 321

<210> SEQ ID NO 44
<211> LENGTH: 360
<212> TYPE: DNA
<213> ORGANISM: Artificial Sequence
<220> FEATURE:
<223> OTHER INFORMATION: Synthetic

<400> SEQUENCE: 44
gaggtgaagc tgcagcaatc aggggctgac ctggcaacac ctggggcttc agtgaagttg 60
tcctgcaagg cttctggcta tacctttagt acctactgga tgcagtgggt aaaacagagg 120
cctggacagg gtctggaatg gattgggact atttatcctg gagatggtga tactaggtac 180
actcagaagt tcaagggcaa ggccacattg actgcagata aatcctccag tacagcccac 240
atgcaactca gcagcttggc atctgaggac tctgcggtct attattgtgc aagaggggga 300
ctctattatg gttacgacat tgcttactgg ggccaaggga ctctggtcac tgtctctgca 360

<210> SEQ ID NO 45
<211> LENGTH: 336
<212> TYPE: DNA
<213> ORGANISM: Artificial Sequence
<220> FEATURE:
<223> OTHER INFORMATION: Synthetic

<400> SEQUENCE: 45
gatattttga tgacccaaac tccactctcc ctgcctgtca gtcttggaga tcaagcctcc 60
atctcttgca gatctagtca gagcattgta catagtaatg gaaacaccta tttagaatgg 120
tacctgcaga aaccaggcca gtctccaaag cccctgataa agaaagtctc caaccgattt 180
tctggggtcc cagacaggtt cagtggcagt ggatcaggga cagaattcac actcaagatc 240
agcagagtgg aggctgagga tctgggagtt tattactgct ttcaaggttc acatgttcca 300
ttcacgttcg gctcggggac aaagttggaa ataaaa 336

<210> SEQ ID NO 46
<211> LENGTH: 363
<212> TYPE: DNA
<213> ORGANISM: Artificial Sequence
<220> FEATURE:
<223> OTHER INFORMATION: Synthetic

<400> SEQUENCE: 46
gaggtgaagc tggtggagtc tggaggaggc ttggtccagc cggggggtc tctgagactc 60 tcctgttcaa tttctggatt caccttcact gattactaca tgaactgggt ccgccagtct 120
ccaggaaagg cacttgagtg gttgggtttt attagaaaca aagttaatgg tgacacaaca 180
gaatatagtg catctgtgaa gggtcggttc accatctcca gagatatttc ccagagcatc 240
ctctatcttc aaatgaacac cctgagaact gaggacagtg ccacttatta ctgtgcgaga 300
gataagggaa tagcgtacta ctttgactat tggggccaag gcaccactct cacagtctcc 360
tca 363

<210> SEQ ID NO 47
<211> LENGTH: 318
<212> TYPE: DNA
<213> ORGANISM: Artificial Sequence
<220> FEATURE:
<223> OTHER INFORMATION: Synthetic

<400> SEQUENCE: 47
caaattgttc tctcccagtc tccagcaatc ctgtttgcat ctccagggga gaaggtcaca 60
atgacttgta gggccagctc aagtgtaagt tacattcact ggtaccagca gaagccagga 120
tcctccccca aaccctggat tcatggcaca tccaacctgg cttctggagt ccctgctcgc 180
ttcagtggca gtgggtctgg gacctcttac tctctcacaa tcagcagaat ggaggctgaa 240
gatgccgcca catattactg ccagcagtgg agtagtaatt tatccacgtt cggagggggg 300
accaagctgg aaataaaa 318

<210> SEQ ID NO 48
<211> LENGTH: 345
<212> TYPE: DNA
<213> ORGANISM: Artificial Sequence
<220> FEATURE:
<223> OTHER INFORMATION: Synthetic

<400> SEQUENCE: 48
caggtgcagc tgaaggagtc aggacctggc ctggtggcgc cctcacagaa cctgtccatc 60
acatgcactg tctctgggtt ctcattaacc agctatgcta taaactgggt tcgccagcca 120
ccaggaaagg gtctggagtg gcttggaata atatggactg gtggaggcac aaattataat 180
tcagctctca aatccagact gagcatcagc aaagacaact ccaagagtca agttttctta 240
aaaatgaaca gtctgcaaac tgatgacaca gccaggtact actgtgcctc gggggtgtac 300
tactttgact actggggcct aggcaccact ctcacagtct cctca 345

<210> SEQ ID NO 49
<211> LENGTH: 321
<212> TYPE: DNA
<213> ORGANISM: Artificial Sequence
<220> FEATURE:
<223> OTHER INFORMATION: Synthetic

<400> SEQUENCE: 49

-continued

```
gacattgtga tgacccagtc tcacaaattc atgtccacat cagtaggaga cagggtcagc     60

atcacctgca aggccagtca ggatgtgact actgctgtag cctggtatca acaaaaacca    120

gggcaatctc ctaaagtact gattttctgg gcatccaccc ggcacactgg agtccctgat    180

cgcttcacag gcagtggatc tgggacagat tatactctca ccatcagcag tgtgcaggct    240

gaagacctgg cactttatta ctgtcagcaa tattatagaa ctcctcggac gttcggtgga    300

ggcaccaaac tggaaatcaa a                                              321
```

<210> SEQ ID NO 50
<211> LENGTH: 366
<212> TYPE: DNA
<213> ORGANISM: Artificial Sequence
<220> FEATURE:
<223> OTHER INFORMATION: Synthetic

<400> SEQUENCE: 50

```
gaggtgaagc tgcaggaatc tggagctgag ctggtgaagc ctggggcttc agtgaagatc     60

tcctgcaagg cttctggcta cacattcaat gactacaaca tggactatct gaagcagagc    120

catggaaaga gccttgagtg gattggagat attaatccta actatgatag cactatctac    180

aaccagaagt tcaagggcaa ggccacattg actgtagaca agtcctccag cacagcctac    240

atggagctcc gcagcctgac atctgaggac tctgcagtct attactgtgc aagacgagac    300

tacgatggta ggaggggggc ctggttttct tactggggcc aagggactct ggtcactgtc    360

tctgca                                                               366
```

<210> SEQ ID NO 51
<211> LENGTH: 318
<212> TYPE: DNA
<213> ORGANISM: Artificial Sequence
<220> FEATURE:
<223> OTHER INFORMATION: Synthetic

<400> SEQUENCE: 51

```
caaattgttc tcacccagtc tccagcactc atgtctgcat ctccagggga gaaggtcacc     60

gtgacctgca ctgccagctc aagtgtaagt tacatgtact ggtaccagca gaagccaaga    120

tcctccccca aaccctggat ttatctcaca tccaacctgg cttctggagt ccctactcgc    180

ttcagtggca gtgggtctgg gacctcttat tctctcacaa tcagcagcat ggaggctgaa    240

gatgctgcca cttattactg ccagcagtgg gatagtaacc cgctcacgtt cggtgctggg    300

accaaactgg agctgaaa                                                  318
```

<210> SEQ ID NO 52
<211> LENGTH: 135
<212> TYPE: DNA
<213> ORGANISM: Artificial Sequence
<220> FEATURE:
<223> OTHER INFORMATION: Synthetic

<400> SEQUENCE: 52

```
accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135
```

<210> SEQ ID NO 53
<211> LENGTH: 117
<212> TYPE: DNA
<213> ORGANISM: Artificial Sequence
<220> FEATURE:
<223> OTHER INFORMATION: Synthetic

<400> SEQUENCE: 53
attgaagtta tgtatcctcc tccttaccta gacaatgaga agagcaatgg aaccattatc 60
catgtgaaag ggaaacacct ttgtccaagt cccctatttc ccggaccttc taagccc 117

<210> SEQ ID NO 54
<211> LENGTH: 72
<212> TYPE: DNA
<213> ORGANISM: Artificial Sequence
<220> FEATURE:
<223> OTHER INFORMATION: Synthetic

<400> SEQUENCE: 54
atctacatct gggcgccctt ggccgggact tgtggggtcc ttctcctgtc actggttatc 60
accctttact gc 72

<210> SEQ ID NO 55
<211> LENGTH: 81
<212> TYPE: DNA
<213> ORGANISM: Artificial Sequence
<220> FEATURE:
<223> OTHER INFORMATION: Synthetic

<400> SEQUENCE: 55
ttttgggtgc tggtggtggt tgggggagtc ctggcttgct atagcttgct agtaacagtg 60
gcctttatta ttttctgggt g 81

<210> SEQ ID NO 56
<211> LENGTH: 123
<212> TYPE: DNA
<213> ORGANISM: Artificial Sequence
<220> FEATURE:
<223> OTHER INFORMATION: Synthetic

<400> SEQUENCE: 56
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 57
<211> LENGTH: 123
<212> TYPE: DNA
<213> ORGANISM: Artificial Sequence
<220> FEATURE:
<223> OTHER INFORMATION: Synthetic

<400> SEQUENCE: 57
aaacggggca gaaagaaact cctgtatata ttcaaacaac catttatgag accagtacaa 60
actactcaag aggaagatgg ctgtagctgc cgatttccag aagaagaaga aggaggatgt 120
gaa 123

<210> SEQ ID NO 58
<211> LENGTH: 342
<212> TYPE: DNA
<213> ORGANISM: Artificial Sequence
<220> FEATURE:
<223> OTHER INFORMATION: Synthetic

<400> SEQUENCE: 58

```
ctgagagtga agttcagcag gagcgcagac gcccccgcgt accagcaggg ccagaaccag     60

ctctataacg agctcaatct aggacgaaga gaggagtacg atgttttgga caagagacgt    120

ggccgggacc ctgagatggg gggaaagccg agaaggaaga accctcagga aggcctgtac    180

aatgaactgc agaaagataa gatggcggag gcctacagtg agattgggat gaaaggcgag    240

cgccggaggg gcaaggggca cgatggcctt taccagggtc tcagtacagc caccaaggac    300

acctacgacg cccttcacat gcaggccctg ccccctcgct aa                       342


<210> SEQ ID NO 59
<211> LENGTH: 714
<212> TYPE: DNA
<213> ORGANISM: Artificial Sequence
<220> FEATURE:
<223> OTHER INFORMATION: Synthetic

<400> SEQUENCE: 59

ggtgtccagt gtgacgtgaa gttggtggag tctgggggag gcttagtgaa gcctggaggg     60

tccctgaaac tctcctgtgc agcctctgga ttcactttca gtagatacac catgtcttgg    120

gttcgccaga ctccggagaa gaggctggag tgggtcgcaa ccattagtaa tagtggtagt    180

tatacctact atcgagacag tgtgaagggc cgattcacca tctccagaga caatgccaag    240

aacaccctgt acctgcaaat gagcagtctg aagtctgagg acacagccat gtattactgt    300

acaagggggt cgccctgggg ccaagggact ctggtcactg tctctgcagg tggcggtggc    360

tcgggcggtg gtgggtcggg tggcggcgga tctgacatcc agatgactca gtctccagat    420

tcactgtctg catctgtggg agaaactgtc accatcacat gtggagcaag tgagaacatt    480

tacggtgctt taaattggta tcagcggaaa cagggaaaat ctcctcagct cctgatctat    540

ggtgcaacca agttggcaga tggcatgtca tcgaggttca gtggcagtgg atctaataga    600

cagtattctc tcaagatcag tagcctgcat cctgacgatg ttgcaacgta ttactgtcaa    660

aatgtgttaa gtaagccgta cgcgttcgga ggggggacca aactggaaat aaaa          714


<210> SEQ ID NO 60
<211> LENGTH: 741
<212> TYPE: DNA
<213> ORGANISM: Artificial Sequence
<220> FEATURE:
<223> OTHER INFORMATION: Synthetic

<400> SEQUENCE: 60

gaggtgaagc tgcagcaatc aggggctgac ctggcaacac ctggggcttc agtgaagttg     60

tcctgcaagg cttctggcta tacctttagt acctactgga tgcagtgggt aaaacagagg    120

cctggacagg gtctggaatg gattgggact atttatcctg gagatggtga tactaggtac    180

actcagaagt tcaagggcaa ggccacattg actgcagata aatcctccag tacagcccac    240

atgcaactca gcagcttggc atctgaggac tctgcggtct attattgtgc aagaggggga    300

ctctattatg gttacgacat tgcttactgg ggccaaggga ctctggtcac tgtctctgca    360

ggtggcggtg gctcgggcgg tggtgggtcg ggtggcggcg gatctgatat tttgatgacc    420

caaactccac tctccctgcc tgtcagtctt ggagatcaag cctccatctc ttgcagatct    480

agtcagagca ttgtacatag taatggaaac acctatttag aatggtacct gcagaaacca    540

ggccagtctc caaagcccct gataaagaaa gtctccaacc gattttctgg ggtcccagac    600

aggttcagtg gcagtggatc agggacagaa ttcacactca agatcagcag agtggaggct    660

gaggatctgg gagtttatta ctgctttcaa ggttcacatg ttccattcac gttcggctcg    720
```

gggacaaagt tggaaataaa a 741

<210> SEQ ID NO 61
<211> LENGTH: 726
<212> TYPE: DNA
<213> ORGANISM: Artificial Sequence
<220> FEATURE:
<223> OTHER INFORMATION: Synthetic

<400> SEQUENCE: 61
gaggtgaagc tggtggagtc tggaggaggc ttggtccagc cggggggtc tctgagactc 60 tcctgttcaa tttctggatt caccttcact gattactaca tgaactgggt ccgccagtct 120
ccaggaaagg cacttgagtg gttgggtttt attagaaaca aagttaatgg tgacacaaca 180
gaatatagtg catctgtgaa gggtcggttc accatctcca gagatatttc ccagagcatc 240
ctctatcttc aaatgaacac cctgagaact gaggacagtg ccacttatta ctgtgcgaga 300
gataagggaa tagcgtacta ctttgactat tggggccaag gcaccactct cacagtctcc 360
tcaggtggcg gtggctcggg cggtggtggg tcgggtggcg gcggatctca aattgttctc 420
tcccagtctc cagcaatcct gtttgcatct ccaggggaga aggtcacaat gacttgtagg 480
gccagctcaa gtgtaagtta cattcactgg taccagcaga agccaggatc ctcccccaaa 540
ccctggattc atggcacatc caacctggct tctggagtcc ctgctcgctt cagtggcagt 600
gggtctggga cctcttactc tctcacaatc agcagaatgg aggctgaaga tgccgccaca 660
tattactgcc agcagtggag tagtaattta tccacgttcg gagggggac caagctggaa 720 ataaaa 726

<210> SEQ ID NO 62
<211> LENGTH: 711
<212> TYPE: DNA
<213> ORGANISM: Artificial Sequence
<220> FEATURE:
<223> OTHER INFORMATION: Synthetic

<400> SEQUENCE: 62
caggtgcagc tgaaggagtc aggacctggc ctggtggcgc cctcacagaa cctgtccatc 60
acatgcactg tctctgggtt ctcattaacc agctatgcta taaactgggt tcgccagcca 120
ccaggaaagg gtctggagtg gcttggaata atatggactg gtggaggcac aaattataat 180
tcagctctca aatccagact gagcatcagc aaagacaact ccaagagtca agttttctta 240
aaaatgaaca gtctgcaaac tgatgacaca gccaggtact actgtgcctc gggggtgtac 300
tactttgact actggggcct aggcaccact ctcacagtct cctcaggtgg cggtggctcg 360
ggcggtggtg ggtcgggtgg cggcggatct gacattgtga tgacccagtc tcacaaattc 420
atgtccacat cagtaggaga cagggtcagc atcacctgca aggccagtca ggatgtgact 480
actgctgtag cctggtatca acaaaaacca gggcaatctc ctaaagtact gattttctgg 540
gcatccaccc ggcacactgg agtccctgat cgcttcacag gcagtggatc tgggacagat 600
tatactctca ccatcagcag tgtgcaggct gaagacctgg cactttatta ctgtcagcaa 660
tattatagaa ctcctcggac gttcggtgga ggcaccaaac tggaaatcaa a 711

<210> SEQ ID NO 63
<211> LENGTH: 729
<212> TYPE: DNA
<213> ORGANISM: Artificial Sequence
<220> FEATURE:

<223> OTHER INFORMATION: Synthetic

<400> SEQUENCE: 63
gaggtgaagc tgcaggaatc tggagctgag ctggtgaagc ctggggcttc agtgaagatc 60
tcctgcaagg cttctggcta cacattcaat gactacaaca tggactatct gaagcagagc 120
catggaaaga gccttgagtg gattggagat attaatccta actatgatag cactatctac 180
aaccagaagt tcaagggcaa ggccacattg actgtagaca agtcctccag cacagcctac 240
atggagctcc gcagcctgac atctgaggac tctgcagtct attactgtgc aagacgagac 300
tacgatggta ggagggggc ctggttttct tactggggcc aagggactct ggtcactgtc 360
tctgcaggtg gcggtggctc gggcggtggt gggtcgggtg gcggcggatc tcaaattgtt 420
ctcacccagt ctccagcact catgtctgca tctccagggg agaaggtcac cgtgacctgc 480
actgccagct caagtgtaag ttacatgtac tggtaccagc agaagccaag atcctccccc 540
aaaccctgga tttatctcac atccaacctg gcttctggag tccctactcg cttcagtggc 600
agtgggtctg ggacctctta ttctctcaca atcagcagca tggaggctga agatgctgcc 660
acttattact gccagcagtg ggatagtaac ccgctcacgt tcggtgctgg gaccaaactg 720
gagctgaaa 729

<210> SEQ ID NO 64
<211> LENGTH: 714
<212> TYPE: DNA
<213> ORGANISM: Artificial Sequence
<220> FEATURE:
<223> OTHER INFORMATION: Synthetic

<400> SEQUENCE: 64
gacatccaga tgactcagtc tccagattca ctgtctgcat ctgtgggaga aactgtcacc 60
atcacatgtg gagcaagtga gaacatttac ggtgctttaa attggtatca gcggaaacag 120
ggaaaatctc ctcagctcct gatctatggt gcaaccaagt tggcagatgg catgtcatcg 180
aggttcagtg gcagtggatc taatagacag tattctctca agatcagtag cctgcatcct 240
gacgatgttg caacgtatta ctgtcaaaat gtgttaagta agccgtacgc gttcggaggg 300
gggaccaaac tggaaataaa aggtggcggt ggctcgggcg gtggtgggtc gggtggcggc 360
ggatctggtg tccagtgtga cgtgaagttg gtggagtctg ggggaggctt agtgaagcct 420
ggagggtccc tgaaactctc ctgtgcagcc tctggattca ctttcagtag atacaccatg 480
tcttgggttc gccagactcc ggagaagagg ctggagtggg tcgcaaccat tagtaatagt 540
ggtagttata cctactatcg agacagtgtg aagggccgat tcaccatctc cagagacaat 600
gccaagaaca ccctgtacct gcaaatgagc agtctgaagt ctgaggacac agccatgtat 660
tactgtacaa gggggtcgcc ctggggccaa gggactctgg tcactgtctc tgca 714

<210> SEQ ID NO 65
<211> LENGTH: 741
<212> TYPE: DNA
<213> ORGANISM: Artificial Sequence
<220> FEATURE:
<223> OTHER INFORMATION: Synthetic

<400> SEQUENCE: 65
gatattttga tgacccaaac tccactctcc ctgcctgtca gtcttggaga tcaagcctcc 60
atctcttgca gatctagtca gagcattgta catagtaatg gaaacaccta tttagaatgg 120
tacctgcaga aaccaggcca gtctccaaag cccctgataa agaaagtctc caaccgattt 180

```
tctggggtcc cagacaggtt cagtggcagt ggatcaggga cagaattcac actcaagatc    240

agcagagtgg aggctgagga tctgggagtt tattactgct ttcaaggttc acatgttcca    300

ttcacgttcg gctcggggac aaagttggaa ataaaaggtg gcggtggctc gggcggtggt    360

gggtcgggtg gcggcggatc tgaggtgaag ctgcagcaat caggggctga cctggcaaca    420

cctggggctt cagtgaagtt gtcctgcaag gcttctggct atacctttag tacctactgg    480

atgcagtggg taaaacagag gcctggacag ggtctggaat ggattgggac tatttatcct    540

ggagatggtg atactaggta cactcagaag ttcaagggca aggccacatt gactgcagat    600

aaatcctcca gtacagccca catgcaactc agcagcttgg catctgagga ctctgcggtc    660

tattattgtg caagaggggg actctattat ggttacgaca ttgcttactg gggccaaggg    720

actctggtca ctgtctctgc a                                              741
```

<210> SEQ ID NO 66
<211> LENGTH: 726
<212> TYPE: DNA
<213> ORGANISM: Artificial Sequence
<220> FEATURE:
<223> OTHER INFORMATION: Synthetic

<400> SEQUENCE: 66

```
caaattgttc tctcccagtc tccagcaatc ctgtttgcat ctccagggga gaaggtcaca     60

atgacttgta gggccagctc aagtgtaagt tacattcact ggtaccagca gaagccagga    120

tcctccccca aaccctggat tcatggcaca tccaacctgg cttctggagt ccctgctcgc    180

ttcagtggca gtgggtctgg gacctcttac tctctcacaa tcagcagaat ggaggctgaa    240

gatgccgcca catattactg ccagcagtgg agtagtaatt tatccacgtt cggagggggg    300

accaagctgg aaataaaagg tggcggtggc tcgggcggtg gtgggtcggg tggcggcgga    360

tctgaggtga agctggtgga gtctggagga ggcttggtcc agccgggggg gtctctgaga    420

ctctcctgtt caatttctgg attcaccttc actgattact acatgaactg ggtccgccag    480

tctccaggaa aggcacttga gtggttgggt tttattagaa acaaagttaa tggtgacaca    540

acagaatata gtgcatctgt gaagggtcgg ttcaccatct ccagagatat ttcccagagc    600

atcctctatc ttcaaatgaa caccctgaga actgaggaca gtgccactta ttactgtgcg    660

agagataagg gaatagcgta ctactttgac tattggggcc aaggcaccac tctcacagtc    720

tcctca                                                               726
```

<210> SEQ ID NO 67
<211> LENGTH: 711
<212> TYPE: DNA
<213> ORGANISM: Artificial Sequence
<220> FEATURE:
<223> OTHER INFORMATION: Synthetic

<400> SEQUENCE: 67

```
gacattgtga tgacccagtc tcacaaattc atgtccacat cagtaggaga cagggtcagc     60

atcacctgca aggccagtca ggatgtgact actgctgtag cctggtatca acaaaaacca    120

gggcaatctc ctaaagtact gattttctgg gcatccaccc ggcacactgg agtccctgat    180

cgcttcacag gcagtggatc tgggacagat tatactctca ccatcagcag tgtgcaggct    240

gaagacctgg cactttatta ctgtcagcaa tattatagaa ctcctcggac gttcggtgga    300

ggcaccaaac tggaaatcaa aggtggcggt ggctcgggcg gtggtgggtc gggtggcggc    360
```

```
ggatctcagg tgcagctgaa ggagtcagga cctggcctgg tggcgccctc acagaacctg    420

tccatcacat gcactgtctc tgggttctca ttaaccagct atgctataaa ctgggttcgc    480

cagccaccag gaaagggtct ggagtggctt ggaataatat ggactggtgg aggcacaaat    540

tataattcag ctctcaaatc cagactgagc atcagcaaag acaactccaa gagtcaagtt    600

ttcttaaaaa tgaacagtct gcaaactgat gacacagcca ggtactactg tgcctcgggg    660

gtgtactact ttgactactg gggcctaggc accactctca cagtctcctc a             711
```

<210> SEQ ID NO 68
<211> LENGTH: 729
<212> TYPE: DNA
<213> ORGANISM: Artificial Sequence
<220> FEATURE:
<223> OTHER INFORMATION: Synthetic

<400> SEQUENCE: 68

```
caaattgttc tcacccagtc tccagcactc atgtctgcat ctccagggga gaaggtcacc     60

gtgacctgca ctgccagctc aagtgtaagt tacatgtact ggtaccagca gaagccaaga    120

tcctccccca aaccctggat ttatctcaca tccaacctgg cttctggagt ccctactcgc    180

ttcagtggca gtgggtctgg gacctcttat tctctcacaa tcagcagcat ggaggctgaa    240

gatgctgcca cttattactg ccagcagtgg gatagtaacc cgctcacgtt cggtgctggg    300

accaaactgg agctgaaagg tggcggtggc tcgggcggtg gtgggtcggg tggcggcgga    360

tctgaggtga agctgcagga atctggagct gagctggtga agcctggggc ttcagtgaag    420

atctcctgca aggcttctgg ctacacattc aatgactaca acatggacta tctgaagcag    480

agccatggaa agagccttga gtggattgga gatattaatc ctaactatga tagcactatc    540

tacaaccaga agttcaaggg caaggccaca ttgactgtag acaagtcctc cagcacagcc    600

tacatggagc tccgcagcct gacatctgag gactctgcag tctattactg tgcaagacga    660

gactacgatg gtaggagggg ggcctggttt tcttactggg gccaagggac tctggtcact    720

gtctctgca                                                            729
```

<210> SEQ ID NO 69
<211> LENGTH: 2169
<212> TYPE: DNA
<213> ORGANISM: Artificial Sequence
<220> FEATURE:
<223> OTHER INFORMATION: Synthetic

<400> SEQUENCE: 69

```
ggtgtccagt gtgacgtgaa gttggtggag tctgggggag gcttagtgaa gcctggaggg     60

tccctgaaac tctcctgtgc agcctctgga ttcactttca gtagatacac catgtcttgg    120

gttcgccaga ctccggagaa gaggctggag tgggtcgcaa ccattagtaa tagtggtagt    180

tatacctact atcgagacag tgtgaagggc cgattcacca tctccagaga caatgccaag    240

aacaccctgt acctgcaaat gagcagtctg aagtctgagg acacagccat gtattactgt    300

acaagggggt cgccctgggg ccaagggact ctggtcactg tctctgcagg tggcggtggc    360

tcgggcggtg gtgggtcggg tggcggcgga tctgacatcc agatgactca gtctccagat    420

tcactgtctg catctgtggg agaaactgtc accatcacat gtggagcaag tgagaacatt    480

tacggtgctt taaattggta tcagcggaaa cagggaaaat ctcctcagct cctgatctat    540

ggtgcaacca agttggcaga tggcatgtca tcgaggttca gtggcagtgg atctaataga    600

cagtattctc tcaagatcag tagcctgcat cctgacgatg ttgcaacgta ttactgtcaa    660
```

```
aatgtgttaa gtaagccgta cgcgttcgga ggggggacca aactggaaat aaaaaccacg    720

acgccagcgc cgcgaccacc aacaccggcg cccaccatcg cgtcgcagcc cctgtccctg    780

cgcccagagg cgtgccggcc agcggcgggg ggcgcagtgc acacgagggg gctggacttc    840

gcctgtgata tctacatctg ggcgcccttg gccgggactt gtggggtcct tctcctgtca    900

ctggttatca ccctttactg caaacggggc agaaagaaac tcctgtatat attcaaacaa    960

ccatttatga gaccagtaca aactactcaa gaggaagatg gctgtagctg ccgatttcca   1020

gaagaagaag aaggaggatg tgaactgaga gtgaagttca gcaggagcgc agacgccccc   1080

gcgtaccagc agggccagaa ccagctctat aacgagctca atctaggacg aagagaggag   1140

tacgatgttt tggacaagag acgtggccgg gaccctgaga tggggggaaa gccgagaagg   1200

aagaaccctc aggaaggcct gtacaatgaa ctgcagaaag ataagatggc ggaggcctac   1260

agtgagattg ggatgaaagg cgagcgccgg aggggcaagg ggcacgatgg cctttaccag   1320

ggtctcagta cagccaccaa ggacacctac gacgcccttc acatgcaggc cctgccccct   1380

cgcggatctg gcgccaccaa cttctctctg ctgaagcagg ccggcgacgt ggaggagaac   1440

ccaggcccaa tggtgagcaa gggcgaggag ctgttcaccg gggtggtgcc catcctggtc   1500

gagctggacg gcgacgtaaa cggccacaag ttcagcgtgt ccggcgaggg cgagggcgat   1560

gccacctacg gcaagctgac cctgaagttc atctgcacca ccggcaagct gcccgtgccc   1620

tggcccaccc tcgtgaccac cctgacctac ggcgtgcagt gcttcagccg ctaccccgac   1680

cacatgaagc agcacgactt cttcaagtcc gccatgcccg aaggctacgt ccaggagcgc   1740

accatcttct tcaaggacga cggcaactac aagacccgcg ccgaggtgaa gttcgagggc   1800

gacaccctgg tgaaccgcat cgagctgaag ggcatcgact tcaaggagga cggcaacatc   1860

ctggggcaca agctggagta caactacaac agccacaacg tctatatcat ggccgacaag   1920

cagaagaacg gcatcaaggt gaacttcaag atccgccaca acatcgagga cggcagcgtg   1980

cagctcgccg accactacca gcagaacacc cccatcggcg acggccccgt gctgctgccc   2040

gacaaccact acctgagcac ccagtccgcc ctgagcaaag accccaacga gaagcgcgat   2100

cacatggtcc tgctggagtt cgtgaccgcc gccgggatca ctctcggcat ggacgagctg   2160

tacaagtaa                                                           2169
```

<210> SEQ ID NO 70
<211> LENGTH: 2169
<212> TYPE: DNA
<213> ORGANISM: Artificial Sequence
<220> FEATURE:
<223> OTHER INFORMATION: Synthetic

<400> SEQUENCE: 70

```
gacatccaga tgactcagtc tccagattca ctgtctgcat ctgtgggaga aactgtcacc     60

atcacatgtg gagcaagtga gaacatttac ggtgctttaa attggtatca gcggaaacag    120

ggaaaatctc ctcagctcct gatctatggt gcaaccaagt tggcagatgg catgtcatcg    180

aggttcagtg gcagtggatc taatagacag tattctctca agatcagtag cctgcatcct    240

gacgatgttg caacgtatta ctgtcaaaat gtgttaagta agccgtacgc gttcggaggg    300

gggaccaaac tggaaataaa aggtggcggt ggctcgggcg gtggtgggtc gggtggcggc    360

ggatctggtg tccagtgtga cgtgaagttg gtggagtctg gggaggctt agtgaagcct    420

ggagggtccc tgaaactctc ctgtgcagcc tctggattca ctttcagtag atacaccatg    480
```

```
tcttgggttc gccagactcc ggagaagagg ctggagtggg tcgcaaccat tagtaatagt    540

ggtagttata cctactatcg agacagtgtg aagggccgat tcaccatctc cagagacaat    600

gccaagaaca ccctgtacct gcaaatgagc agtctgaagt ctgaggacac agccatgtat    660

tactgtacaa gggggtcgcc ctggggccaa gggactctgg tcactgtctc tgcaaccacg    720

acgccagcgc cgcgaccacc aacaccggcg cccaccatcg cgtcgcagcc cctgtccctg    780

cgcccagagg cgtgccggcc agcggcgggg ggcgcagtgc acacgagggg gctggacttc    840

gcctgtgata tctacatctg ggcgcccttg gccgggactt gtggggtcct tctcctgtca    900

ctggttatca ccctttactg caaacggggc agaaagaaac tcctgtatat attcaaacaa    960

ccatttatga gaccagtaca aactactcaa gaggaagatg gctgtagctg ccgatttcca   1020

gaagaagaag aaggaggatg tgaactgaga gtgaagttca gcaggagcgc agacgccccc   1080

gcgtaccagc agggccagaa ccagctctat aacgagctca atctaggacg aagagaggag   1140

tacgatgttt tggacaagag acgtggccgg gaccctgaga tggggggaaa gccgagaagg   1200

aagaaccctc aggaaggcct gtacaatgaa ctgcagaaag ataagatggc ggaggcctac   1260

agtgagattg ggatgaaagg cgagcgccgg aggggcaagg ggcacgatgg cctttaccag   1320

ggtctcagta cagccaccaa ggacacctac gacgcccttc acatgcaggc cctgcccccct  1380

cgcggatctg gcgccaccaa cttctctctg ctgaagcagg ccggcgacgt ggaggagaac   1440

ccaggcccaa tggtgagcaa gggcgaggag ctgttcaccg ggtggtgcc catcctggtc    1500

gagctggacg gcgacgtaaa cggccacaag ttcagcgtgt ccggcgaggg cgagggcgat   1560

gccacctacg gcaagctgac cctgaagttc atctgcacca ccggcaagct gcccgtgccc   1620

tggcccaccc tcgtgaccac cctgacctac ggcgtgcagt gcttcagccg ctaccccgac   1680

cacatgaagc agcacgactt cttcaagtcc gccatgcccg aaggctacgt ccaggagcgc   1740

accatcttct tcaaggacga cggcaactac aagacccgcg ccgaggtgaa gttcgagggc   1800

gacaccctgg tgaaccgcat cgagctgaag ggcatcgact tcaaggagga cggcaacatc   1860

ctggggcaca agctggagta caactacaac agccacaacg tctatatcat ggccgacaag   1920

cagaagaacg gcatcaaggt gaacttcaag atccgccaca acatcgagga cggcagcgtg   1980

cagctcgccg accactacca gcagaacacc cccatcggcg acggccccgt gctgctgccc   2040

gacaaccact acctgagcac ccagtccgcc ctgagcaaag accccaacga gaagcgcgat   2100

cacatggtcc tgctggagtt cgtgaccgcc gccgggatca ctctcggcat ggacgagctg   2160

tacaagtaa                                                           2169
```

```
<210> SEQ ID NO 71
<211> LENGTH: 2196
<212> TYPE: DNA
<213> ORGANISM: Artificial Sequence
<220> FEATURE:
<223> OTHER INFORMATION: Synthetic

<400> SEQUENCE: 71

gaggtgaagc tgcagcaatc aggggctgac ctggcaacac ctggggcttc agtgaagttg     60

tcctgcaagg cttctggcta tacctttagt acctactgga tgcagtgggt aaaacagagg    120

cctggacagg gtctggaatg gattgggact atttatcctg gagatggtga tactaggtac    180

actcagaagt tcaagggcaa ggccacattg actgcagata aatcctccag tacagcccac    240

atgcaactca gcagcttggc atctgaggac tctgcggtct attattgtgc aagaggggga    300

ctctattatg gttacgacat tgcttactgg ggccaaggga ctctggtcac tgtctctgca    360
```

```
ggtggcggtg gctcgggcgg tggtgggtcg ggtggcggcg gatctgatat tttgatgacc    420

caaactccac tctccctgcc tgtcagtctt ggagatcaag cctccatctc ttgcagatct    480

agtcagagca ttgtacatag taatggaaac acctatttag aatggtacct gcagaaacca    540

ggccagtctc caaagcccct gataaagaaa gtctccaacc gattttctgg ggtcccagac    600

aggttcagtg gcagtggatc agggacagaa ttcacactca agatcagcag agtggaggct    660

gaggatctgg gagtttatta ctgctttcaa ggttcacatg ttccattcac gttcggctcg    720

gggacaaagt tggaaataaa aaccacgacg ccagcgccgc gaccaccaac accggcgccc    780

accatcgcgt cgcagcccct gtccctgcgc ccagaggcgt gccggccagc ggcggggggc    840

gcagtgcaca cgagggggct ggacttcgcc tgtgatatct acatctgggc gcccttggcc    900

gggacttgtg gggtccttct cctgtcactg gttatcaccc tttactgcaa acggggcaga    960

aagaaactcc tgtatatatt caaacaacca tttatgagac cagtacaaac tactcaagag   1020

gaagatggct gtagctgccg atttccagaa gaagaagaag gaggatgtga actgagagtg   1080

aagttcagca ggagcgcaga cgcccccgcg taccagcagg gccagaacca gctctataac   1140

gagctcaatc taggacgaag agaggagtac gatgttttgg acaagagacg tggccgggac   1200

cctgagatgg ggggaaagcc gagaaggaag aaccctcagg aaggcctgta caatgaactg   1260

cagaaagata agatggcgga ggcctacagt gagattggga tgaaaggcga gcgccggagg   1320

ggcaaggggc acgatggcct ttaccagggt ctcagtacag ccaccaagga cacctacgac   1380

gcccttcaca tgcaggccct gccccctcgc ggatctggcg ccaccaactt ctctctgctg   1440

aagcaggccg gcgacgtgga ggagaaccca ggcccaatgg tgagcaaggg cgaggagctg   1500

ttcaccgggg tggtgcccat cctggtcgag ctggacggcg acgtaaacgg ccacaagttc   1560

agcgtgtccg gcgagggcga gggcgatgcc acctacggca agctgaccct gaagttcatc   1620

tgcaccaccg gcaagctgcc cgtgccctgg cccaccctcg tgaccaccct gacctacggc   1680

gtgcagtgct tcagccgcta ccccgaccac atgaagcagc acgacttctt caagtccgcc   1740

atgcccgaag gctacgtcca ggagcgcacc atcttcttca aggacgacgg caactacaag   1800

acccgcgccg aggtgaagtt cgagggcgac accctggtga accgcatcga gctgaagggc   1860

atcgacttca aggaggacgg caacatcctg gggcacaagc tggagtacaa ctacaacagc   1920

cacaacgtct atatcatggc cgacaagcag aagaacggca tcaaggtgaa cttcaagatc   1980

cgccacaaca tcgaggacgg cagcgtgcag ctcgccgacc actaccagca gaacaccccc   2040

atcggcgacg gccccgtgct gctgcccgac aaccactacc tgagcaccca gtccgccctg   2100

agcaaagacc ccaacgagaa gcgcgatcac atggtcctgc tggagttcgt gaccgccgcc   2160

gggatcactc tcggcatgga cgagctgtac aagtaa                             2196
```

```
<210> SEQ ID NO 72
<211> LENGTH: 2196
<212> TYPE: DNA
<213> ORGANISM: Artificial Sequence
<220> FEATURE:
<223> OTHER INFORMATION: Synthetic

<400> SEQUENCE: 72

gatattttga tgacccaaac tccactctcc ctgcctgtca gtcttggaga tcaagcctcc     60

atctcttgca gatctagtca gagcattgta catagtaatg gaaacaccta tttagaatgg    120

tacctgcaga aaccaggcca gtctccaaag cccctgataa agaaagtctc caaccgattt    180
```

```
tctggggtcc cagacaggtt cagtggcagt ggatcaggga cagaattcac actcaagatc    240

agcagagtgg aggctgagga tctgggagtt tattactgct ttcaaggttc acatgttcca    300

ttcacgttcg gctcggggac aaagttggaa ataaaaggtg gcggtggctc gggcggtggt    360

gggtcgggtg gcggcggatc tgaggtgaag ctgcagcaat caggggctga cctggcaaca    420

cctggggctt cagtgaagtt gtcctgcaag gcttctggct atacctttag tacctactgg    480

atgcagtggg taaaacagag gcctggacag ggtctggaat ggattgggac tatttatcct    540

ggagatggtg atactaggta cactcagaag ttcaagggca aggccacatt gactgcagat    600

aaatcctcca gtacagccca catgcaactc agcagcttgg catctgagga ctctgcggtc    660

tattattgtg caagaggggg actctattat ggttacgaca ttgcttactg gggccaaggg    720

actctggtca ctgtctctgc aaccacgacg ccagcgccgc gaccaccaac accggcgccc    780

accatcgcgt cgcagcccct gtccctgcgc ccagaggcgt gccggccagc ggcggggggc    840

gcagtgcaca cgagggggct ggacttcgcc tgtgatatct acatctgggc gcccttggcc    900

gggacttgtg gggtccttct cctgtcactg gttatcaccc tttactgcaa acggggcaga    960

aagaaactcc tgtatatatt caaacaacca tttatgagac cagtacaaac tactcaagag   1020

gaagatggct gtagctgccg atttccagaa gaagaagaag gaggatgtga actgagagtg   1080

aagttcagca ggagcgcaga cgcccccgcg taccagcagg gccagaacca gctctataac   1140

gagctcaatc taggacgaag agaggagtac gatgttttgg acaagagacg tggccgggac   1200

cctgagatgg ggggaaagcc gagaaggaag aaccctcagg aaggcctgta caatgaactg   1260

cagaaagata agatggcgga ggcctacagt gagattggga tgaaaggcga gcgccggagg   1320

ggcaaggggc acgatggcct ttaccagggt ctcagtacag ccaccaagga cacctacgac   1380

gcccttcaca tgcaggccct gccccctcgc ggatctggcg ccaccaactt ctctctgctg   1440

aagcaggccg gcgacgtgga ggagaaccca ggcccaatgg tgagcaaggg cgaggagctg   1500

ttcaccgggg tggtgcccat cctggtcgag ctggacggcg acgtaaacgg ccacaagttc   1560

agcgtgtccg gcgagggcga gggcgatgcc acctacggca agctgaccct gaagttcatc   1620

tgcaccaccg gcaagctgcc cgtgccctgg cccaccctcg tgaccaccct gacctacggc   1680

gtgcagtgct tcagccgcta ccccgaccac atgaagcagc acgacttctt caagtccgcc   1740

atgcccgaag gctacgtcca ggagcgcacc atcttcttca aggacgacgg caactacaag   1800

acccgcgccg aggtgaagtt cgagggcgac accctggtga accgcatcga gctgaagggc   1860

atcgacttca aggaggacgg caacatcctg gggcacaagc tggagtacaa ctacaacagc   1920

cacaacgtct atatcatggc cgacaagcag aagaacggca tcaaggtgaa cttcaagatc   1980

cgccacaaca tcgaggacgg cagcgtgcag ctcgccgacc actaccagca gaacaccccc   2040

atcggcgacg gccccgtgct gctgcccgac aaccactacc tgagcaccca gtccgccctg   2100

agcaaagacc ccaacgagaa gcgcgatcac atggtcctgc tggagttcgt gaccgccgcc   2160

gggatcactc tcggcatgga cgagctgtac aagtaa                             2196
```

<210> SEQ ID NO 73
<211> LENGTH: 2181
<212> TYPE: DNA
<213> ORGANISM: Artificial Sequence
<220> FEATURE:
<223> OTHER INFORMATION: Synthetic

<400> SEQUENCE: 73

```
gaggtgaagc tggtggagtc tggaggaggc ttggtccagc cggggggGtc tctgagactc     60
```

```
tcctgttcaa tttctggatt caccttcact gattactaca tgaactgggt ccgccagtct    120

ccaggaaagg cacttgagtg gttgggtttt attagaaaca aagttaatgg tgacacaaca    180

gaatatagtg catctgtgaa gggtcggttc accatctcca gagatatttc ccagagcatc    240

ctctatcttc aaatgaacac cctgagaact gaggacagtg ccacttatta ctgtgcgaga    300

gataagggaa tagcgtacta ctttgactat tggggccaag gcaccactct cacagtctcc    360

tcaggtggcg gtggctcggg cggtggtggg tcgggtggcg gcggatctca aattgttctc    420

tcccagtctc cagcaatcct gtttgcatct ccaggggaga aggtcacaat gacttgtagg    480

gccagctcaa gtgtaagtta cattcactgg taccagcaga agccaggatc ctcccccaaa    540

ccctggattc atggcacatc caacctggct tctggagtcc ctgctcgctt cagtggcagt    600

gggtctggga cctcttactc tctcacaatc agcagaatgg aggctgaaga tgccgccaca    660

tattactgcc agcagtggag tagtaattta tccacgttcg gagggggac caagctggaa     720

ataaaaacca cgacgccagc gccgcgacca ccaacaccgg cgcccaccat cgcgtcgcag    780

cccctgtccc tgcgcccaga ggcgtgccgg ccagcggcgg ggggcgcagt gcacacgagg    840

gggctggact tcgcctgtga tatctacatc tgggcgccct tggccgggac ttgtggggtc    900

cttctcctgt cactggttat caccctttac tgcaaacggg gcagaaagaa actcctgtat    960

atattcaaac aaccatttat gagaccagta caaactactc aagaggaaga tggctgtagc   1020

tgccgatttc cagaagaaga agaaggagga tgtgaactga gagtgaagtt cagcaggagc   1080

gcagacgccc ccgcgtacca gcagggccag aaccagctct ataacgagct caatctagga   1140

cgaagagagg agtacgatgt tttggacaag agacgtggcc gggaccctga gatgggggga   1200

aagccgagaa ggaagaaccc tcaggaaggc ctgtacaatg aactgcagaa agataagatg   1260

gcggaggcct acagtgagat tgggatgaaa ggcgagcgcc ggaggggcaa ggggcacgat   1320

ggcctttacc agggtctcag tacagccacc aaggacacct acgacgccct tcacatgcag   1380

gccctgcccc ctcgcggatc tggcgccacc aacttctctc tgctgaagca ggccggcgac   1440

gtggaggaga acccaggccc aatggtgagc aagggcgagg agctgttcac cggggtggtg   1500

cccatcctgg tcgagctgga cggcgacgta aacggccaca agttcagcgt gtccggcgag   1560

ggcgagggcg atgccaccta cggcaagctg accctgaagt tcatctgcac caccggcaag   1620

ctgcccgtgc cctggcccac cctcgtgacc accctgacct acggcgtgca gtgcttcagc   1680

cgctaccccg accacatgaa gcagcacgac ttcttcaagt ccgccatgcc cgaaggctac   1740

gtccaggagc gcaccatctt cttcaaggac gacggcaact acaagacccg cgccgaggtg   1800

aagttcgagg gcgacaccct ggtgaaccgc atcgagctga agggcatcga cttcaaggag   1860

gacggcaaca tcctggggca caagctggag tacaactaca acagccacaa cgtctatatc   1920

atggccgaca agcagaagaa cggcatcaag gtgaacttca agatccgcca caacatcgag   1980

gacggcagcg tgcagctcgc cgaccactac cagcagaaca cccccatcgg cgacggcccc   2040

gtgctgctgc ccgacaacca ctacctgagc acccagtccg ccctgagcaa agaccccaac   2100

gagaagcgcg atcacatggt cctgctggag ttcgtgaccg ccgccgggat cactctcggc   2160

atggacgagc tgtacaagta a                                              2181
```

<210> SEQ ID NO 74
<211> LENGTH: 2181
<212> TYPE: DNA
<213> ORGANISM: Artificial Sequence
<220> FEATURE:

<223> OTHER INFORMATION: Synthetic

<400> SEQUENCE: 74

```
caaattgttc tctcccagtc tccagcaatc ctgtttgcat ctccagggga gaaggtcaca      60
atgacttgta gggccagctc aagtgtaagt tacattcact ggtaccagca gaagccagga     120
tcctccccca aaccctggat tcatggcaca tccaacctgg cttctggagt ccctgctcgc     180
ttcagtggca gtgggtctgg gacctcttac tctctcacaa tcagcagaat ggaggctgaa     240
gatgccgcca catattactg ccagcagtgg agtagtaatt tatccacgtt cggagggggg     300
accaagctgg aaataaaagg tggcggtggc tcgggcggtg gtgggtcggg tggcggcgga     360
tctgaggtga agctggtgga gtctggagga ggcttggtcc agccgggggg gtctctgaga     420
ctctcctgtt caatttctgg attcaccttc actgattact acatgaactg ggtccgccag     480
tctccaggaa aggcacttga gtggttgggt tttattagaa acaaagttaa tggtgacaca     540
acagaatata gtgcatctgt gaagggtcgg ttcaccatct ccagagatat ttcccagagc     600
atcctctatc ttcaaatgaa caccctgaga actgaggaca gtgccactta ttactgtgcg     660
agagataagg gaatagcgta ctactttgac tattggggcc aaggcaccac tctcacagtc     720
tcctcaacca cgacgccagc gccgcgacca ccaacaccgg cgcccaccat cgcgtcgcag     780
cccctgtccc tgcgcccaga ggcgtgccgg ccagcggcgg ggggcgcagt gcacacgagg     840
gggctggact tcgcctgtga tatctacatc tgggcgccct tggccgggac ttgtggggtc     900
cttctcctgt cactggttat caccctttac tgcaaacggg gcagaaagaa actcctgtat     960
atattcaaac aaccatttat gagaccagta caaactactc aagaggaaga tggctgtagc    1020
tgccgatttc cagaagaaga agaaggagga tgtgaactga gagtgaagtt cagcaggagc    1080
gcagacgccc ccgcgtacca gcagggccag aaccagctct ataacgagct caatctagga    1140
cgaagagagg agtacgatgt tttggacaag agacgtggcc gggaccctga gatgggggga    1200
aagccgagaa ggaagaaccc tcaggaaggc ctgtacaatg aactgcagaa agataagatg    1260
gcggaggcct acagtgagat tgggatgaaa ggcgagcgcc ggaggggcaa ggggcacgat    1320
ggcctttacc agggtctcag tacagccacc aaggacacct acgacgccct tcacatgcag    1380
gccctgcccc ctcgcggatc tggcgccacc aacttctctc tgctgaagca ggccggcgac    1440
gtggaggaga acccaggccc aatggtgagc aagggcgagg agctgttcac cggggtggtg    1500
cccatcctgg tcgagctgga cggcgacgta aacggccaca agttcagcgt gtccggcgag    1560
ggcgagggcg atgccaccta cggcaagctg accctgaagt tcatctgcac caccggcaag    1620
ctgcccgtgc cctggcccac cctcgtgacc accctgacct acggcgtgca gtgcttcagc    1680
cgctaccccg accacatgaa gcagcacgac ttcttcaagt ccgccatgcc cgaaggctac    1740
gtccaggagc gcaccatctt cttcaaggac gacggcaact acaagacccg cgccgaggtg    1800
aagttcgagg gcgacaccct ggtgaaccgc atcgagctga agggcatcga cttcaaggag    1860
gacggcaaca tcctggggca caagctggag tacaactaca acagccacaa cgtctatatc    1920
atggccgaca agcagaagaa cggcatcaag gtgaacttca agatccgcca caacatcgag    1980
gacggcagcg tgcagctcgc cgaccactac cagcagaaca cccccatcgg cgacggcccc    2040
gtgctgctgc ccgacaacca ctacctgagc acccagtccg ccctgagcaa agaccccaac    2100
gagaagcgcg atcacatggt cctgctggag ttcgtgaccg ccgccgggat cactctcggc    2160
atggacgagc tgtacaagta a                                              2181
```

<210> SEQ ID NO 75
<211> LENGTH: 2166
<212> TYPE: DNA
<213> ORGANISM: Artificial Sequence
<220> FEATURE:
<223> OTHER INFORMATION: Synthetic

<400> SEQUENCE: 75

```
caggtgcagc tgaaggagtc aggacctggc ctggtggcgc cctcacagaa cctgtccatc     60
acatgcactg tctctgggtt ctcattaacc agctatgcta taaactgggt tcgccagcca    120
ccaggaaagg gtctggagtg gcttggaata atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtgcctc gggggtgtac    300
tactttgact actggggcct aggcaccact ctcacagtct cctcaggtgg cggtggctcg    360
ggcggtggtg ggtcgggtgg cggcggatct gacattgtga tgacccagtc tcacaaattc    420
atgtccacat cagtaggaga cagggtcagc atcacctgca aggccagtca ggatgtgact    480
actgctgtag cctggtatca acaaaaacca gggcaatctc ctaaagtact gattttctgg    540
gcatccaccc ggcacactgg agtccctgat cgcttcacag gcagtggatc tgggacagat    600
tatactctca ccatcagcag tgtgcaggct gaagacctgg cactttatta ctgtcagcaa    660
tattatagaa ctcctcggac gttcggtgga ggcaccaaac tggaaatcaa aaccacgacg    720
ccagcgccgc gaccaccaac accggcgccc accatcgcgt cgcagcccct gtccctgcgc    780
ccagaggcgt gccggccagc ggcggggggc gcagtgcaca cgagggggct ggacttcgcc    840
tgtgatatct acatctgggc gcccttggcc gggacttgtg gggtccttct cctgtcactg    900
gttatcaccc tttactgcaa acggggcaga aagaaactcc tgtatatatt caaacaacca    960
tttatgagac cagtacaaac tactcaagag gaagatggct gtagctgccg atttccagaa   1020
gaagaagaag gaggatgtga actgagagtg aagttcagca ggagcgcaga cgcccccgcg   1080
taccagcagg gccagaacca gctctataac gagctcaatc taggacgaag agaggagtac   1140
gatgttttgg acaagagacg tggccgggac cctgagatgg ggggaaagcc gagaaggaag   1200
aaccctcagg aaggcctgta caatgaactg cagaaagata agatggcgga ggcctacagt   1260
gagattggga tgaaaggcga gcgccggagg ggcaaggggc acgatggcct ttaccagggt   1320
ctcagtacag ccaccaagga cacctacgac gcccttcaca tgcaggccct gccccctcgc   1380
ggatctggcg ccaccaactt ctctctgctg aagcaggccg gcgacgtgga ggagaaccca   1440
ggcccaatgg tgagcaaggg cgaggagctg ttcaccgggg tggtgcccat cctggtcgag   1500
ctggacggcg acgtaaacgg ccacaagttc agcgtgtccg gcgagggcga gggcgatgcc   1560
acctacggca agctgaccct gaagttcatc tgcaccaccg gcaagctgcc cgtgccctgg   1620
cccaccctcg tgaccaccct gacctacggc gtgcagtgct tcagccgcta ccccgaccac   1680
atgaagcagc acgacttctt caagtccgcc atgcccgaag gctacgtcca ggagcgcacc   1740
atcttcttca aggacgacgg caactacaag acccgcgccg aggtgaagtt cgagggcgac   1800
accctggtga accgcatcga gctgaagggc atcgacttca aggaggacgg caacatcctg   1860
gggcacaagc tggagtacaa ctacaacagc cacaacgtct atatcatggc cgacaagcag   1920
aagaacggca tcaaggtgaa cttcaagatc cgccacaaca tcgaggacgg cagcgtgcag   1980
ctcgccgacc actaccagca gaacaccccc atcggcgacg gccccgtgct gctgcccgac   2040
aaccactacc tgagcaccca gtccgccctg agcaaagacc ccaacgagaa gcgcgatcac   2100
```

```
atggtcctgc tggagttcgt gaccgccgcc gggatcactc tcggcatgga cgagctgtac   2160

aagtaa                                                              2166


<210> SEQ ID NO 76
<211> LENGTH: 2166
<212> TYPE: DNA
<213> ORGANISM: Artificial Sequence
<220> FEATURE:
<223> OTHER INFORMATION: Synthetic

<400> SEQUENCE: 76

gacattgtga tgacccagtc tcacaaattc atgtccacat cagtaggaga cagggtcagc     60

atcacctgca aggccagtca ggatgtgact actgctgtag cctggtatca acaaaaacca    120

gggcaatctc ctaaagtact gattttctgg gcatccaccc ggcacactgg agtccctgat    180

cgcttcacag gcagtggatc tgggacagat tatactctca ccatcagcag tgtgcaggct    240

gaagacctgg cactttatta ctgtcagcaa tattatagaa ctcctcggac gttcggtgga    300

ggcaccaaac tggaaatcaa aggtggcggt ggctcgggcg gtggtgggtc gggtggcggc    360

ggatctcagg tgcagctgaa ggagtcagga cctggcctgg tggcgccctc acagaacctg    420

tccatcacat gcactgtctc tgggttctca ttaaccagct atgctataaa ctgggttcgc    480

cagccaccag gaaagggtct ggagtggctt ggaataatat ggactggtgg aggcacaaat    540

tataattcag ctctcaaatc cagactgagc atcagcaaag acaactccaa gagtcaagtt    600

ttcttaaaaa tgaacagtct gcaaactgat gacacagcca ggtactactg tgcctcgggg    660

gtgtactact ttgactactg gggcctaggc accactctca cagtctcctc aaccacgacg    720

ccagcgccgc gaccaccaac accggcgccc accatcgcgt cgcagcccct gtccctgcgc    780

ccagaggcgt gccggccagc ggcggggggc gcagtgcaca cgagggggct ggacttcgcc    840

tgtgatatct acatctgggc gcccttggcc gggacttgtg gggtccttct cctgtcactg    900

gttatcaccc tttactgcaa acggggcaga aagaaactcc tgtatatatt caaacaacca    960

tttatgagac cagtacaaac tactcaagag gaagatggct gtagctgccg atttccagaa   1020

gaagaagaag gaggatgtga actgagagtg aagttcagca ggagcgcaga cgcccccgcg   1080

taccagcagg gccagaacca gctctataac gagctcaatc taggacgaag agaggagtac   1140

gatgttttgg acaagagacg tggccgggac cctgagatgg ggggaaagcc gagaaggaag   1200

aaccctcagg aaggcctgta caatgaactg cagaaagata agatggcgga ggcctacagt   1260

gagattggga tgaaaggcga gcgccggagg ggcaaggggc acgatggcct ttaccagggt   1320

ctcagtacag ccaccaagga cacctacgac gcccttcaca tgcaggccct gccccctcgc   1380

ggatctggcg ccaccaactt ctctctgctg aagcaggccg gcgacgtgga ggagaaccca   1440

ggcccaatgg tgagcaaggg cgaggagctg ttcaccgggg tggtgcccat cctggtcgag   1500

ctggacggcg acgtaaacgg ccacaagttc agcgtgtccg gcgagggcga gggcgatgcc   1560

acctacggca agctgaccct gaagttcatc tgcaccaccg gcaagctgcc cgtgccctgg   1620

cccaccctcg tgaccaccct gacctacggc gtgcagtgct tcagccgcta ccccgaccac   1680

atgaagcagc acgacttctt caagtccgcc atgcccgaag gctacgtcca ggagcgcacc   1740

atcttcttca aggacgacgg caactacaag acccgcgccg aggtgaagtt cgagggcgac   1800

accctggtga accgcatcga gctgaagggc atcgacttca aggaggacgg caacatcctg   1860

gggcacaagc tggagtacaa ctacaacagc cacaacgtct atatcatggc cgacaagcag   1920

aagaacggca tcaaggtgaa cttcaagatc cgccacaaca tcgaggacgg cagcgtgcag   1980
```

```
ctcgccgacc actaccagca gaacaccccc atcggcgacg gccccgtgct gctgcccgac   2040

aaccactacc tgagcaccca gtccgccctg agcaaagacc ccaacgagaa gcgcgatcac   2100

atggtcctgc tggagttcgt gaccgccgcc gggatcactc tcggcatgga cgagctgtac   2160

aagtaa                                                              2166
```

<210> SEQ ID NO 77
<211> LENGTH: 2184
<212> TYPE: DNA
<213> ORGANISM: Artificial Sequence
<220> FEATURE:
<223> OTHER INFORMATION: Synthetic

<400> SEQUENCE: 77

```
gaggtgaagc tgcaggaatc tggagctgag ctggtgaagc ctggggcttc agtgaagatc     60

tcctgcaagg cttctggcta cacattcaat gactacaaca tggactatct gaagcagagc    120

catggaaaga gccttgagtg gattggagat attaatccta actatgatag cactatctac    180

aaccagaagt tcaagggcaa ggccacattg actgtagaca agtcctccag cacagcctac    240

atggagctcc gcagcctgac atctgaggac tctgcagtct attactgtgc aagacgagac    300

tacgatggta ggaggggggc ctggttttct tactggggcc aagggactct ggtcactgtc    360

tctgcaggtg gcggtggctc gggcggtggt gggtcgggtg gcggcggatc tcaaattgtt    420

ctcacccagt ctccagcact catgtctgca tctccagggg agaaggtcac cgtgacctgc    480

actgccagct caagtgtaag ttacatgtac tggtaccagc agaagccaag atcctccccc    540

aaaccctgga tttatctcac atccaacctg gcttctggag tccctactcg cttcagtggc    600

agtgggtctg ggacctctta ttctctcaca atcagcagca tggaggctga agatgctgcc    660

acttattact gccagcagtg ggatagtaac ccgctcacgt tcggtgctgg gaccaaactg    720

gagctgaaaa ccacgacgcc agcgccgcga ccaccaacac cggcgcccac catcgcgtcg    780

cagcccctgt ccctgcgccc agaggcgtgc cggccagcgg cggggggcgc agtgcacacg    840

agggggctgg acttcgcctg tgatatctac atctgggcgc ccttggccgg gacttgtggg    900

gtccttctcc tgtcactggt tatcaccctt tactgcaaac ggggcagaaa gaaactcctg    960

tatatattca aacaaccatt tatgagacca gtacaaacta ctcaagagga agatggctgt   1020

agctgccgat ttccagaaga agaagaagga ggatgtgaac tgagagtgaa gttcagcagg   1080

agcgcagacg cccccgcgta ccagcagggc cagaaccagc tctataacga gctcaatcta   1140

ggacgaagag aggagtacga tgttttggac aagagacgtg gccgggaccc tgagatgggg   1200

ggaaagccga gaaggaagaa ccctcaggaa ggcctgtaca atgaactgca gaaagataag   1260

atggcggagg cctacagtga gattgggatg aaaggcgagc gccggagggg caaggggcac   1320

gatggccttt accagggtct cagtacagcc accaaggaca cctacgacgc ccttcacatg   1380

caggccctgc cccctcgcgg atctggcgcc accaacttct ctctgctgaa gcaggccggc   1440

gacgtggagg agaacccagg cccaatggtg agcaagggcg aggagctgtt caccggggtg   1500

gtgcccatcc tggtcgagct ggacggcgac gtaaacggcc acaagttcag cgtgtccggc   1560

gagggcgagg gcgatgccac ctacggcaag ctgaccctga agttcatctg caccaccggc   1620

aagctgcccg tgccctggcc caccctcgtg accaccctga cctacggcgt gcagtgcttc   1680

agccgctacc ccgaccacat gaagcagcac gacttcttca agtccgccat gcccgaaggc   1740

tacgtccagg agcgcaccat cttcttcaag gacgacggca actacaagac ccgcgccgag   1800
```

```
gtgaagttcg agggcgacac cctggtgaac cgcatcgagc tgaagggcat cgacttcaag   1860

gaggacggca acatcctggg gcacaagctg gagtacaact acaacagcca caacgtctat   1920

atcatggccg acaagcagaa gaacggcatc aaggtgaact tcaagatccg ccacaacatc   1980

gaggacggca gcgtgcagct cgccgaccac taccagcaga acacccccat cggcgacggc   2040

cccgtgctgc tgcccgacaa ccactacctg agcacccagt ccgccctgag caaagacccc   2100

aacgagaagc gcgatcacat ggtcctgctg gagttcgtga ccgccgccgg gatcactctc   2160

ggcatggacg agctgtacaa gtaa                                          2184
```

<210> SEQ ID NO 78
<211> LENGTH: 2184
<212> TYPE: DNA
<213> ORGANISM: Artificial Sequence
<220> FEATURE:
<223> OTHER INFORMATION: Synthetic

<400> SEQUENCE: 78

```
caaattgttc tcacccagtc tccagcactc atgtctgcat ctccagggga gaaggtcacc     60

gtgacctgca ctgccagctc aagtgtaagt tacatgtact ggtaccagca gaagccaaga    120

tcctccccca aaccctggat ttatctcaca tccaacctgg cttctggagt ccctactcgc    180

ttcagtggca gtgggtctgg gacctcttat tctctcacaa tcagcagcat ggaggctgaa    240

gatgctgcca cttattactg ccagcagtgg gatagtaacc cgctcacgtt cggtgctggg    300

accaaactgg agctgaaagg tggcggtggc tcgggcggtg gtgggtcggg tggcggcgga    360

tctgaggtga agctgcagga atctggagct gagctggtga agcctggggc ttcagtgaag    420

atctcctgca aggcttctgg ctacacattc aatgactaca acatggacta tctgaagcag    480

agccatggaa agagccttga gtggattgga gatattaatc ctaactatga tagcactatc    540

tacaaccaga agttcaaggg caaggccaca ttgactgtag acaagtcctc cagcacagcc    600

tacatggagc tccgcagcct gacatctgag gactctgcag tctattactg tgcaagacga    660

gactacgatg gtaggagggg ggcctggttt tcttactggg gccaagggac tctggtcact    720

gtctctgcaa ccacgacgcc agcgccgcga ccaccaacac cggcgcccac catcgcgtcg    780

cagcccctgt ccctgcgccc agaggcgtgc cggccagcgg cggggggcgc agtgcacacg    840

agggggctgg acttcgcctg tgatatctac atctgggcgc ccttggccgg gacttgtggg    900

gtccttctcc tgtcactggt tatcaccctt tactgcaaac ggggcagaaa gaaactcctg    960

tatatattca aacaaccatt tatgagacca gtacaaacta ctcaagagga agatggctgt   1020

agctgccgat ttccagaaga agaagaagga ggatgtgaac tgagagtgaa gttcagcagg   1080

agcgcagacg cccccgcgta ccagcagggc cagaaccagc tctataacga gctcaatcta   1140

ggacgaagag aggagtacga tgttttggac aagagacgtg gccgggaccc tgagatgggg   1200

ggaaagccga gaaggaagaa ccctcaggaa ggcctgtaca atgaactgca gaaagataag   1260

atggcggagg cctacagtga gattgggatg aaaggcgagc gccggagggg caaggggcac   1320

gatggccttt accagggtct cagtacagcc accaaggaca cctacgacgc ccttcacatg   1380

caggccctgc cccctcgcgg atctggcgcc accaacttct ctctgctgaa gcaggccggc   1440

gacgtggagg agaacccagg cccaatggtg agcaagggcg aggagctgtt caccggggtg   1500

gtgcccatcc tggtcgagct ggacggcgac gtaaacggcc acaagttcag cgtgtccggc   1560

gagggcgagg gcgatgccac ctacggcaag ctgaccctga agttcatctg caccaccggc   1620

aagctgcccg tgccctggcc caccctcgtg accaccctga cctacggcgt gcagtgcttc   1680
```

```
agccgctacc ccgaccacat gaagcagcac gacttcttca agtccgccat gcccgaaggc   1740
tacgtccagg agcgcaccat cttcttcaag gacgacggca actacaagac ccgcgccgag   1800
gtgaagttcg agggcgacac cctggtgaac cgcatcgagc tgaagggcat cgacttcaag   1860
gaggacggca acatcctggg gcacaagctg gagtacaact acaacagcca caacgtctat   1920
atcatggccg acaagcagaa gaacggcatc aaggtgaact tcaagatccg ccacaacatc   1980
gaggacggca gcgtgcagct cgccgaccac taccagcaga acacccccat cggcgacggc   2040
cccgtgctgc tgcccgacaa ccactacctg agcacccagt ccgccctgag caaagacccc   2100
aacgagaagc gcgatcacat ggtcctgctg gagttcgtga ccgccgccgg gatcactctc   2160
ggcatggacg agctgtacaa gtaa                                          2184
```

<210> SEQ ID NO 79
<211> LENGTH: 1386
<212> TYPE: DNA
<213> ORGANISM: Artificial Sequence
<220> FEATURE:
<223> OTHER INFORMATION: Synthetic

<400> SEQUENCE: 79

```
ggtgtccagt gtgacgtgaa gttggtggag tctgggggag gcttagtgaa gcctggaggg     60
tccctgaaac tctcctgtgc agcctctgga ttcactttca gtagatacac catgtcttgg    120
gttcgccaga ctccggagaa gaggctggag tgggtcgcaa ccattagtaa tagtggtagt    180
tatacctact atcgagacag tgtgaagggc cgattcacca tctccagaga caatgccaag    240
aacaccctgt acctgcaaat gagcagtctg aagtctgagg acacagccat gtattactgt    300
acaagggggt cgccctgggg ccaagggact ctggtcactg tctctgcagg tggcggtggc    360
tcgggcggtg gtgggtcggg tggcggcgga tctgacatcc agatgactca gtctccagat    420
tcactgtctg catctgtggg agaaactgtc accatcacat gtggagcaag tgagaacatt    480
tacggtgctt taaattggta tcagcggaaa cagggaaaat ctcctcagct cctgatctat    540
ggtgcaacca agttggcaga tggcatgtca tcgaggttca gtggcagtgg atctaataga    600
cagtattctc tcaagatcag tagcctgcat cctgacgatg ttgcaacgta ttactgtcaa    660
aatgtgttaa gtaagccgta cgcgttcgga ggggggacca aactggaaat aaaaaccacg    720
acgccagcgc cgcgaccacc aacaccggcg cccaccatcg cgtcgcagcc cctgtccctg    780
cgcccagagg cgtgccggcc agcggcgggg ggcgcagtgc acacgagggg gctggacttc    840
gcctgtgata tctacatctg ggcgcccttg gccgggactt gtggggtcct tctcctgtca    900
ctggttatca ccctttactg caaacggggc agaaagaaac tcctgtatat attcaaacaa    960
ccatttatga gaccagtaca aactactcaa gaggaagatg gctgtagctg ccgatttcca   1020
gaagaagaag aaggaggatg tgaactgaga gtgaagttca gcaggagcgc agacgccccc   1080
gcgtaccagc agggccagaa ccagctctat aacgagctca atctaggacg aagagaggag   1140
tacgatgttt tggacaagag acgtggccgg gaccctgaga tgggggggaaa gccgagaagg   1200
aagaaccctc aggaaggcct gtacaatgaa ctgcagaaag ataagatggc ggaggcctac   1260
agtgagattg ggatgaaagg cgagcgccgg aggggcaagg ggcacgatgg cctttaccag   1320
ggtctcagta cagccaccaa ggacacctac gacgcccttc acatgcaggc cctgcccccct   1380
cgctaa                                                              1386
```

<210> SEQ ID NO 80

<211> LENGTH: 1386
<212> TYPE: DNA
<213> ORGANISM: Artificial Sequence
<220> FEATURE:
<223> OTHER INFORMATION: Synthetic

<400> SEQUENCE: 80

```
gacatccaga tgactcagtc tccagattca ctgtctgcat ctgtgggaga aactgtcacc     60
atcacatgtg gagcaagtga gaacatttac ggtgctttaa attggtatca gcggaaacag    120
ggaaaatctc ctcagctcct gatctatggt gcaaccaagt tggcagatgg catgtcatcg    180
aggttcagtg gcagtggatc taatagacag tattctctca agatcagtag cctgcatcct    240
gacgatgttg caacgtatta ctgtcaaaat gtgttaagta agccgtacgc gttcggaggg    300
gggaccaaac tggaaataaa aggtggcggt ggctcgggcg gtggtgggtc gggtggcggc    360
ggatctggtg tccagtgtga cgtgaagttg gtggagtctg gggaggctt agtgaagcct    420
ggagggtccc tgaaactctc ctgtgcagcc tctggattca ctttcagtag atacaccatg    480
tcttgggttc gccagactcc ggagaagagg ctggagtggg tcgcaaccat tagtaatagt    540
ggtagttata cctactatcg agacagtgtg aagggccgat tcaccatctc cagagacaat    600
gccaagaaca ccctgtacct gcaaatgagc agtctgaagt ctgaggacac agccatgtat    660
tactgtacaa gggggtcgcc ctggggccaa gggactctgg tcactgtctc tgcaaccacg    720
acgccagcgc cgcgaccacc aacaccggcg cccaccatcg cgtcgcagcc cctgtccctg    780
cgcccagagg cgtgccggcc agcggcgggg ggcgcagtgc acacgagggg gctggacttc    840
gcctgtgata tctacatctg ggcgcccttg gccgggactt gtggggtcct tctcctgtca    900
ctggttatca ccctttactg caaacggggc agaaagaaac tcctgtatat attcaaacaa    960
ccatttatga gaccagtaca aactactcaa gaggaagatg gctgtagctg ccgatttcca   1020
gaagaagaag aaggaggatg tgaactgaga gtgaagttca gcaggagcgc agacgccccc   1080
gcgtaccagc agggccagaa ccagctctat aacgagctca atctaggacg aagagaggag   1140
tacgatgttt tggacaagag acgtggccgg gaccctgaga tgggggggaaa gccgagaagg   1200
aagaaccctc aggaaggcct gtacaatgaa ctgcagaaag ataagatggc ggaggcctac   1260
agtgagattg ggatgaaagg cgagcgccgg aggggcaagg ggcacgatgg cctttaccag   1320
ggtctcagta cagccaccaa ggacacctac gacgcccttc acatgcaggc cctgcccccct   1380
cgctaa                                                               1386
```

<210> SEQ ID NO 81
<211> LENGTH: 1413
<212> TYPE: DNA
<213> ORGANISM: Artificial Sequence
<220> FEATURE:
<223> OTHER INFORMATION: Synthetic

<400> SEQUENCE: 81

```
gaggtgaagc tgcagcaatc aggggctgac ctggcaacac ctggggcttc agtgaagttg     60
tcctgcaagg cttctggcta tacctttagt acctactgga tgcagtgggt aaaacagagg    120
cctggacagg gtctggaatg gattgggact atttatcctg gagatggtga tactaggtac    180
actcagaagt tcaagggcaa ggccacattg actgcagata aatcctccag tacagcccac    240
atgcaactca gcagcttggc atctgaggac tctgcggtct attattgtgc aagaggggga    300
ctctattatg gttacgacat tgcttactgg ggccaaggga ctctggtcac tgtctctgca    360
ggtggcggtg gctcgggcgg tggtgggtcg ggtggcggcg gatctgatat tttgatgacc    420
```

```
caaactccac tctccctgcc tgtcagtctt ggagatcaag cctccatctc ttgcagatct    480

agtcagagca ttgtacatag taatggaaac acctatttag aatggtacct gcagaaacca    540

ggccagtctc caaagcccct gataaagaaa gtctccaacc gattttctgg ggtcccagac    600

aggttcagtg gcagtggatc agggacagaa ttcacactca agatcagcag agtggaggct    660

gaggatctgg gagtttatta ctgctttcaa ggttcacatg ttccattcac gttcggctcg    720

gggacaaagt tggaaataaa aaccacgacg ccagcgccgc gaccaccaac accggcgccc    780

accatcgcgt cgcagcccct gtccctgcgc ccagaggcgt gccggccagc ggcggggggc    840

gcagtgcaca cgagggggct ggacttcgcc tgtgatatct acatctgggc gcccttggcc    900

gggacttgtg gggtccttct cctgtcactg gttatcaccc tttactgcaa acggggcaga    960

aagaaactcc tgtatatatt caaacaacca tttatgagac cagtacaaac tactcaagag   1020

gaagatggct gtagctgccg atttccagaa gaagaagaag gaggatgtga actgagagtg   1080

aagttcagca ggagcgcaga cgcccccgcg taccagcagg gccagaacca gctctataac   1140

gagctcaatc taggacgaag agaggagtac gatgttttgg acaagagacg tggccgggac   1200

cctgagatgg ggggaaagcc gagaaggaag aaccctcagg aaggcctgta caatgaactg   1260

cagaaagata agatggcgga ggcctacagt gagattggga tgaaaggcga gcgccggagg   1320

ggcaaggggc acgatggcct ttaccagggt ctcagtacag ccaccaagga cacctacgac   1380

gcccttcaca tgcaggccct gccccctcgc taa                                1413
```

```
<210> SEQ ID NO 82
<211> LENGTH: 1413
<212> TYPE: DNA
<213> ORGANISM: Artificial Sequence
<220> FEATURE:
<223> OTHER INFORMATION: Synthetic

<400> SEQUENCE: 82
```

```
gatattttga tgacccaaac tccactctcc ctgcctgtca gtcttggaga tcaagcctcc     60

atctcttgca gatctagtca gagcattgta catagtaatg gaaacaccta tttagaatgg    120

tacctgcaga aaccaggcca gtctccaaag cccctgataa agaaagtctc caaccgattt    180

tctggggtcc cagacaggtt cagtggcagt ggatcaggga cagaattcac actcaagatc    240

agcagagtgg aggctgagga tctgggagtt tattactgct ttcaaggttc acatgttcca    300

ttcacgttcg gctcggggac aaagttggaa ataaaaggtg gcggtggctc gggcggtggt    360

gggtcgggtg gcggcggatc tgaggtgaag ctgcagcaat caggggctga cctggcaaca    420

cctggggctt cagtgaagtt gtcctgcaag gcttctggct ataccttttag tacctactgg    480

atgcagtggg taaaacagag gcctggacag ggtctggaat ggattgggac tatttatcct    540

ggagatggtg atactaggta cactcagaag ttcaagggca aggccacatt gactgcagat    600

aaatcctcca gtacagccca catgcaactc agcagcttgg catctgagga ctctgcggtc    660

tattattgtg caagaggggg actctattat ggttacgaca ttgcttactg gggccaaggg    720

actctggtca ctgtctctgc aaccacgacg ccagcgccgc gaccaccaac accggcgccc    780

accatcgcgt cgcagcccct gtccctgcgc ccagaggcgt gccggccagc ggcggggggc    840

gcagtgcaca cgagggggct ggacttcgcc tgtgatatct acatctgggc gcccttggcc    900

gggacttgtg gggtccttct cctgtcactg gttatcaccc tttactgcaa acggggcaga    960

aagaaactcc tgtatatatt caaacaacca tttatgagac cagtacaaac tactcaagag   1020
```

```
gaagatggct gtagctgccg atttccagaa gaagaagaag gaggatgtga actgagagtg   1080
aagttcagca ggagcgcaga cgcccccgcg taccagcagg gccagaacca gctctataac   1140
gagctcaatc taggacgaag agaggagtac gatgttttgg acaagagacg tggccgggac   1200
cctgagatgg ggggaaagcc gagaaggaag aaccctcagg aaggcctgta caatgaactg   1260
cagaaagata agatggcgga ggcctacagt gagattggga tgaaaggcga gcgccggagg   1320
ggcaaggggc acgatggcct ttaccagggt ctcagtacag ccaccaagga cacctacgac   1380
gcccttcaca tgcaggccct gccccctcgc taa                                1413
```

<210> SEQ ID NO 83
<211> LENGTH: 1398
<212> TYPE: DNA
<213> ORGANISM: Artificial Sequence
<220> FEATURE:
<223> OTHER INFORMATION: Synthetic

<400> SEQUENCE: 83

```
gaggtgaagc tggtggagtc tggaggaggc ttggtccagc cggggggtc tctgagactc      60
tcctgttcaa tttctggatt caccttcact gattactaca tgaactgggt ccgccagtct    120
ccaggaaagg cacttgagtg gttgggtttt attagaaaca aagttaatgg tgacacaaca    180
gaatatagtg catctgtgaa gggtcggttc accatctcca gagatatttc ccagagcatc    240
ctctatcttc aaatgaacac cctgagaact gaggacagtg ccacttatta ctgtgcgaga    300
gataagggaa tagcgtacta ctttgactat tggggccaag gcaccactct cacagtctcc    360
tcaggtggcg gtggctcggg cggtggtggg tcgggtggcg gcggatctca aattgttctc    420
tcccagtctc cagcaatcct gtttgcatct ccaggggaga aggtcacaat gacttgtagg    480
gccagctcaa gtgtaagtta cattcactgg taccagcaga agccaggatc ctcccccaaa    540
ccctggattc atggcacatc caacctggct tctggagtcc ctgctcgctt cagtggcagt    600
gggtctggga cctcttactc tctcacaatc agcagaatgg aggctgaaga tgccgccaca    660
tattactgcc agcagtggag tagtaattta tccacgttcg gaggggggac caagctggaa    720
ataaaaacca cgacgccagc gccgcgacca ccaacaccgg cgcccaccat cgcgtcgcag    780
cccctgtccc tgcgcccaga ggcgtgccgg ccagcggcgg ggggcgcagt gcacacgagg    840
gggctggact tcgcctgtga tatctacatc tgggcgccct tggccgggac ttgtggggtc    900
cttctcctgt cactggttat caccctttac tgcaaacggg gcagaaagaa actcctgtat    960
atattcaaac aaccatttat gagaccagta caaactactc aagaggaaga tggctgtagc   1020
tgccgatttc cagaagaaga agaaggagga tgtgaactga gagtgaagtt cagcaggagc   1080
gcagacgccc ccgcgtacca gcagggccag aaccagctct ataacgagct caatctagga   1140
cgaagagagg agtacgatgt tttggacaag agacgtggcc gggaccctga gatgggggga   1200
aagccgagaa ggaagaaccc tcaggaaggc ctgtacaatg aactgcagaa agataagatg   1260
gcggaggcct acagtgagat tgggatgaaa ggcgagcgcc ggaggggcaa ggggcacgat   1320
ggcctttacc agggtctcag tacagccacc aaggacacct acgacgccct tcacatgcag   1380
gccctgcccc ctcgctaa                                                  1398
```

<210> SEQ ID NO 84
<211> LENGTH: 1398
<212> TYPE: DNA
<213> ORGANISM: Artificial Sequence
<220> FEATURE:
<223> OTHER INFORMATION: Synthetic

<400> SEQUENCE: 84

```
caaattgttc tctcccagtc tccagcaatc ctgtttgcat ctccagggga gaaggtcaca     60
atgacttgta gggccagctc aagtgtaagt tacattcact ggtaccagca gaagccagga    120
tcctccccca aaccctggat tcatggcaca tccaacctgg cttctggagt ccctgctcgc    180
ttcagtggca gtgggtctgg gacctcttac tctctcacaa tcagcagaat ggaggctgaa    240
gatgccgcca catattactg ccagcagtgg agtagtaatt tatccacgtt cggagggggg    300
accaagctgg aaataaaagg tggcggtggc tcgggcggtg gtgggtcggg tggcggcgga    360
tctgaggtga agctggtgga gtctggagga ggcttggtcc agccgggggg gtctctgaga    420
ctctcctgtt caatttctgg attcaccttc actgattact acatgaactg ggtccgccag    480
tctccaggaa aggcacttga gtggttgggt tttattagaa acaaagttaa tggtgacaca    540
acagaatata gtgcatctgt gaagggtcgg ttcaccatct ccagagatat ttcccagagc    600
atcctctatc ttcaaatgaa caccctgaga actgaggaca gtgccactta ttactgtgcg    660
agagataagg gaatagcgta ctactttgac tattggggcc aaggcaccac tctcacagtc    720
tcctcaacca cgacgccagc gccgcgacca ccaacaccgg cgcccaccat cgcgtcgcag    780
cccctgtccc tgcgcccaga ggcgtgccgg ccagcggcgg ggggcgcagt gcacacgagg    840
gggctggact tcgcctgtga tatctacatc tgggcgccct tggccgggac ttgtggggtc    900
cttctcctgt cactggttat caccctttac tgcaaacggg gcagaaagaa actcctgtat    960
atattcaaac aaccatttat gagaccagta caaactactc aagaggaaga tggctgtagc   1020
tgccgatttc cagaagaaga agaaggagga tgtgaactga gagtgaagtt cagcaggagc   1080
gcagacgccc ccgcgtacca gcagggccag aaccagctct ataacgagct caatctagga   1140
cgaagagagg agtacgatgt tttggacaag agacgtggcc gggaccctga gatgggggga   1200
aagccgagaa ggaagaaccc tcaggaaggc ctgtacaatg aactgcagaa agataagatg   1260
gcggaggcct acagtgagat tgggatgaaa ggcgagcgcc ggaggggcaa ggggcacgat   1320
ggcctttacc agggtctcag tacagccacc aaggacacct acgacgccct tcacatgcag   1380
gccctgcccc ctcgctaa                                                 1398
```

<210> SEQ ID NO 85
<211> LENGTH: 1383
<212> TYPE: DNA
<213> ORGANISM: Artificial Sequence
<220> FEATURE:
<223> OTHER INFORMATION: Synthetic

<400> SEQUENCE: 85

```
caggtgcagc tgaaggagtc aggacctggc ctggtggcgc cctcacagaa cctgtccatc     60
acatgcactg tctctgggtt ctcattaacc agctatgcta taaactgggt tcgccagcca    120
ccaggaaagg gtctggagtg gcttggaata atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtgcctc gggggtgtac    300
tactttgact actggggcct aggcaccact ctcacagtct cctcaggtgg cggtggctcg    360
ggcggtggtg ggtcgggtgg cggcggatct gacattgtga tgacccagtc tcacaaattc    420
atgtccacat cagtaggaga cagggtcagc atcacctgca aggccagtca ggatgtgact    480
actgctgtag cctggtatca acaaaaacca gggcaatctc ctaaagtact gattttctgg    540
```

```
gcatccaccc ggcacactgg agtccctgat cgcttcacag gcagtggatc tgggacagat    600
tatactctca ccatcagcag tgtgcaggct gaagacctgg cactttatta ctgtcagcaa    660
tattatagaa ctcctcggac gttcggtgga ggcaccaaac tggaaatcaa aaccacgacg    720
ccagcgccgc gaccaccaac accggcgccc accatcgcgt cgcagcccct gtccctgcgc    780
ccagaggcgt gccggccagc ggcggggggc gcagtgcaca cgagggggct ggacttcgcc    840
tgtgatatct acatctgggc gcccttggcc gggacttgtg gggtccttct cctgtcactg    900
gttatcaccc tttactgcaa acggggcaga aagaaactcc tgtatatatt caaacaacca    960
tttatgagac cagtacaaac tactcaagag gaagatggct gtagctgccg atttccagaa   1020
gaagaagaag gaggatgtga actgagagtg aagttcagca ggagcgcaga cgcccccgcg   1080
taccagcagg gccagaacca gctctataac gagctcaatc taggacgaag agaggagtac   1140
gatgttttgg acaagagacg tggccgggac cctgagatgg ggggaaagcc gagaaggaag   1200
aaccctcagg aaggcctgta caatgaactg cagaaagata agatggcgga ggcctacagt   1260
gagattggga tgaaaggcga gcgccggagg ggcaaggggc acgatggcct ttaccagggt   1320
ctcagtacag ccaccaagga cacctacgac gcccttcaca tgcaggccct gccccctcgc   1380
taa                                                                  1383
```

```
<210> SEQ ID NO 86
<211> LENGTH: 1383
<212> TYPE: DNA
<213> ORGANISM: Artificial Sequence
<220> FEATURE:
<223> OTHER INFORMATION: Synthetic

<400> SEQUENCE: 86
```

```
gacattgtga tgacccagtc tcacaaattc atgtccacat cagtaggaga cagggtcagc     60
atcacctgca aggccagtca ggatgtgact actgctgtag cctggtatca acaaaaacca    120
gggcaatctc ctaaagtact gattttctgg gcatccaccc ggcacactgg agtccctgat    180
cgcttcacag gcagtggatc tgggacagat tatactctca ccatcagcag tgtgcaggct    240
gaagacctgg cactttatta ctgtcagcaa tattatagaa ctcctcggac gttcggtgga    300
ggcaccaaac tggaaatcaa aggtggcggt ggctcgggcg gtggtgggtc gggtggcggc    360
ggatctcagg tgcagctgaa ggagtcagga cctggcctgg tggcgccctc acagaacctg    420
tccatcacat gcactgtctc tgggttctca ttaaccagct atgctataaa ctgggttcgc    480
cagccaccag gaaagggtct ggagtggctt ggaataatat ggactggtgg aggcacaaat    540
tataattcag ctctcaaatc cagactgagc atcagcaaag acaactccaa gagtcaagtt    600
ttcttaaaaa tgaacagtct gcaaactgat gacacagcca ggtactactg tgcctcgggg    660
gtgtactact ttgactactg gggcctaggc accactctca cagtctcctc aaccacgacg    720
ccagcgccgc gaccaccaac accggcgccc accatcgcgt cgcagcccct gtccctgcgc    780
ccagaggcgt gccggccagc ggcggggggc gcagtgcaca cgagggggct ggacttcgcc    840
tgtgatatct acatctgggc gcccttggcc gggacttgtg gggtccttct cctgtcactg    900
gttatcaccc tttactgcaa acggggcaga aagaaactcc tgtatatatt caaacaacca    960
tttatgagac cagtacaaac tactcaagag gaagatggct gtagctgccg atttccagaa   1020
gaagaagaag gaggatgtga actgagagtg aagttcagca ggagcgcaga cgcccccgcg   1080
taccagcagg gccagaacca gctctataac gagctcaatc taggacgaag agaggagtac   1140
gatgttttgg acaagagacg tggccgggac cctgagatgg ggggaaagcc gagaaggaag   1200
```

```
aaccctcagg aaggcctgta caatgaactg cagaaagata agatggcgga ggcctacagt   1260

gagattggga tgaaaggcga gcgccggagg ggcaaggggc acgatggcct ttaccagggt   1320

ctcagtacag ccaccaagga cacctacgac gcccttcaca tgcaggccct gccccctcgc   1380

taa                                                                 1383
```

<210> SEQ ID NO 87
<211> LENGTH: 1401
<212> TYPE: DNA
<213> ORGANISM: Artificial Sequence
<220> FEATURE:
<223> OTHER INFORMATION: Synthetic

<400> SEQUENCE: 87

```
gaggtgaagc tgcaggaatc tggagctgag ctggtgaagc ctggggcttc agtgaagatc     60

tcctgcaagg cttctggcta cacattcaat gactacaaca tggactatct gaagcagagc    120

catggaaaga gccttgagtg gattggagat attaatccta actatgatag cactatctac    180

aaccagaagt tcaagggcaa ggccacattg actgtagaca agtcctccag cacagcctac    240

atggagctcc gcagcctgac atctgaggac tctgcagtct attactgtgc aagacgagac    300

tacgatggta ggaggggggc ctggttttct tactggggcc aagggactct ggtcactgtc    360

tctgcaggtg gcggtggctc gggcggtggt gggtcgggtg gcggcggatc tcaaattgtt    420

ctcacccagt ctccagcact catgtctgca tctccagggg agaaggtcac cgtgacctgc    480

actgccagct caagtgtaag ttacatgtac tggtaccagc agaagccaag atcctccccc    540

aaaccctgga tttatctcac atccaacctg gcttctggag tccctactcg cttcagtggc    600

agtgggtctg ggacctctta ttctctcaca atcagcagca tggaggctga agatgctgcc    660

acttattact gccagcagtg ggatagtaac ccgctcacgt tcggtgctgg gaccaaactg    720

gagctgaaaa ccacgacgcc agcgccgcga ccaccaacac cggcgcccac catcgcgtcg    780

cagcccctgt ccctgcgccc agaggcgtgc cggccagcgg cggggggcgc agtgcacacg    840

agggggctgg acttcgcctg tgatatctac atctgggcgc ccttggccgg gacttgtggg    900

gtccttctcc tgtcactggt tatcaccctt tactgcaaac ggggcagaaa gaaactcctg    960

tatatattca aacaaccatt tatgagacca gtacaaacta ctcaagagga agatggctgt   1020

agctgccgat ttccagaaga agaagaagga ggatgtgaac tgagagtgaa gttcagcagg   1080

agcgcagacg cccccgcgta ccagcagggc cagaaccagc tctataacga gctcaatcta   1140

ggacgaagag aggagtacga tgttttggac aagagacgtg gccgggaccc tgagatgggg   1200

ggaaagccga gaaggaagaa ccctcaggaa ggcctgtaca atgaactgca gaaagataag   1260

atggcggagg cctacagtga gattgggatg aaaggcgagc gccggagggg caaggggcac   1320

gatggccttt accagggtct cagtacagcc accaaggaca cctacgacgc ccttcacatg   1380

caggccctgc cccctcgcta a                                             1401
```

<210> SEQ ID NO 88
<211> LENGTH: 1401
<212> TYPE: DNA
<213> ORGANISM: Artificial Sequence
<220> FEATURE:
<223> OTHER INFORMATION: Synthetic

<400> SEQUENCE: 88

```
caaattgttc tcacccagtc tccagcactc atgtctgcat ctccagggga gaaggtcacc     60
```

gtgacctgca ctgccagctc aagtgtaagt tacatgtact ggtaccagca gaagccaaga 120
tcctccccca aaccctggat ttatctcaca tccaacctgg cttctggagt ccctactcgc 180
ttcagtggca gtgggtctgg gacctcttat tctctcacaa tcagcagcat ggaggctgaa 240
gatgctgcca cttattactg ccagcagtgg gatagtaacc cgctcacgtt cggtgctggg 300
accaaactgg agctgaaagg tggcggtggc tcgggcggtg gtgggtcggg tggcggcgga 360
tctgaggtga agctgcagga atctggagct gagctggtga agcctggggc ttcagtgaag 420
atctcctgca aggcttctgg ctacacattc aatgactaca acatggacta tctgaagcag 480
agccatggaa agagccttga gtggattgga gatattaatc ctaactatga tagcactatc 540
tacaaccaga agttcaaggg caaggccaca ttgactgtag acaagtcctc cagcacagcc 600
tacatggagc tccgcagcct gacatctgag gactctgcag tctattactg tgcaagacga 660
gactacgatg gtaggagggg ggcctggttt tcttactggg gccaagggac tctggtcact 720
gtctctgcaa ccacgacgcc agcgccgcga ccaccaacac cggcgcccac catcgcgtcg 780
cagcccctgt ccctgcgccc agaggcgtgc cggccagcgg cggggggcgc agtgcacacg 840
agggggctgg acttcgcctg tgatatctac atctgggcgc ccttggccgg gacttgtggg 900
gtccttctcc tgtcactggt tatcaccctt tactgcaaac ggggcagaaa gaaactcctg 960
tatatattca aacaaccatt tatgagacca gtacaaacta ctcaagagga agatggctgt 1020
agctgccgat ttccagaaga agaagaagga ggatgtgaac tgagagtgaa gttcagcagg 1080
agcgcagacg cccccgcgta ccagcagggc cagaaccagc tctataacga gctcaatcta 1140
ggacgaagag aggagtacga tgttttggac aagagacgtg gccgggaccc tgagatgggg 1200
ggaaagccga gaaggaagaa ccctcaggaa ggcctgtaca atgaactgca gaaagataag 1260
atggcggagg cctacagtga gattgggatg aaaggcgagc gccggagggg caaggggcac 1320
gatggccttt accagggtct cagtacagcc accaaggaca cctacgacgc ccttcacatg 1380
caggccctgc cccctcgcta a 1401

<210> SEQ ID NO 89
<211> LENGTH: 2160
<212> TYPE: DNA
<213> ORGANISM: Artificial Sequence
<220> FEATURE:
<223> OTHER INFORMATION: Synthetic

<400> SEQUENCE: 89
ggtgtccagt gtgacgtgaa gttggtggag tctgggggag gcttagtgaa gcctggaggg 60
tccctgaaac tctcctgtgc agcctctgga ttcactttca gtagatacac catgtcttgg 120
gttcgccaga ctccggagaa gaggctggag tgggtcgcaa ccattagtaa tagtggtagt 180
tatacctact atcgagacag tgtgaagggc cgattcacca tctccagaga caatgccaag 240
aacaccctgt acctgcaaat gagcagtctg aagtctgagg acacagccat gtattactgt 300
acaagggggt cgccctgggg ccaagggact ctggtcactg tctctgcagg tggcggtggc 360
tcgggcggtg gtgggtcggg tggcggcgga tctgacatcc agatgactca gtctccagat 420
tcactgtctg catctgtggg agaaactgtc accatcacat gtggagcaag tgagaacatt 480
tacggtgctt taaattggta tcagcggaaa cagggaaaat ctcctcagct cctgatctat 540
ggtgcaacca agttggcaga tggcatgtca tcgaggttca gtggcagtgg atctaataga 600
cagtattctc tcaagatcag tagcctgcat cctgacgatg ttgcaacgta ttactgtcaa 660
aatgtgttaa gtaagccgta cgcgttcgga ggggggacca aactggaaat aaaaattgaa 720

```
gttatgtatc ctcctcctta cctagacaat gagaagagca atggaaccat tatccatgtg    780
aaagggaaac acctttgtcc aagtccccta tttcccggac cttctaagcc cttttgggtg    840
ctggtggtgg ttgggggagt cctggcttgc tatagcttgc tagtaacagt ggcctttatt    900
attttctggg tgaaacgggg cagaaagaaa ctcctgtata tattcaaaca accatttatg    960
agaccagtac aaactactca agaggaagat ggctgtagct gccgatttcc agaagaagaa   1020
gaaggaggat gtgaactgag agtgaagttc agcaggagcg cagacgcccc cgcgtaccag   1080
cagggccaga accagctcta taacgagctc aatctaggac gaagagagga gtacgatgtt   1140
ttggacaaga gacgtggccg ggaccctgag atggggggaa agccgagaag gaagaaccct   1200
caggaaggcc tgtacaatga actgcagaaa gataagatgg cggaggccta cagtgagatt   1260
gggatgaaag gcgagcgccg gaggggcaag gggcacgatg gcctttacca gggtctcagt   1320
acagccacca aggacaccta cgacgccctt cacatgcagg ccctgccccc tcgcggatct   1380
ggcgccacca acttctctct gctgaagcag gccggcgacg tggaggagaa cccaggccca   1440
atggtgagca agggcgagga gctgttcacc ggggtggtgc ccatcctggt cgagctggac   1500
ggcgacgtaa acggccacaa gttcagcgtg tccggcgagg gcgagggcga tgccacctac   1560
ggcaagctga ccctgaagtt catctgcacc accggcaagc tgcccgtgcc ctggcccacc   1620
ctcgtgacca ccctgaccta cggcgtgcag tgcttcagcc gctaccccga ccacatgaag   1680
cagcacgact tcttcaagtc cgccatgccc gaaggctacg tccaggagcg caccatcttc   1740
ttcaaggacg acggcaacta caagacccgc gccgaggtga agttcgaggg cgacaccctg   1800
gtgaaccgca tcgagctgaa gggcatcgac ttcaaggagg acggcaacat cctggggcac   1860
aagctggagt acaactacaa cagccacaac gtctatatca tggccgacaa gcagaagaac   1920
ggcatcaagg tgaacttcaa gatccgccac aacatcgagg acggcagcgt gcagctcgcc   1980
gaccactacc agcagaacac ccccatcggc gacggccccg tgctgctgcc cgacaaccac   2040
tacctgagca cccagtccgc cctgagcaaa gaccccaacg agaagcgcga tcacatggtc   2100
ctgctggagt tcgtgaccgc cgccgggatc actctcggca tggacgagct gtacaagtaa   2160
```

<210> SEQ ID NO 90
<211> LENGTH: 2160
<212> TYPE: DNA
<213> ORGANISM: Artificial Sequence
<220> FEATURE:
<223> OTHER INFORMATION: Synthetic

<400> SEQUENCE: 90

```
gacatccaga tgactcagtc tccagattca ctgtctgcat ctgtgggaga aactgtcacc     60
atcacatgtg gagcaagtga gaacatttac ggtgctttaa attggtatca gcggaaacag    120
ggaaaatctc ctcagctcct gatctatggt gcaaccaagt tggcagatgg catgtcatcg    180
aggttcagtg gcagtggatc taatagacag tattctctca agatcagtag cctgcatcct    240
gacgatgttg caacgtatta ctgtcaaaat gtgttaagta agccgtacgc gttcggaggg    300
gggaccaaac tggaaataaa aggtggcggt ggctcgggcg gtggtgggtc gggtggcggc    360
ggatctggtg tccagtgtga cgtgaagttg gtggagtctg gggaggctt agtgaagcct    420
ggagggtccc tgaaactctc ctgtgcagcc tctggattca ctttcagtag atacaccatg    480
tcttgggttc gccagactcc ggagaagagg ctggagtggg tcgcaaccat tagtaatagt    540
ggtagttata cctactatcg agacagtgtg aagggccgat tcaccatctc cagagacaat    600
```

```
gccaagaaca ccctgtacct gcaaatgagc agtctgaagt ctgaggacac agccatgtat    660

tactgtacaa gggggtcgcc ctggggccaa gggactctgg tcactgtctc tgcaattgaa    720

gttatgtatc ctcctcctta cctagacaat gagaagagca atggaaccat tatccatgtg    780

aaagggaaac acctttgtcc aagtccccta tttcccggac cttctaagcc cttttgggtg    840

ctggtggtgg ttgggggagt cctggcttgc tatagcttgc tagtaacagt ggcctttatt    900

attttctggg tgaaacgggg cagaaagaaa ctcctgtata tattcaaaca accatttatg    960

agaccagtac aaactactca agaggaagat ggctgtagct gccgatttcc agaagaagaa   1020

gaaggaggat gtgaactgag agtgaagttc agcaggagcg cagacgcccc cgcgtaccag   1080

cagggccaga accagctcta taacgagctc aatctaggac gaagagagga gtacgatgtt   1140

ttggacaaga gacgtggccg ggaccctgag atggggggaa agccgagaag gaagaaccct   1200

caggaaggcc tgtacaatga actgcagaaa gataagatgg cggaggccta cagtgagatt   1260

gggatgaaag gcgagcgccg gaggggcaag gggcacgatg gcctttacca gggtctcagt   1320

acagccacca aggacaccta cgacgccctt cacatgcagg ccctgccccc tcgcggatct   1380

ggcgccacca acttctctct gctgaagcag gccggcgacg tggaggagaa cccaggccca   1440

atggtgagca agggcgagga gctgttcacc ggggtggtgc ccatcctggt cgagctggac   1500

ggcgacgtaa acggccacaa gttcagcgtg tccggcgagg gcgagggcga tgccacctac   1560

ggcaagctga ccctgaagtt catctgcacc accggcaagc tgcccgtgcc ctggcccacc   1620

ctcgtgacca ccctgaccta cggcgtgcag tgcttcagcc gctaccccga ccacatgaag   1680

cagcacgact tcttcaagtc cgccatgccc gaaggctacg tccaggagcg caccatcttc   1740

ttcaaggacg acggcaacta caagacccgc gccgaggtga agttcgaggg cgacaccctg   1800

gtgaaccgca tcgagctgaa gggcatcgac ttcaaggagg acggcaacat cctggggcac   1860

aagctggagt acaactacaa cagccacaac gtctatatca tggccgacaa gcagaagaac   1920

ggcatcaagg tgaacttcaa gatccgccac aacatcgagg acggcagcgt gcagctcgcc   1980

gaccactacc agcagaacac ccccatcggc gacggccccg tgctgctgcc cgacaaccac   2040

tacctgagca cccagtccgc cctgagcaaa gaccccaacg agaagcgcga tcacatggtc   2100

ctgctggagt tcgtgaccgc cgccgggatc actctcggca tggacgagct gtacaagtaa   2160
```

<210> SEQ ID NO 91
<211> LENGTH: 2187
<212> TYPE: DNA
<213> ORGANISM: Artificial Sequence
<220> FEATURE:
<223> OTHER INFORMATION: Synthetic

<400> SEQUENCE: 91

```
gaggtgaagc tgcagcaatc aggggctgac ctggcaacac ctggggcttc agtgaagttg     60

tcctgcaagg cttctggcta tacctttagt acctactgga tgcagtgggt aaaacagagg    120

cctggacagg gtctggaatg gattgggact atttatcctg gagatggtga tactaggtac    180

actcagaagt tcaagggcaa ggccacattg actgcagata aatcctccag tacagcccac    240

atgcaactca gcagcttggc atctgaggac tctgcggtct attattgtgc aagaggggga    300

ctctattatg gttacgacat tgcttactgg ggccaaggga ctctggtcac tgtctctgca    360

ggtggcggtg gctcgggcgg tggtgggtcg ggtggcggcg gatctgatat tttgatgacc    420

caaactccac tctccctgcc tgtcagtctt ggagatcaag cctccatctc ttgcagatct    480

agtcagagca ttgtacatag taatggaaac acctatttag aatggtacct gcagaaacca    540
```

```
ggccagtctc caaagcccct gataaagaaa gtctccaacc gattttctgg ggtcccagac    600

aggttcagtg gcagtggatc agggacagaa ttcacactca agatcagcag agtggaggct    660

gaggatctgg gagtttatta ctgctttcaa ggttcacatg ttccattcac gttcggctcg    720

gggacaaagt tggaaataaa aattgaagtt atgtatcctc ctccttacct agacaatgag    780

aagagcaatg gaaccattat ccatgtgaaa gggaaacacc tttgtccaag tcccctattt    840

cccggacctt ctaagccctt ttgggtgctg gtggtggttg gggggagtcct ggcttgctat    900

agcttgctag taacagtggc ctttattatt ttctgggtga aacggggcag aaagaaactc    960

ctgtatatat tcaaacaacc atttatgaga ccagtacaaa ctactcaaga ggaagatggc   1020

tgtagctgcc gatttccaga agaagaagaa ggaggatgtg aactgagagt gaagttcagc   1080

aggagcgcag acgcccccgc gtaccagcag ggccagaacc agctctataa cgagctcaat   1140

ctaggacgaa gagaggagta cgatgttttg gacaagagac gtggccggga ccctgagatg   1200

gggggaaagc cgagaaggaa gaaccctcag gaaggcctgt acaatgaact gcagaaagat   1260

aagatggcgg aggcctacag tgagattggg atgaaaggcg agcgccggag gggcaagggg   1320

cacgatggcc tttaccaggg tctcagtaca gccaccaagg acacctacga cgcccttcac   1380

atgcaggccc tgccccctcg cggatctggc gccaccaact tctctctgct gaagcaggcc   1440

ggcgacgtgg aggagaaccc aggcccaatg gtgagcaagg gcgaggagct gttcaccggg   1500

gtggtgccca tcctggtcga gctggacggc gacgtaaacg gccacaagtt cagcgtgtcc   1560

ggcgagggcg agggcgatgc cacctacggc aagctgaccc tgaagttcat ctgcaccacc   1620

ggcaagctgc ccgtgccctg gcccaccctc gtgaccaccc tgacctacgg cgtgcagtgc   1680

ttcagccgct accccgacca catgaagcag cacgacttct tcaagtccgc catgcccgaa   1740

ggctacgtcc aggagcgcac catcttcttc aaggacgacg gcaactacaa gacccgcgcc   1800

gaggtgaagt tcgagggcga caccctggtg aaccgcatcg agctgaaggg catcgacttc   1860

aaggaggacg gcaacatcct ggggcacaag ctggagtaca actacaacag ccacaacgtc   1920

tatatcatgg ccgacaagca gaagaacggc atcaaggtga acttcaagat ccgccacaac   1980

atcgaggacg gcagcgtgca gctcgccgac cactaccagc agaacacccc catcggcgac   2040

ggccccgtgc tgctgcccga caaccactac ctgagcaccc agtccgccct gagcaaagac   2100

cccaacgaga agcgcgatca catggtcctg ctggagttcg tgaccgccgc cgggatcact   2160

ctcggcatgg acgagctgta caagtaa                                       2187
```

<210> SEQ ID NO 92
<211> LENGTH: 2187
<212> TYPE: DNA
<213> ORGANISM: Artificial Sequence
<220> FEATURE:
<223> OTHER INFORMATION: Synthetic

<400> SEQUENCE: 92

```
gatattttga tgacccaaac tccactctcc ctgcctgtca gtcttggaga tcaagcctcc     60

atctcttgca gatctagtca gagcattgta catagtaatg gaaacaccta tttagaatgg    120

tacctgcaga aaccaggcca gtctccaaag cccctgataa agaaagtctc caaccgattt    180

tctggggtcc cagacaggtt cagtggcagt ggatcaggga cagaattcac actcaagatc    240

agcagagtgg aggctgagga tctgggagtt tattactgct ttcaaggttc acatgttcca    300

ttcacgttcg gctcggggac aaagttggaa ataaaaggtg gcggtggctc gggcggtggt    360
```

gggtcgggtg gcggcggatc tgaggtgaag ctgcagcaat caggggctga cctggcaaca 420
cctggggctt cagtgaagtt gtcctgcaag gcttctggct atacctttag tacctactgg 480
atgcagtggg taaaacagag gcctggacag ggtctggaat ggattgggac tatttatcct 540
ggagatggtg atactaggta cactcagaag ttcaagggca aggccacatt gactgcagat 600
aaatcctcca gtacagccca catgcaactc agcagcttgg catctgagga ctctgcggtc 660
tattattgtg caagaggggg actctattat ggttacgaca ttgcttactg gggccaaggg 720
actctggtca ctgtctctgc aattgaagtt atgtatcctc ctccttacct agacaatgag 780
aagagcaatg gaaccattat ccatgtgaaa gggaaacacc tttgtccaag tcccctattt 840
cccggacctt ctaagccctt ttgggtgctg gtggtggttg gggggagtcct ggcttgctat 900 agcttgctag taacagtggc ctttattatt ttctgggtga aacggggcag aaagaaactc 960
ctgtatatat tcaaacaacc atttatgaga ccagtacaaa ctactcaaga ggaagatggc 1020
tgtagctgcc gatttccaga agaagaagaa ggaggatgtg aactgagagt gaagttcagc 1080
aggagcgcag acgcccccgc gtaccagcag ggccagaacc agctctataa cgagctcaat 1140
ctaggacgaa gagaggagta cgatgttttg gacaagagac gtggccggga ccctgagatg 1200
gggggaaagc cgagaaggaa gaaccctcag gaaggcctgt acaatgaact gcagaaagat 1260
aagatggcgg aggcctacag tgagattggg atgaaaggcg agcgccggag gggcaagggg 1320
cacgatggcc tttaccaggg tctcagtaca gccaccaagg acacctacga cgcccttcac 1380
atgcaggccc tgccccctcg cggatctggc gccaccaact tctctctgct gaagcaggcc 1440
ggcgacgtgg aggagaaccc aggcccaatg gtgagcaagg gcgaggagct gttcaccggg 1500
gtggtgccca tcctggtcga gctggacggc gacgtaaacg gccacaagtt cagcgtgtcc 1560
ggcgagggcg agggcgatgc cacctacggc aagctgaccc tgaagttcat ctgcaccacc 1620
ggcaagctgc ccgtgccctg gcccaccctc gtgaccaccc tgacctacgg cgtgcagtgc 1680
ttcagccgct accccgacca catgaagcag cacgacttct tcaagtccgc catgcccgaa 1740
ggctacgtcc aggagcgcac catcttcttc aaggacgacg gcaactacaa gacccgcgcc 1800
gaggtgaagt tcgagggcga caccctggtg aaccgcatcg agctgaaggg catcgacttc 1860
aaggaggacg gcaacatcct ggggcacaag ctggagtaca actacaacag ccacaacgtc 1920
tatatcatgg ccgacaagca gaagaacggc atcaaggtga acttcaagat ccgccacaac 1980
atcgaggacg gcagcgtgca gctcgccgac cactaccagc agaacacccc catcggcgac 2040
ggccccgtgc tgctgcccga caaccactac ctgagcaccc agtccgccct gagcaaagac 2100
cccaacgaga agcgcgatca catggtcctg ctggagttcg tgaccgccgc cgggatcact 2160
ctcggcatgg acgagctgta caagtaa 2187

<210> SEQ ID NO 93
<211> LENGTH: 2172
<212> TYPE: DNA
<213> ORGANISM: Artificial Sequence
<220> FEATURE:
<223> OTHER INFORMATION: Synthetic

<400> SEQUENCE: 93
gaggtgaagc tggtggagtc tggaggaggc ttggtccagc cgggggggtc tctgagactc 60
tcctgttcaa tttctggatt caccttcact gattactaca tgaactgggt ccgccagtct 120
ccaggaaagg cacttgagtg gttgggtttt attagaaaca aagttaatgg tgacacaaca 180
gaatatagtg catctgtgaa gggtcggttc accatctcca gagatatttc ccagagcatc 240

```
ctctatcttc aaatgaacac cctgagaact gaggacagtg ccacttatta ctgtgcgaga    300

gataagggaa tagcgtacta ctttgactat tggggccaag gcaccactct cacagtctcc    360

tcaggtggcg gtggctcggg cggtggtggg tcgggtggcg gcggatctca aattgttctc    420

tcccagtctc cagcaatcct gtttgcatct ccaggggaga aggtcacaat gacttgtagg    480

gccagctcaa gtgtaagtta cattcactgg taccagcaga agccaggatc ctcccccaaa    540

ccctggattc atggcacatc caacctggct tctggagtcc ctgctcgctt cagtggcagt    600

gggtctggga cctcttactc tctcacaatc agcagaatgg aggctgaaga tgccgccaca    660

tattactgcc agcagtggag tagtaattta tccacgttcg gaggggggac caagctggaa    720

ataaaaattg aagttatgta tcctcctcct tacctagaca atgagaagag caatggaacc    780

attatccatg tgaaagggaa acacctttgt ccaagtcccc tatttcccgg accttctaag    840

cccttttggg tgctggtggt ggttggggga gtcctggctt gctatagctt gctagtaaca    900

gtggccttta ttattttctg ggtgaaacgg ggcagaaaga aactcctgta tatattcaaa    960

caaccattta tgagaccagt acaaactact caagaggaag atggctgtag ctgccgattt   1020

ccagaagaag aagaaggagg atgtgaactg agagtgaagt tcagcaggag cgcagacgcc   1080

cccgcgtacc agcagggcca gaaccagctc tataacgagc tcaatctagg acgaagagag   1140

gagtacgatg ttttggacaa gagacgtggc cgggaccctg agatgggggg aaagccgaga   1200

aggaagaacc ctcaggaagg cctgtacaat gaactgcaga aagataagat ggcggaggcc   1260

tacagtgaga ttgggatgaa aggcgagcgc cggaggggca aggggcacga tggcctttac   1320

cagggtctca gtacagccac caaggacacc tacgacgccc ttcacatgca ggccctgccc   1380

cctcgcggat ctggcgccac caacttctct ctgctgaagc aggccggcga cgtggaggag   1440

aacccaggcc caatggtgag caagggcgag gagctgttca ccggggtggt gcccatcctg   1500

gtcgagctgg acggcgacgt aaacggccac aagttcagcg tgtccggcga gggcgagggc   1560

gatgccacct acggcaagct gaccctgaag ttcatctgca ccaccggcaa gctgcccgtg   1620

ccctggccca ccctcgtgac caccctgacc tacggcgtgc agtgcttcag ccgctacccc   1680

gaccacatga agcagcacga cttcttcaag tccgccatgc ccgaaggcta cgtccaggag   1740

cgcaccatct tcttcaagga cgacggcaac tacaagaccc gcgccgaggt gaagttcgag   1800

ggcgacaccc tggtgaaccg catcgagctg aagggcatcg acttcaagga ggacggcaac   1860

atcctggggc acaagctgga gtacaactac aacagccaca acgtctatat catggccgac   1920

aagcagaaga acggcatcaa ggtgaacttc aagatccgcc acaacatcga ggacggcagc   1980

gtgcagctcg ccgaccacta ccagcagaac acccccatcg gcgacggccc cgtgctgctg   2040

cccgacaacc actacctgag cacccagtcc gccctgagca aagaccccaa cgagaagcgc   2100

gatcacatgg tcctgctgga gttcgtgacc gccgccggga tcactctcgg catggacgag   2160

ctgtacaagt aa                                                       2172
```

<210> SEQ ID NO 94
<211> LENGTH: 2172
<212> TYPE: DNA
<213> ORGANISM: Artificial Sequence
<220> FEATURE:
<223> OTHER INFORMATION: Synthetic

<400> SEQUENCE: 94

```
caaattgttc tctcccagtc tccagcaatc ctgtttgcat ctccagggga gaaggtcaca     60
```

```
atgacttgta gggccagctc aagtgtaagt tacattcact ggtaccagca gaagccagga    120
tcctccccca aaccctggat tcatggcaca tccaacctgg cttctggagt ccctgctcgc    180
ttcagtggca gtgggtctgg gacctcttac tctctcacaa tcagcagaat ggaggctgaa    240
gatgccgcca catattactg ccagcagtgg agtagtaatt tatccacgtt cggagggggg    300
accaagctgg aaataaaagg tggcggtggc tcgggcggtg gtgggtcggg tggcggcgga    360
tctgaggtga agctggtgga gtctggagga ggcttggtcc agccgggggg gtctctgaga    420
ctctcctgtt caatttctgg attcaccttc actgattact acatgaactg ggtccgccag    480
tctccaggaa aggcacttga gtggttgggt tttattagaa acaaagttaa tggtgacaca    540
acagaatata gtgcatctgt gaagggtcgg ttcaccatct ccagagatat ttcccagagc    600
atcctctatc ttcaaatgaa caccctgaga actgaggaca gtgccactta ttactgtgcg    660
agagataagg gaatagcgta ctactttgac tattggggcc aaggcaccac tctcacagtc    720
tcctcaattg aagttatgta tcctcctcct tacctagaca atgagaagag caatggaacc    780
attatccatg tgaaagggaa acacctttgt ccaagtcccc tatttcccgg accttctaag    840
cccttttggg tgctggtggt ggttggggga gtcctggctt gctatagctt gctagtaaca    900
gtggccttta ttattttctg ggtgaaacgg ggcagaaaga aactcctgta tatattcaaa    960
caaccattta tgagaccagt acaaactact caagaggaag atggctgtag ctgccgattt   1020
ccagaagaag aagaaggagg atgtgaactg agagtgaagt tcagcaggag cgcagacgcc   1080
cccgcgtacc agcagggcca gaaccagctc tataacgagc tcaatctagg acgaagagag   1140
gagtacgatg ttttggacaa gagacgtggc cgggaccctg agatgggggg aaagccgaga   1200
aggaagaacc ctcaggaagg cctgtacaat gaactgcaga aagataagat ggcggaggcc   1260
tacagtgaga ttgggatgaa aggcgagcgc cggaggggca aggggcacga tggcctttac   1320
cagggtctca gtacagccac caaggacacc tacgacgccc ttcacatgca ggccctgccc   1380
cctcgcggat ctggcgccac caacttctct ctgctgaagc aggccggcga cgtggaggag   1440
aacccaggcc caatggtgag caagggcgag gagctgttca ccggggtggt gcccatcctg   1500
gtcgagctgg acggcgacgt aaacggccac aagttcagcg tgtccggcga gggcgagggc   1560
gatgccacct acggcaagct gaccctgaag ttcatctgca ccaccggcaa gctgcccgtg   1620
ccctggccca ccctcgtgac caccctgacc tacggcgtgc agtgcttcag ccgctacccc   1680
gaccacatga agcagcacga cttcttcaag tccgccatgc ccgaaggcta cgtccaggag   1740
cgcaccatct tcttcaagga cgacggcaac tacaagaccc gcgccgaggt gaagttcgag   1800
ggcgacaccc tggtgaaccg catcgagctg aagggcatcg acttcaagga ggacggcaac   1860
atcctggggc acaagctgga gtacaactac aacagccaca acgtctatat catggccgac   1920
aagcagaaga acggcatcaa ggtgaacttc aagatccgcc acaacatcga ggacggcagc   1980
gtgcagctcg ccgaccacta ccagcagaac acccccatcg gcgacggccc cgtgctgctg   2040
cccgacaacc actacctgag cacccagtcc gccctgagca aagaccccaa cgagaagcgc   2100
gatcacatgg tcctgctgga gttcgtgacc gccgccggga tcactctcgg catggacgag   2160
ctgtacaagt aa                                                       2172
```

<210> SEQ ID NO 95
<211> LENGTH: 2157
<212> TYPE: DNA
<213> ORGANISM: Artificial Sequence
<220> FEATURE:
<223> OTHER INFORMATION: Synthetic

<400> SEQUENCE: 95

```
caggtgcagc tgaaggagtc aggacctggc ctggtggcgc cctcacagaa cctgtccatc     60
acatgcactg tctctgggtt ctcattaacc agctatgcta taaactgggt tcgccagcca    120
ccaggaaagg gtctggagtg gcttggaata atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtgcctc gggggtgtac    300
tactttgact actggggcct aggcaccact ctcacagtct cctcaggtgg cggtggctcg    360
ggcggtggtg ggtcgggtgg cggcggatct gacattgtga tgacccagtc tcacaaattc    420
atgtccacat cagtaggaga cagggtcagc atcacctgca aggccagtca ggatgtgact    480
actgctgtag cctggtatca acaaaaacca gggcaatctc ctaaagtact gatttctgg     540
gcatccaccc ggcacactgg agtccctgat cgcttcacag gcagtggatc tgggacagat    600
tatactctca ccatcagcag tgtgcaggct gaagacctgg cactttatta ctgtcagcaa    660
tattatagaa ctcctcggac gttcggtgga ggcaccaaac tggaaatcaa aattgaagtt    720
atgtatcctc ctccttacct agacaatgag aagagcaatg gaaccattat ccatgtgaaa    780
gggaaacacc tttgtccaag tcccctattt cccggacctt ctaagccctt ttgggtgctg    840
gtggtggttg gggagtcct ggcttgctat agcttgctag taacagtggc ctttattatt     900
ttctgggtga aacggggcag aaagaaactc ctgtatatat tcaaacaacc atttatgaga    960
ccagtacaaa ctactcaaga ggaagatggc tgtagctgcc gatttccaga agaagaagaa   1020
ggaggatgtg aactgagagt gaagttcagc aggagcgcag acgcccccgc gtaccagcag   1080
ggccagaacc agctctataa cgagctcaat ctaggacgaa gagaggagta cgatgttttg   1140
gacaagagac gtggccggga ccctgagatg gggggaaagc cgagaaggaa gaaccctcag   1200
gaaggcctgt acaatgaact gcagaaagat aagatggcgg aggcctacag tgagattggg   1260
atgaaaggcg agcgccggag gggcaagggg cacgatggcc tttaccaggg tctcagtaca   1320
gccaccaagg acacctacga cgcccttcac atgcaggccc tgccccctcg cggatctggc   1380
gccaccaact tctctctgct gaagcaggcc ggcgacgtgg aggagaaccc aggcccaatg   1440
gtgagcaagg gcgaggagct gttcaccggg gtggtgccca tcctggtcga gctggacggc   1500
gacgtaaacg gccacaagtt cagcgtgtcc ggcgagggcg agggcgatgc cacctacggc   1560
aagctgaccc tgaagttcat ctgcaccacc ggcaagctgc ccgtgccctg gcccaccctc   1620
gtgaccaccc tgacctacgg cgtgcagtgc ttcagccgct accccgacca catgaagcag   1680
cacgacttct tcaagtccgc catgcccgaa ggctacgtcc aggagcgcac catcttcttc   1740
aaggacgacg gcaactacaa gacccgcgcc gaggtgaagt tcgagggcga caccctggtg   1800
aaccgcatcg agctgaaggg catcgacttc aaggaggacg gcaacatcct ggggcacaag   1860
ctggagtaca actacaacag ccacaacgtc tatatcatgg ccgacaagca gaagaacggc   1920
atcaaggtga acttcaagat ccgccacaac atcgaggacg gcagcgtgca gctcgccgac   1980
cactaccagc agaacacccc catcggcgac ggccccgtgc tgctgcccga caaccactac   2040
ctgagcaccc agtccgccct gagcaaagac cccaacgaga agcgcgatca catggtcctg   2100
ctggagttcg tgaccgccgc cgggatcact ctcggcatgg acgagctgta caagtaa      2157
```

<210> SEQ ID NO 96
<211> LENGTH: 2157
<212> TYPE: DNA

<213> ORGANISM: Artificial Sequence
<220> FEATURE:
<223> OTHER INFORMATION: Synthetic

<400> SEQUENCE: 96

```
gacattgtga tgacccagtc tcacaaattc atgtccacat cagtaggaga cagggtcagc      60
atcacctgca aggccagtca ggatgtgact actgctgtag cctggtatca acaaaaacca     120
gggcaatctc ctaaagtact gattttctgg gcatccaccc ggcacactgg agtccctgat     180
cgcttcacag gcagtggatc tgggacagat tatactctca ccatcagcag tgtgcaggct     240
gaagacctgg cactttatta ctgtcagcaa tattatagaa ctcctcggac gttcggtgga     300
ggcaccaaac tggaaatcaa aggtggcggt ggctcgggcg gtggtgggtc gggtggcggc     360
ggatctcagg tgcagctgaa ggagtcagga cctggcctgg tggcgccctc acagaacctg     420
tccatcacat gcactgtctc tgggttctca ttaaccagct atgctataaa ctgggttcgc     480
cagccaccag gaaagggtct ggagtggctt ggaataatat ggactggtgg aggcacaaat     540
tataattcag ctctcaaatc cagactgagc atcagcaaag acaactccaa gagtcaagtt     600
ttcttaaaaa tgaacagtct gcaaactgat gacacagcca ggtactactg tgcctcgggg     660
gtgtactact ttgactactg gggcctaggc accactctca cagtctcctc aattgaagtt     720
atgtatcctc ctccttacct agacaatgag aagagcaatg gaaccattat ccatgtgaaa     780
gggaaacacc tttgtccaag tcccctattt cccggacctt ctaagccctt ttgggtgctg     840
gtggtggttg gggagtcct ggcttgctat agcttgctag taacagtggc ctttattatt      900
ttctgggtga aacggggcag aaagaaactc ctgtatatat tcaaacaacc atttatgaga     960
ccagtacaaa ctactcaaga ggaagatggc tgtagctgcc gatttccaga agaagaagaa    1020
ggaggatgtg aactgagagt gaagttcagc aggagcgcag acgcccccgc gtaccagcag    1080
ggccagaacc agctctataa cgagctcaat ctaggacgaa gagaggagta cgatgttttg    1140
gacaagagac gtggccggga ccctgagatg gggggaaagc cgagaaggaa gaaccctcag    1200
gaaggcctgt acaatgaact gcagaaagat aagatggcgg aggcctacag tgagattggg    1260
atgaaaggcg agcgccggag gggcaagggg cacgatggcc tttaccaggg tctcagtaca    1320
gccaccaagg acacctacga cgcccttcac atgcaggccc tgccccctcg cggatctggc    1380
gccaccaact tctctctgct gaagcaggcc ggcgacgtgg aggagaaccc aggcccaatg    1440
gtgagcaagg gcgaggagct gttcaccggg gtggtgccca tcctggtcga gctggacggc    1500
gacgtaaacg gccacaagtt cagcgtgtcc ggcgagggcg agggcgatgc cacctacggc    1560
aagctgaccc tgaagttcat ctgcaccacc ggcaagctgc ccgtgccctg gcccaccctc    1620
gtgaccaccc tgacctacgg cgtgcagtgc ttcagccgct accccgacca catgaagcag    1680
cacgacttct tcaagtccgc catgcccgaa ggctacgtcc aggagcgcac catcttcttc    1740
aaggacgacg gcaactacaa gacccgcgcc gaggtgaagt tcgagggcga caccctggtg    1800
aaccgcatcg agctgaaggg catcgacttc aaggaggacg gcaacatcct ggggcacaag    1860
ctggagtaca actacaacag ccacaacgtc tatatcatgg ccgacaagca gaagaacggc    1920
atcaaggtga acttcaagat ccgccacaac atcgaggacg gcagcgtgca gctcgccgac    1980
cactaccagc agaacacccc catcggcgac ggccccgtgc tgctgcccga caaccactac    2040
ctgagcaccc agtccgccct gagcaaagac cccaacgaga agcgcgatca catggtcctg    2100
ctggagttcg tgaccgccgc cgggatcact ctcggcatgg acgagctgta caagtaa       2157
```

<210> SEQ ID NO 97
<211> LENGTH: 2175
<212> TYPE: DNA
<213> ORGANISM: Artificial Sequence
<220> FEATURE:
<223> OTHER INFORMATION: Synthetic

<400> SEQUENCE: 97

```
gaggtgaagc tgcaggaatc tggagctgag ctggtgaagc ctggggcttc agtgaagatc     60
tcctgcaagg cttctggcta cacattcaat gactacaaca tggactatct gaagcagagc    120
catggaaaga gccttgagtg gattggagat attaatccta actatgatag cactatctac    180
aaccagaagt tcaagggcaa ggccacattg actgtagaca agtcctccag cacagcctac    240
atggagctcc gcagcctgac atctgaggac tctgcagtct attactgtgc aagacgagac    300
tacgatggta ggagggggc ctggttttct tactggggcc aagggactct ggtcactgtc     360
tctgcaggtg gcggtggctc gggcggtggt gggtcgggtg gcggcggatc tcaaattgtt    420
ctcacccagt ctccagcact catgtctgca tctccagggg agaaggtcac cgtgacctgc    480
actgccagct caagtgtaag ttacatgtac tggtaccagc agaagccaag atcctccccc    540
aaaccctgga tttatctcac atccaacctg gcttctggag tccctactcg cttcagtggc    600
agtgggtctg ggacctctta ttctctcaca atcagcagca tggaggctga agatgctgcc    660
acttattact gccagcagtg ggatagtaac ccgctcacgt tcggtgctgg gaccaaactg    720
gagctgaaaa ttgaagttat gtatcctcct ccttacctag acaatgagaa gagcaatgga    780
accattatcc atgtgaaagg gaaacacctt tgtccaagtc ccctatttcc cggaccttct    840
aagccctttt gggtgctggt ggtggttggg ggagtcctgg cttgctatag cttgctagta    900
acagtggcct ttattatttt ctgggtgaaa cggggcagaa agaaactcct gtatatattc    960
aaacaaccat ttatgagacc agtacaaact actcaagagg aagatggctg tagctgccga   1020
tttccagaag aagaagaagg aggatgtgaa ctgagagtga agttcagcag gagcgcagac   1080
gcccccgcgt accagcaggg ccagaaccag ctctataacg agctcaatct aggacgaaga   1140
gaggagtacg atgttttgga caagagacgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg gcaaggggca cgatggcctt   1320
taccagggtc tcagtacagc caccaaggac acctacgacg cccttcacat gcaggccctg   1380
ccccctcgcg gatctggcgc caccaacttc tctctgctga agcaggccgg cgacgtggag   1440
gagaacccag gcccaatggt gagcaagggc gaggagctgt tcaccggggt ggtgcccatc   1500
ctggtcgagc tggacggcga cgtaaacggc cacaagttca gcgtgtccgg cgagggcgag   1560
ggcgatgcca cctacggcaa gctgaccctg aagttcatct gcaccaccgg caagctgccc   1620
gtgccctggc ccaccctcgt gaccaccctg acctacggcg tgcagtgctt cagccgctac   1680
cccgaccaca tgaagcagca cgacttcttc aagtccgcca tgcccgaagg ctacgtccag   1740
gagcgcacca tcttcttcaa ggacgacggc aactacaaga cccgcgccga ggtgaagttc   1800
gagggcgaca ccctggtgaa ccgcatcgag ctgaagggca tcgacttcaa ggaggacggc   1860
aacatcctgg ggcacaagct ggagtacaac tacaacagcc acaacgtcta tatcatggcc   1920
gacaagcaga agaacggcat caaggtgaac ttcaagatcc gccacaacat cgaggacggc   1980
agcgtgcagc tcgccgacca ctaccagcag aacaccccca tcggcgacgg ccccgtgctg   2040
ctgcccgaca accactacct gagcacccag tccgccctga gcaaagaccc caacgagaag   2100
```

```
cgcgatcaca tggtcctgct ggagttcgtg accgccgccg ggatcactct cggcatggac   2160

gagctgtaca agtaa                                                   2175


<210> SEQ ID NO 98
<211> LENGTH: 2175
<212> TYPE: DNA
<213> ORGANISM: Artificial Sequence
<220> FEATURE:
<223> OTHER INFORMATION: Synthetic

<400> SEQUENCE: 98

caaattgttc tcacccagtc tccagcactc atgtctgcat ctccagggga gaaggtcacc     60

gtgacctgca ctgccagctc aagtgtaagt tacatgtact ggtaccagca gaagccaaga    120

tcctccccca aaccctggat ttatctcaca tccaacctgg cttctggagt ccctactcgc    180

ttcagtggca gtgggtctgg gacctcttat tctctcacaa tcagcagcat ggaggctgaa    240

gatgctgcca cttattactg ccagcagtgg gatagtaacc cgctcacgtt cggtgctggg    300

accaaactgg agctgaaagg tggcggtggc tcgggcggtg gtgggtcggg tggcggcgga    360

tctgaggtga agctgcagga atctggagct gagctggtga agcctggggc ttcagtgaag    420

atctcctgca aggcttctgg ctacacattc aatgactaca acatggacta tctgaagcag    480

agccatggaa agagccttga gtggattgga gatattaatc ctaactatga tagcactatc    540

tacaaccaga agttcaaggg caaggccaca ttgactgtag acaagtcctc cagcacagcc    600

tacatggagc tccgcagcct gacatctgag gactctgcag tctattactg tgcaagacga    660

gactacgatg gtaggagggg ggcctggttt tcttactggg gccaagggac tctggtcact    720

gtctctgcaa ttgaagttat gtatcctcct ccttacctag acaatgagaa gagcaatgga    780

accattatcc atgtgaaagg gaaacacctt tgtccaagtc ccctatttcc cggaccttct    840

aagccctttt gggtgctggt ggtggttggg ggagtcctgg cttgctatag cttgctagta    900

acagtggcct ttattatttt ctgggtgaaa cggggcagaa agaaactcct gtatatattc    960

aaacaaccat ttatgagacc agtacaaact actcaagagg aagatggctg tagctgccga   1020

tttccagaag aagaagaagg aggatgtgaa ctgagagtga agttcagcag gagcgcagac   1080

gcccccgcgt accagcaggg ccagaaccag ctctataacg agctcaatct aggacgaaga   1140

gaggagtacg atgttttgga caagagacgt ggccgggacc ctgagatggg gggaaagccg   1200

agaaggaaga accctcagga aggcctgtac aatgaactgc agaaagataa gatggcggag   1260

gcctacagtg agattgggat gaaaggcgag cgccggaggg gcaaggggca cgatggcctt   1320

taccagggtc tcagtacagc caccaaggac acctacgacg cccttcacat gcaggccctg   1380

ccccctcgcg gatctggcgc caccaacttc tctctgctga agcaggccgg cgacgtggag   1440

gagaacccag gcccaatggt gagcaagggc gaggagctgt tcaccggggt ggtgcccatc   1500

ctggtcgagc tggacggcga cgtaaacggc cacaagttca gcgtgtccgg cgagggcgag   1560

ggcgatgcca cctacggcaa gctgaccctg aagttcatct gcaccaccgg caagctgccc   1620

gtgccctggc ccaccctcgt gaccaccctg acctacggcg tgcagtgctt cagccgctac   1680

cccgaccaca tgaagcagca cgacttcttc aagtccgcca tgcccgaagg ctacgtccag   1740

gagcgcacca tcttcttcaa ggacgacggc aactacaaga cccgcgccga ggtgaagttc   1800

gagggcgaca ccctggtgaa ccgcatcgag ctgaagggca tcgacttcaa ggaggacggc   1860

aacatcctgg ggcacaagct ggagtacaac tacaacagcc acaacgtcta tatcatggcc   1920

gacaagcaga agaacggcat caaggtgaac ttcaagatcc gccacaacat cgaggacggc   1980
```

```
agcgtgcagc tcgccgacca ctaccagcag aacaccccca tcggcgacgg ccccgtgctg   2040

ctgcccgaca accactacct gagcacccag tccgccctga gcaaagaccc caacgagaag   2100

cgcgatcaca tggtcctgct ggagttcgtg accgccgccg ggatcactct cggcatggac   2160

gagctgtaca agtaa                                                    2175
```

<210> SEQ ID NO 99
<211> LENGTH: 1377
<212> TYPE: DNA
<213> ORGANISM: Artificial Sequence
<220> FEATURE:
<223> OTHER INFORMATION: Synthetic

<400> SEQUENCE: 99

```
ggtgtccagt gtgacgtgaa gttggtggag tctgggggag gcttagtgaa gcctggaggg     60

tccctgaaac tctcctgtgc agcctctgga ttcactttca gtagatacac catgtcttgg    120

gttcgccaga ctccggagaa gaggctggag tgggtcgcaa ccattagtaa tagtggtagt    180

tatacctact atcgagacag tgtgaagggc cgattcacca tctccagaga caatgccaag    240

aacaccctgt acctgcaaat gagcagtctg aagtctgagg acacagccat gtattactgt    300

acaagggggt cgccctgggg ccaagggact ctggtcactg tctctgcagg tggcggtggc    360

tcgggcggtg gtgggtcggg tggcggcgga tctgacatcc agatgactca gtctccagat    420

tcactgtctg catctgtggg agaaactgtc accatcacat gtggagcaag tgagaacatt    480

tacggtgctt taaattggta tcagcggaaa cagggaaaat ctcctcagct cctgatctat    540

ggtgcaacca agttggcaga tggcatgtca tcgaggttca gtggcagtgg atctaataga    600

cagtattctc tcaagatcag tagcctgcat cctgacgatg ttgcaacgta ttactgtcaa    660

aatgtgttaa gtaagccgta cgcgttcgga ggggggacca aactggaaat aaaaattgaa    720

gttatgtatc ctcctcctta cctagacaat gagaagagca atggaaccat tatccatgtg    780

aaagggaaac acctttgtcc aagtccccta tttcccggac cttctaagcc cttttgggtg    840

ctggtggtgg ttgggggagt cctggcttgc tatagcttgc tagtaacagt ggcctttatt    900

attttctggg tgaaacgggg cagaaagaaa ctcctgtata tattcaaaca accatttatg    960

agaccagtac aaactactca agaggaagat ggctgtagct gccgatttcc agaagaagaa   1020

gaaggaggat gtgaactgag agtgaagttc agcaggagcg cagacgcccc cgcgtaccag   1080

cagggccaga accagctcta taacgagctc aatctaggac gaagagagga gtacgatgtt   1140

ttggacaaga gacgtggccg ggaccctgag atggggggaa agccgagaag gaagaaccct   1200

caggaaggcc tgtacaatga actgcagaaa gataagatgg cggaggccta cagtgagatt   1260

gggatgaaag gcgagcgccg gaggggcaag gggcacgatg gcctttacca gggtctcagt   1320

acagccacca aggacaccta cgacgccctt cacatgcagg ccctgccccc tcgctaa      1377
```

<210> SEQ ID NO 100
<211> LENGTH: 1377
<212> TYPE: DNA
<213> ORGANISM: Artificial Sequence
<220> FEATURE:
<223> OTHER INFORMATION: Synthetic

<400> SEQUENCE: 100

```
gacatccaga tgactcagtc tccagattca ctgtctgcat ctgtgggaga aactgtcacc     60

atcacatgtg gagcaagtga gaacatttac ggtgctttaa attggtatca gcggaaacag    120
```

```
ggaaaatctc ctcagctcct gatctatggt gcaaccaagt tggcagatgg catgtcatcg    180
aggttcagtg gcagtggatc taatagacag tattctctca agatcagtag cctgcatcct    240
gacgatgttg caacgtatta ctgtcaaaat gtgttaagta agccgtacgc gttcggaggg    300
gggaccaaac tggaaataaa aggtggcggt ggctcgggcg gtggtgggtc gggtggcggc    360
ggatctggtg tccagtgtga cgtgaagttg gtggagtctg gggaggctt agtgaagcct     420
ggagggtccc tgaaactctc ctgtgcagcc tctggattca ctttcagtag atacaccatg    480
tcttgggttc gccagactcc ggagaagagg ctggagtggg tcgcaaccat tagtaatagt    540
ggtagttata cctactatcg agacagtgtg aagggccgat tcaccatctc cagagacaat    600
gccaagaaca ccctgtacct gcaaatgagc agtctgaagt ctgaggacac agccatgtat    660
tactgtacaa gggggtcgcc ctggggccaa gggactctgg tcactgtctc tgcaattgaa    720
gttatgtatc ctcctcctta cctagacaat gagaagagca atggaaccat tatccatgtg    780
aaagggaaac acctttgtcc aagtccccta tttcccggac cttctaagcc cttttgggtg    840
ctggtggtgg ttgggggagt cctggcttgc tatagcttgc tagtaacagt ggcctttatt    900
attttctggg tgaaacgggg cagaaagaaa ctcctgtata tattcaaaca accatttatg    960
agaccagtac aaactactca agaggaagat ggctgtagct gccgatttcc agaagaagaa   1020
gaaggaggat gtgaactgag agtgaagttc agcaggagcg cagacgcccc cgcgtaccag   1080
cagggccaga accagctcta taacgagctc aatctaggac gaagagagga gtacgatgtt   1140
ttggacaaga gacgtggccg ggaccctgag atgggggaa agccgagaag gaagaaccct    1200
caggaaggcc tgtacaatga actgcagaaa gataagatgg cggaggccta cagtgagatt   1260
gggatgaaag gcgagcgccg gaggggcaag gggcacgatg gcctttacca gggtctcagt   1320
acagccacca aggacaccta cgacgccctt cacatgcagg ccctgccccc tcgctaa      1377
```

<210> SEQ ID NO 101
<211> LENGTH: 1404
<212> TYPE: DNA
<213> ORGANISM: Artificial Sequence
<220> FEATURE:
<223> OTHER INFORMATION: Synthetic

<400> SEQUENCE: 101

```
gaggtgaagc tgcagcaatc aggggctgac ctggcaacac ctggggcttc agtgaagttg     60
tcctgcaagg cttctggcta tacctttagt acctactgga tgcagtgggt aaaacagagg    120
cctggacagg gtctggaatg gattgggact atttatcctg gagatggtga tactaggtac    180
actcagaagt tcaagggcaa ggccacattg actgcagata aatcctccag tacagcccac    240
atgcaactca gcagcttggc atctgaggac tctgcggtct attattgtgc aagaggggga    300
ctctattatg gttacgacat tgcttactgg ggccaaggga ctctggtcac tgtctctgca    360
ggtggcggtg gctcgggcgg tggtgggtcg ggtggcggcg gatctgatat tttgatgacc    420
caaactccac tctccctgcc tgtcagtctt ggagatcaag cctccatctc ttgcagatct    480
agtcagagca ttgtacatag taatggaaac acctatttag aatggtacct gcagaaacca    540
ggccagtctc caaagcccct gataaagaaa gtctccaacc gattttctgg ggtcccagac    600
aggttcagtg gcagtggatc agggacagaa ttcacactca agatcagcag agtggaggct    660
gaggatctgg gagtttatta ctgctttcaa ggttcacatg ttccattcac gttcggctcg    720
gggacaaagt tggaaataaa aattgaagtt atgtatcctc ctccttacct agacaatgag    780
aagagcaatg gaaccattat ccatgtgaaa gggaaacacc tttgtccaag tcccctattt    840
```

```
cccggacctt ctaagccctt ttgggtgctg gtggtggttg ggggagtcct ggcttgctat     900

agcttgctag taacagtggc ctttattatt ttctgggtga aacggggcag aaagaaactc     960

ctgtatatat tcaaacaacc atttatgaga ccagtacaaa ctactcaaga ggaagatggc    1020

tgtagctgcc gatttccaga agaagaagaa ggaggatgtg aactgagagt gaagttcagc    1080

aggagcgcag acgcccccgc gtaccagcag ggccagaacc agctctataa cgagctcaat    1140

ctaggacgaa gagaggagta cgatgttttg gacaagagac gtggccggga ccctgagatg    1200

gggggaaagc cgagaaggaa gaaccctcag gaaggcctgt acaatgaact gcagaaagat    1260

aagatggcgg aggcctacag tgagattggg atgaaaggcg agcgccggag gggcaagggg    1320

cacgatggcc tttaccaggg tctcagtaca gccaccaagg acacctacga cgcccttcac    1380

atgcaggccc tgccccctcg ctaa                                           1404
```

<210> SEQ ID NO 102
<211> LENGTH: 1404
<212> TYPE: DNA
<213> ORGANISM: Artificial Sequence
<220> FEATURE:
<223> OTHER INFORMATION: Synthetic

<400> SEQUENCE: 102

```
gatattttga tgacccaaac tccactctcc ctgcctgtca gtcttggaga tcaagcctcc      60

atctcttgca gatctagtca gagcattgta catagtaatg gaaacaccta tttagaatgg     120

tacctgcaga aaccaggcca gtctccaaag cccctgataa agaaagtctc caaccgattt     180

tctggggtcc cagacaggtt cagtggcagt ggatcaggga cagaattcac actcaagatc     240

agcagagtgg aggctgagga tctgggagtt tattactgct ttcaaggttc acatgttcca     300

ttcacgttcg gctcggggac aaagttggaa ataaaaggtg gcggtggctc gggcggtggt     360

gggtcgggtg gcggcggatc tgaggtgaag ctgcagcaat caggggctga cctggcaaca     420

cctggggctt cagtgaagtt gtcctgcaag gcttctggct atacctttag tacctactgg     480

atgcagtggg taaaacagag gcctggacag ggtctggaat ggattgggac tatttatcct     540

ggagatggtg atactaggta cactcagaag ttcaagggca aggccacatt gactgcagat     600

aaatcctcca gtacagccca catgcaactc agcagcttgg catctgagga ctctgcggtc     660

tattattgtg caagaggggg actctattat ggttacgaca ttgcttactg gggccaaggg     720

actctggtca ctgtctctgc aattgaagtt atgtatcctc ctccttacct agacaatgag     780

aagagcaatg gaaccattat ccatgtgaaa gggaaacacc tttgtccaag tcccctattt     840

cccggacctt ctaagccctt ttgggtgctg gtggtggttg ggggagtcct ggcttgctat     900

agcttgctag taacagtggc ctttattatt ttctgggtga aacggggcag aaagaaactc     960

ctgtatatat tcaaacaacc atttatgaga ccagtacaaa ctactcaaga ggaagatggc    1020

tgtagctgcc gatttccaga agaagaagaa ggaggatgtg aactgagagt gaagttcagc    1080

aggagcgcag acgcccccgc gtaccagcag ggccagaacc agctctataa cgagctcaat    1140

ctaggacgaa gagaggagta cgatgttttg gacaagagac gtggccggga ccctgagatg    1200

gggggaaagc cgagaaggaa gaaccctcag gaaggcctgt acaatgaact gcagaaagat    1260

aagatggcgg aggcctacag tgagattggg atgaaaggcg agcgccggag gggcaagggg    1320

cacgatggcc tttaccaggg tctcagtaca gccaccaagg acacctacga cgcccttcac    1380

atgcaggccc tgccccctcg ctaa                                           1404
```

<210> SEQ ID NO 103
<211> LENGTH: 1389
<212> TYPE: DNA
<213> ORGANISM: Artificial Sequence
<220> FEATURE:
<223> OTHER INFORMATION: Synthetic

<400> SEQUENCE: 103

```
gaggtgaagc tggtggagtc tggaggaggc ttggtccagc cggggggtc tctgagactc      60
tcctgttcaa tttctggatt caccttcact gattactaca tgaactgggt ccgccagtct     120
ccaggaaagg cacttgagtg gttgggtttt attagaaaca aagttaatgg tgacacaaca     180
gaatatagtg catctgtgaa gggtcggttc accatctcca gagatatttc ccagagcatc     240
ctctatcttc aaatgaacac cctgagaact gaggacagtg ccacttatta ctgtgcgaga     300
gataagggaa tagcgtacta ctttgactat tggggccaag gcaccactct cacagtctcc     360
tcaggtggcg gtggctcggg cggtggtggg tcgggtggcg gcggatctca aattgttctc     420
tcccagtctc cagcaatcct gtttgcatct ccaggggaga aggtcacaat gacttgtagg     480
gccagctcaa gtgtaagtta cattcactgg taccagcaga agccaggatc ctcccccaaa     540
ccctggattc atggcacatc caacctggct tctggagtcc ctgctcgctt cagtggcagt     600
gggtctggga cctcttactc tctcacaatc agcagaatgg aggctgaaga tgccgccaca     660
tattactgcc agcagtggag tagtaattta tccacgttcg gagggggac caagctggaa      720
ataaaaattg aagttatgta tcctcctcct tacctagaca atgagaagag caatggaacc     780
attatccatg tgaaagggaa acacctttgt ccaagtcccc tatttcccgg accttctaag     840
cccttttggg tgctggtggt ggttggggga gtcctggctt gctatagctt gctagtaaca     900
gtggccttta ttattttctg ggtgaaacgg ggcagaaaga aactcctgta tatattcaaa     960
caaccattta tgagaccagt acaaactact caagaggaag atggctgtag ctgccgattt    1020
ccagaagaag aagaaggagg atgtgaactg agagtgaagt tcagcaggag cgcagacgcc    1080
cccgcgtacc agcagggcca gaaccagctc tataacgagc tcaatctagg acgaagagag    1140
gagtacgatg ttttggacaa gagacgtggc cgggaccctg agatgggggg aaagccgaga    1200
aggaagaacc ctcaggaagg cctgtacaat gaactgcaga aagataagat ggcggaggcc    1260
tacagtgaga ttgggatgaa aggcgagcgc cggaggggca aggggcacga tggcctttac    1320
cagggtctca gtacagccac caaggacacc tacgacgccc ttcacatgca ggccctgccc    1380
cctcgctaa                                                            1389
```

<210> SEQ ID NO 104
<211> LENGTH: 1389
<212> TYPE: DNA
<213> ORGANISM: Artificial Sequence
<220> FEATURE:
<223> OTHER INFORMATION: Synthetic

<400> SEQUENCE: 104

```
caaattgttc tctcccagtc tccagcaatc ctgtttgcat ctccagggga gaaggtcaca      60
atgacttgta gggccagctc aagtgtaagt tacattcact ggtaccagca gaagccagga     120
tcctccccca aaccctggat tcatggcaca tccaacctgg cttctggagt ccctgctcgc     180
ttcagtggca gtgggtctgg gacctcttac tctctcacaa tcagcagaat ggaggctgaa     240
gatgccgcca catattactg ccagcagtgg agtagtaatt tatccacgtt cggagggggg     300
accaagctgg aaataaaagg tggcggtggc tcgggcggtg gtgggtcggg tggcggcgga     360
```

```
tctgaggtga agctggtgga gtctggagga ggcttggtcc agccgggggg gtctctgaga    420
ctctcctgtt caatttctgg attcaccttc actgattact acatgaactg ggtccgccag    480
tctccaggaa aggcacttga gtggttgggt tttattagaa acaaagttaa tggtgacaca    540
acagaatata gtgcatctgt gaagggtcgg ttcaccatct ccagagatat ttcccagagc    600
atcctctatc ttcaaatgaa caccctgaga actgaggaca gtgccactta ttactgtgcg    660
agagataagg gaatagcgta ctactttgac tattggggcc aaggcaccac tctcacagtc    720
tcctcaattg aagttatgta tcctcctcct tacctagaca atgagaagag caatggaacc    780
attatccatg tgaaagggaa acacctttgt ccaagtcccc tatttcccgg accttctaag    840
ccccttttggg tgctggtggt ggttggggga gtcctggctt gctatagctt gctagtaaca    900
gtggccttta ttattttctg ggtgaaacgg ggcagaaaga aactcctgta tatattcaaa    960
caaccattta tgagaccagt acaaactact caagaggaag atggctgtag ctgccgattt   1020
ccagaagaag aagaaggagg atgtgaactg agagtgaagt tcagcaggag cgcagacgcc   1080
cccgcgtacc agcagggcca gaaccagctc tataacgagc tcaatctagg acgaagagag   1140
gagtacgatg ttttggacaa gagacgtggc cgggaccctg agatgggggg aaagccgaga   1200
aggaagaacc ctcaggaagg cctgtacaat gaactgcaga aagataagat ggcggaggcc   1260
tacagtgaga ttgggatgaa aggcgagcgc cggaggggca aggggcacga tggcctttac   1320
cagggtctca gtacagccac caaggacacc tacgacgccc ttcacatgca ggccctgccc   1380
cctcgctaa                                                           1389
```

<210> SEQ ID NO 105
<211> LENGTH: 1374
<212> TYPE: DNA
<213> ORGANISM: Artificial Sequence
<220> FEATURE:
<223> OTHER INFORMATION: Synthetic

<400> SEQUENCE: 105

```
caggtgcagc tgaaggagtc aggacctggc ctggtggcgc cctcacagaa cctgtccatc     60
acatgcactg tctctgggtt ctcattaacc agctatgcta taaactgggt tcgccagcca    120
ccaggaaagg gtctggagtg gcttggaata atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtgcctc gggggtgtac    300
tactttgact actggggcct aggcaccact ctcacagtct cctcaggtgg cggtggctcg    360
ggcggtggtg ggtcgggtgg cggcggatct gacattgtga tgacccagtc tcacaaattc    420
atgtccacat cagtaggaga cagggtcagc atcacctgca aggccagtca ggatgtgact    480
actgctgtag cctggtatca acaaaaacca gggcaatctc ctaaagtact gattttctgg    540
gcatccaccc ggcacactgg agtccctgat cgcttcacag gcagtggatc tgggacagat    600
tatactctca ccatcagcag tgtgcaggct gaagacctgg cactttatta ctgtcagcaa    660
tattatagaa ctcctcggac gttcggtgga ggcaccaaac tggaaatcaa aattgaagtt    720
atgtatcctc ctccttacct agacaatgag aagagcaatg gaaccattat ccatgtgaaa    780
gggaaacacc tttgtccaag tcccctattt cccggacctt ctaagccctt ttgggtgctg    840
gtggtggttg ggggagtcct ggcttgctat agcttgctag taacagtggc ctttattatt    900
ttctgggtga aacggggcag aaagaaactc ctgtatatat tcaaacaacc atttatgaga    960
```

```
ccagtacaaa ctactcaaga ggaagatggc tgtagctgcc gatttccaga agaagaagaa   1020

ggaggatgtg aactgagagt gaagttcagc aggagcgcag acgcccccgc gtaccagcag   1080

ggccagaacc agctctataa cgagctcaat ctaggacgaa gagaggagta cgatgttttg   1140

gacaagagac gtggccggga ccctgagatg gggggaaagc cgagaaggaa gaaccctcag   1200

gaaggcctgt acaatgaact gcagaaagat aagatggcgg aggcctacag tgagattggg   1260

atgaaaggcg agcgccggag gggcaagggg cacgatggcc tttaccaggg tctcagtaca   1320

gccaccaagg acacctacga cgcccttcac atgcaggccc tgccccctcg ctaa         1374
```

```
<210> SEQ ID NO 106
<211> LENGTH: 1374
<212> TYPE: DNA
<213> ORGANISM: Artificial Sequence
<220> FEATURE:
<223> OTHER INFORMATION: Synthetic

<400> SEQUENCE: 106

gacattgtga tgacccagtc tcacaaattc atgtccacat cagtaggaga cagggtcagc     60

atcacctgca aggccagtca ggatgtgact actgctgtag cctggtatca acaaaaacca    120

gggcaatctc ctaaagtact gattttctgg gcatccaccc ggcacactgg agtccctgat    180

cgcttcacag gcagtggatc tgggacagat tatactctca ccatcagcag tgtgcaggct    240

gaagacctgg cactttatta ctgtcagcaa tattatagaa ctcctcggac gttcggtgga    300

ggcaccaaac tggaaatcaa aggtggcggt ggctcgggcg gtggtgggtc gggtggcggc    360

ggatctcagg tgcagctgaa ggagtcagga cctggcctgg tggcgccctc acagaacctg    420

tccatcacat gcactgtctc tgggttctca ttaaccagct atgctataaa ctgggttcgc    480

cagccaccag gaaagggtct ggagtggctt ggaataatat ggactggtgg aggcacaaat    540

tataattcag ctctcaaatc cagactgagc atcagcaaag acaactccaa gagtcaagtt    600

ttcttaaaaa tgaacagtct gcaaactgat gacacagcca ggtactactg tgcctcgggg    660

gtgtactact ttgactactg gggcctaggc accactctca cagtctcctc aattgaagtt    720

atgtatcctc ctccttacct agacaatgag aagagcaatg gaaccattat ccatgtgaaa    780

gggaaacacc tttgtccaag tcccctattt cccggacctt ctaagccctt ttgggtgctg    840

gtggtggttg gggggagtcct ggcttgctat agcttgctag taacagtggc ctttattatt   900

ttctgggtga aacggggcag aaagaaactc ctgtatatat tcaaacaacc atttatgaga    960

ccagtacaaa ctactcaaga ggaagatggc tgtagctgcc gatttccaga agaagaagaa   1020

ggaggatgtg aactgagagt gaagttcagc aggagcgcag acgcccccgc gtaccagcag   1080

ggccagaacc agctctataa cgagctcaat ctaggacgaa gagaggagta cgatgttttg   1140

gacaagagac gtggccggga ccctgagatg gggggaaagc cgagaaggaa gaaccctcag   1200

gaaggcctgt acaatgaact gcagaaagat aagatggcgg aggcctacag tgagattggg   1260

atgaaaggcg agcgccggag gggcaagggg cacgatggcc tttaccaggg tctcagtaca   1320

gccaccaagg acacctacga cgcccttcac atgcaggccc tgccccctcg ctaa         1374
```

```
<210> SEQ ID NO 107
<211> LENGTH: 1392
<212> TYPE: DNA
<213> ORGANISM: Artificial Sequence
<220> FEATURE:
<223> OTHER INFORMATION: Synthetic

<400> SEQUENCE: 107
```

```
gaggtgaagc tgcaggaatc tggagctgag ctggtgaagc ctggggcttc agtgaagatc     60
tcctgcaagg cttctggcta cacattcaat gactacaaca tggactatct gaagcagagc    120
catggaaaga gccttgagtg gattggagat attaatccta actatgatag cactatctac    180
aaccagaagt tcaagggcaa ggccacattg actgtagaca agtcctccag cacagcctac    240
atggagctcc gcagcctgac atctgaggac tctgcagtct attactgtgc aagacgagac    300
tacgatggta ggaggggggc ctggttttct tactggggcc aagggactct ggtcactgtc    360
tctgcaggtg gcggtggctc gggcggtggt gggtcgggtg gcggcggatc tcaaattgtt    420
ctcacccagt ctccagcact catgtctgca tctccagggg agaaggtcac cgtgacctgc    480
actgccagct caagtgtaag ttacatgtac tggtaccagc agaagccaag atcctccccc    540
aaaccctgga tttatctcac atccaacctg gcttctggag tccctactcg cttcagtggc    600
agtgggtctg ggacctctta ttctctcaca atcagcagca tggaggctga agatgctgcc    660
acttattact gccagcagtg ggatagtaac ccgctcacgt tcggtgctgg gaccaaactg    720
gagctgaaaa ttgaagttat gtatcctcct ccttacctag acaatgagaa gagcaatgga    780
accattatcc atgtgaaagg gaaacacctt tgtccaagtc ccctatttcc cggaccttct    840
aagccctttt gggtgctggt ggtggttggg ggagtcctgg cttgctatag cttgctagta    900
acagtggcct ttattatttt ctgggtgaaa cggggcagaa agaaactcct gtatatattc    960
aaacaaccat ttatgagacc agtacaaact actcaagagg aagatggctg tagctgccga   1020
tttccagaag aagaagaagg aggatgtgaa ctgagagtga agttcagcag gagcgcagac   1080
gcccccgcgt accagcaggg ccagaaccag ctctataacg agctcaatct aggacgaaga   1140
gaggagtacg atgttttgga caagagacgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg gcaaggggca cgatggcctt   1320
taccagggtc tcagtacagc caccaaggac acctacgacg cccttcacat gcaggccctg   1380
ccccctcgct aa                                                        1392
```

<210> SEQ ID NO 108
<211> LENGTH: 1392
<212> TYPE: DNA
<213> ORGANISM: Artificial Sequence
<220> FEATURE:
<223> OTHER INFORMATION: Synthetic

<400> SEQUENCE: 108

```
caaattgttc tcacccagtc tccagcactc atgtctgcat ctccagggga gaaggtcacc     60
gtgacctgca ctgccagctc aagtgtaagt tacatgtact ggtaccagca gaagccaaga    120
tcctccccca aaccctggat ttatctcaca tccaacctgg cttctggagt ccctactcgc    180
ttcagtggca gtgggtctgg gacctcttat tctctcacaa tcagcagcat ggaggctgaa    240
gatgctgcca cttattactg ccagcagtgg gatagtaacc cgctcacgtt cggtgctggg    300
accaaactgg agctgaaagg tggcggtggc tcgggcggtg gtgggtcggg tggcggcgga    360
tctgaggtga agctgcagga atctggagct gagctggtga agcctggggc ttcagtgaag    420
atctcctgca aggcttctgg ctacacattc aatgactaca acatggacta tctgaagcag    480
agccatggaa agagccttga gtggattgga gatattaatc ctaactatga tagcactatc    540
tacaaccaga agttcaaggg caaggccaca ttgactgtag acaagtcctc cagcacagcc    600
```

```
tacatggagc tccgcagcct gacatctgag gactctgcag tctattactg tgcaagacga    660

gactacgatg gtaggagggg ggcctggttt tcttactggg gccaagggac tctggtcact    720

gtctctgcaa ttgaagttat gtatcctcct ccttacctag acaatgagaa gagcaatgga    780

accattatcc atgtgaaagg gaaacacctt tgtccaagtc ccctatttcc cggaccttct    840

aagccctttt gggtgctggt ggtggttggg ggagtcctgg cttgctatag cttgctagta    900

acagtggcct ttattatttt ctgggtgaaa cggggcagaa agaaactcct gtatatattc    960

aaacaaccat ttatgagacc agtacaaact actcaagagg aagatggctg tagctgccga   1020

tttccagaag aagaagaagg aggatgtgaa ctgagagtga agttcagcag gagcgcagac   1080

gcccccgcgt accagcaggg ccagaaccag ctctataacg agctcaatct aggacgaaga   1140

gaggagtacg atgttttgga caagagacgt ggccgggacc ctgagatggg gggaaagccg   1200

agaaggaaga accctcagga aggcctgtac aatgaactgc agaaagataa gatggcggag   1260

gcctacagtg agattgggat gaaaggcgag cgccggaggg gcaaggggca cgatggcctt   1320

taccagggtc tcagtacagc caccaaggac acctacgacg cccttcacat gcaggccctg   1380

ccccctcgct aa                                                       1392
```

<210> SEQ ID NO 109
<211> LENGTH: 2160
<212> TYPE: DNA
<213> ORGANISM: Artificial Sequence
<220> FEATURE:
<223> OTHER INFORMATION: Synthetic

<400> SEQUENCE: 109

```
ggtgtccagt gtgacgtgaa gttggtggag tctgggggag gcttagtgaa gcctggaggg     60

tccctgaaac tctcctgtgc agcctctgga ttcactttca gtagatacac catgtcttgg    120

gttcgccaga ctccggagaa gaggctggag tgggtcgcaa ccattagtaa tagtggtagt    180

tatacctact atcgagacag tgtgaagggc cgattcacca tctccagaga caatgccaag    240

aacaccctgt acctgcaaat gagcagtctg aagtctgagg acacagccat gtattactgt    300

acaagggggt cgccctgggg ccaagggact ctggtcactg tctctgcagg tggcggtggc    360

tcgggcggtg gtgggtcggg tggcggcgga tctgacatcc agatgactca gtctccagat    420

tcactgtctg catctgtggg agaaactgtc accatcacat gtggagcaag tgagaacatt    480

tacggtgctt taaattggta tcagcggaaa cagggaaaat ctcctcagct cctgatctat    540

ggtgcaacca agttggcaga tggcatgtca tcgaggttca gtggcagtgg atctaataga    600

cagtattctc tcaagatcag tagcctgcat cctgacgatg ttgcaacgta ttactgtcaa    660

aatgtgttaa gtaagccgta cgcgttcgga ggggggacca aactggaaat aaaaattgaa    720

gttatgtatc ctcctcctta cctagacaat gagaagagca atggaaccat tatccatgtg    780

aaagggaaac acctttgtcc aagtccccta tttcccggac cttctaagcc cttttgggtg    840

ctggtggtgg ttgggggagt cctggcttgc tatagcttgc tagtaacagt ggcctttatt    900

attttctggg tgaggagtaa gaggagcagg ctcctgcaca gtgactacat gaacatgact    960

ccccgccgcc ccgggcccac ccgcaagcat taccagccct atgccccacc acgcgacttc   1020

gcagcctatc gctccctgag agtgaagttc agcaggagcg cagacgcccc cgcgtaccag   1080

cagggccaga accagctcta taacgagctc aatctaggac gaagagagga gtacgatgtt   1140

ttggacaaga gacgtggccg ggaccctgag atggggggaa agccgagaag gaagaaccct   1200

caggaaggcc tgtacaatga actgcagaaa gataagatgg cggaggccta cagtgagatt   1260
```

gggatgaaag gcgagcgccg gaggggcaag gggcacgatg gcctttacca gggtctcagt 1320
acagccacca aggacaccta cgacgccctt cacatgcagg ccctgccccc tcgcggatct 1380
ggcgccacca acttctctct gctgaagcag gccggcgacg tggaggagaa cccaggccca 1440
atggtgagca agggcgagga gctgttcacc ggggtggtgc ccatcctggt cgagctggac 1500
ggcgacgtaa acggccacaa gttcagcgtg tccggcgagg gcgagggcga tgccacctac 1560
ggcaagctga ccctgaagtt catctgcacc accggcaagc tgcccgtgcc ctggcccacc 1620
ctcgtgacca ccctgaccta cggcgtgcag tgcttcagcc gctaccccga ccacatgaag 1680
cagcacgact tcttcaagtc cgccatgccc gaaggctacg tccaggagcg caccatcttc 1740
ttcaaggacg acggcaacta caagacccgc gccgaggtga agttcgaggg cgacaccctg 1800
gtgaaccgca tcgagctgaa gggcatcgac ttcaaggagg acggcaacat cctggggcac 1860
aagctggagt acaactacaa cagccacaac gtctatatca tggccgacaa gcagaagaac 1920
ggcatcaagg tgaacttcaa gatccgccac aacatcgagg acggcagcgt gcagctcgcc 1980
gaccactacc agcagaacac ccccatcggc gacggccccg tgctgctgcc cgacaaccac 2040
tacctgagca cccagtccgc cctgagcaaa gaccccaacg agaagcgcga tcacatggtc 2100
ctgctggagt tcgtgaccgc cgccgggatc actctcggca tggacgagct gtacaagtaa 2160

<210> SEQ ID NO 110
<211> LENGTH: 2169
<212> TYPE: DNA
<213> ORGANISM: Artificial Sequence
<220> FEATURE:
<223> OTHER INFORMATION: Synthetic

<400> SEQUENCE: 110
gacatccaga tgactcagtc tccagattca ctgtctgcat ctgtgggaga aactgtcacc 60
atcacatgtg gagcaagtga gaacatttac ggtgctttaa attggtatca gcggaaacag 120
ggaaaatctc ctcagctcct gatctatggt gcaaccaagt tggcagatgg catgtcatcg 180
aggttcagtg gcagtggatc taatagacag tattctctca agatcagtag cctgcatcct 240
gacgatgttg caacgtatta ctgtcaaaat gtgttaagta agccgtacgc gttcggaggg 300
gggaccaaac tggaaataaa aggtggcggt ggctcgggcg gtggtgggtc gggtggcggc 360
ggatctggtg tccagtgtga cgtgaagttg gtggagtctg gggaggctt agtgaagcct 420 ggagggtccc tgaaactctc ctgtgcagcc tctggattca ctttcagtag atacaccatg 480
tcttgggttc gccagactcc ggagaagagg ctggagtggg tcgcaaccat tagtaatagt 540
ggtagttata cctactatcg agacagtgtg aagggccgat tcaccatctc cagagacaat 600
gccaagaaca ccctgtacct gcaaatgagc agtctgaagt ctgaggacac agccatgtat 660
tactgtacaa gggggtcgcc ctggggccaa gggactctgg tcactgtctc tgcaaccacg 720
acgccagcgc cgcgaccacc aacaccggcg cccaccatcg cgtcgcagcc cctgtccctg 780
cgcccagagg cgtgccggcc agcggcgggg ggcgcagtgc acacgagggg gctggacttc 840
gcctgtgata tctacatctg ggcgcccttg gccgggactt gtggggtcct tctcctgtca 900
ctggttatca ccctttactg caaacggggc agaaagaaac tcctgtatat attcaaacaa 960
ccatttatga gaccagtaca aactactcaa gaggaagatg gctgtagctg ccgatttcca 1020
gaagaagaag aaggaggatg tgaactgaga gtgaagttca gcaggagcgc agacgccccc 1080
gcgtaccagc agggccagaa ccagctctat aacgagctca atctaggacg aagagaggag 1140

```
tacgatgttt tggacaagag acgtggccgg gaccctgaga tggggggaaa gccgagaagg   1200
aagaaccctc aggaaggcct gtacaatgaa ctgcagaaag ataagatggc ggaggcctac   1260
agtgagattg ggatgaaagg cgagcgccgg aggggcaagg ggcacgatgg cctttaccag   1320
ggtctcagta cagccaccaa ggacacctac gacgcccttc acatgcaggc cctgcccccct  1380
cgcggatctg gcgccaccaa cttctctctg ctgaagcagg ccggcgacgt ggaggagaac   1440
ccaggcccaa tggtgagcaa gggcgaggag ctgttcaccg gggtggtgcc catcctggtc   1500
gagctggacg gcgacgtaaa cggccacaag ttcagcgtgt ccggcgaggg cgagggcgat   1560
gccacctacg gcaagctgac cctgaagttc atctgcacca ccggcaagct gcccgtgccc   1620
tggcccaccc tcgtgaccac cctgacctac ggcgtgcagt gcttcagccg ctaccccgac   1680
cacatgaagc agcacgactt cttcaagtcc gccatgcccg aaggctacgt ccaggagcgc   1740
accatcttct tcaaggacga cggcaactac aagacccgcg ccgaggtgaa gttcgagggc   1800
gacaccctgg tgaaccgcat cgagctgaag ggcatcgact tcaaggagga cggcaacatc   1860
ctggggcaca agctggagta caactacaac agccacaacg tctatatcat ggccgacaag   1920
cagaagaacg gcatcaaggt gaacttcaag atccgccaca acatcgagga cggcagcgtg   1980
cagctcgccg accactacca gcagaacacc cccatcggcg acggccccgt gctgctgccc   2040
gacaaccact acctgagcac ccagtccgcc ctgagcaaag accccaacga gaagcgcgat   2100
cacatggtcc tgctggagtt cgtgaccgcc gccgggatca ctctcggcat ggacgagctg   2160
tacaagtaa                                                           2169
```

<210> SEQ ID NO 111
<211> LENGTH: 2187
<212> TYPE: DNA
<213> ORGANISM: Artificial Sequence
<220> FEATURE:
<223> OTHER INFORMATION: Synthetic

<400> SEQUENCE: 111

```
gaggtgaagc tgcagcaatc aggggctgac ctggcaacac ctggggcttc agtgaagttg     60
tcctgcaagg cttctggcta tacctttagt acctactgga tgcagtgggt aaaacagagg    120
cctggacagg gtctggaatg gattgggact atttatcctg gagatggtga tactaggtac    180
actcagaagt tcaagggcaa ggccacattg actgcagata aatcctccag tacagcccac    240
atgcaactca gcagcttggc atctgaggac tctgcggtct attattgtgc aagaggggga    300
ctctattatg gttacgacat tgcttactgg ggccaaggga ctctggtcac tgtctctgca    360
ggtggcggtg gctcgggcgg tggtgggtcg ggtggcggcg gatctgatat tttgatgacc    420
caaactccac tctccctgcc tgtcagtctt ggagatcaag cctccatctc ttgcagatct    480
agtcagagca ttgtacatag taatggaaac acctatttag aatggtacct gcagaaacca    540
ggccagtctc caaagcccct gataaagaaa gtctccaacc gattttctgg ggtcccagac    600
aggttcagtg gcagtggatc agggacagaa ttcacactca agatcagcag agtggaggct    660
gaggatctgg gagtttatta ctgctttcaa ggttcacatg ttccattcac gttcggctcg    720
gggacaaagt tggaaataaa aattgaagtt atgtatcctc ctccttacct agacaatgag    780
aagagcaatg gaaccattat ccatgtgaaa gggaaacacc tttgtccaag tcccctattt    840
cccggacctt ctaagccctt ttgggtgctg gtggtggttg gggagtcct ggcttgctat    900
agcttgctag taacagtggc ctttattatt ttctgggtga ggagtaagag gagcaggctc    960
ctgcacagtg actacatgaa catgactccc cgccgccccg ggcccacccg caagcattac   1020
```

```
cagccctatg ccccaccacg cgacttcgca gcctatcgct ccctgagagt gaagttcagc   1080
aggagcgcag acgcccccgc gtaccagcag ggccagaacc agctctataa cgagctcaat   1140
ctaggacgaa gagaggagta cgatgttttg gacaagagac gtggccggga ccctgagatg   1200
gggggaaagc cgagaaggaa gaaccctcag gaaggcctgt acaatgaact gcagaaagat   1260
aagatggcgg aggcctacag tgagattggg atgaaaggcg agcgccggag gggcaagggg   1320
cacgatggcc tttaccaggg tctcagtaca gccaccaagg acacctacga cgcccttcac   1380
atgcaggccc tgccccctcg cggatctggc gccaccaact tctctctgct gaagcaggcc   1440
ggcgacgtgg aggagaaccc aggcccaatg gtgagcaagg gcgaggagct gttcaccggg   1500
gtggtgccca tcctggtcga gctggacggc gacgtaaacg gccacaagtt cagcgtgtcc   1560
ggcgagggcg agggcgatgc cacctacggc aagctgaccc tgaagttcat ctgcaccacc   1620
ggcaagctgc ccgtgccctg gcccaccctc gtgaccaccc tgacctacgg cgtgcagtgc   1680
ttcagccgct accccgacca catgaagcag cacgacttct tcaagtccgc catgcccgaa   1740
ggctacgtcc aggagcgcac catcttcttc aaggacgacg gcaactacaa gacccgcgcc   1800
gaggtgaagt tcgagggcga caccctggtg aaccgcatcg agctgaaggg catcgacttc   1860
aaggaggacg gcaacatcct ggggcacaag ctggagtaca actacaacag ccacaacgtc   1920
tatatcatgg ccgacaagca gaagaacggc atcaaggtga acttcaagat ccgccacaac   1980
atcgaggacg gcagcgtgca gctcgccgac cactaccagc agaacacccc catcggcgac   2040
ggccccgtgc tgctgcccga caaccactac ctgagcaccc agtccgccct gagcaaagac   2100
cccaacgaga agcgcgatca catggtcctg ctggagttcg tgaccgccgc cgggatcact   2160
ctcggcatgg acgagctgta caagtaa                                       2187
```

```
<210> SEQ ID NO 112
<211> LENGTH: 2187
<212> TYPE: DNA
<213> ORGANISM: Artificial Sequence
<220> FEATURE:
<223> OTHER INFORMATION: Synthetic

<400> SEQUENCE: 112

gatattttga tgacccaaac tccactctcc ctgcctgtca gtcttggaga tcaagcctcc     60
atctcttgca gatctagtca gagcattgta catagtaatg gaaacaccta tttagaatgg    120
tacctgcaga aaccaggcca gtctccaaag cccctgataa agaaagtctc caaccgattt    180
tctggggtcc cagacaggtt cagtggcagt ggatcaggga cagaattcac actcaagatc    240
agcagagtgg aggctgagga tctgggagtt tattactgct ttcaaggttc acatgttcca    300
ttcacgttcg gctcggggac aaagttggaa ataaaaggtg gcggtggctc gggcggtggt    360
gggtcgggtg gcggcggatc tgaggtgaag ctgcagcaat caggggctga cctggcaaca    420
cctggggctt cagtgaagtt gtcctgcaag gcttctggct ataccttag tacctactgg     480
atgcagtggg taaaacagag gcctggacag ggtctggaat ggattgggac tatttatcct    540
ggagatggtg atactaggta cactcagaag ttcaagggca aggccacatt gactgcagat    600
aaatcctcca gtacagccca catgcaactc agcagcttgg catctgagga ctctgcggtc    660
tattattgtg caagaggggg actctattat ggttacgaca ttgcttactg gggccaaggg    720
actctggtca ctgtctctgc aattgaagtt atgtatcctc ctccttacct agacaatgag    780
aagagcaatg gaaccattat ccatgtgaaa gggaaacacc tttgtccaag tcccctattt    840
```

```
cccggacctt ctaagccctt ttgggtgctg gtggtggttg gggggagtcct ggcttgctat    900

agcttgctag taacagtggc ctttattatt ttctgggtga ggagtaagag gagcaggctc    960

ctgcacagtg actacatgaa catgactccc cgccgccccg ggcccacccg caagcattac   1020

cagccctatg ccccaccacg cgacttcgca gcctatcgct ccctgagagt gaagttcagc   1080

aggagcgcag acgcccccgc gtaccagcag ggccagaacc agctctataa cgagctcaat   1140

ctaggacgaa gagaggagta cgatgttttg gacaagagac gtggccggga ccctgagatg   1200

gggggaaagc cgagaaggaa gaaccctcag gaaggcctgt acaatgaact gcagaaagat   1260

aagatggcgg aggcctacag tgagattggg atgaaaggcg agcgccggag gggcaagggg   1320

cacgatggcc tttaccaggg tctcagtaca gccaccaagg acacctacga cgcccttcac   1380

atgcaggccc tgccccctcg cggatctggc gccaccaact tctctctgct gaagcaggcc   1440

ggcgacgtgg aggagaaccc aggcccaatg gtgagcaagg gcgaggagct gttcaccggg   1500

gtggtgccca tcctggtcga gctggacggc gacgtaaacg gccacaagtt cagcgtgtcc   1560

ggcgagggcg agggcgatgc cacctacggc aagctgaccc tgaagttcat ctgcaccacc   1620

ggcaagctgc ccgtgccctg gcccaccctc gtgaccaccc tgacctacgg cgtgcagtgc   1680

ttcagccgct accccgacca catgaagcag cacgacttct tcaagtccgc catgcccgaa   1740

ggctacgtcc aggagcgcac catcttcttc aaggacgacg gcaactacaa gacccgcgcc   1800

gaggtgaagt tcgagggcga caccctggtg aaccgcatcg agctgaaggg catcgacttc   1860

aaggaggacg gcaacatcct ggggcacaag ctggagtaca actacaacag ccacaacgtc   1920

tatatcatgg ccgacaagca gaagaacggc atcaaggtga acttcaagat ccgccacaac   1980

atcgaggacg gcagcgtgca gctcgccgac cactaccagc agaacacccc catcggcgac   2040

ggccccgtgc tgctgcccga caaccactac ctgagcaccc agtccgccct gagcaaagac   2100

cccaacgaga agcgcgatca catggtcctg ctggagttcg tgaccgccgc cgggatcact   2160

ctcggcatgg acgagctgta caagtaa                                       2187
```

<210> SEQ ID NO 113
<211> LENGTH: 2172
<212> TYPE: DNA
<213> ORGANISM: Artificial Sequence
<220> FEATURE:
<223> OTHER INFORMATION: Synthetic

<400> SEQUENCE: 113

```
gaggtgaagc tggtggagtc tggaggaggc ttggtccagc cgggggggtc tctgagactc     60

tcctgttcaa tttctggatt caccttcact gattactaca tgaactgggt ccgccagtct    120

ccaggaaagg cacttgagtg gttgggtttt attagaaaca aagttaatgg tgacacaaca    180

gaatatagtg catctgtgaa gggtcggttc accatctcca gagatatttc ccagagcatc    240

ctctatcttc aaatgaacac cctgagaact gaggacagtg ccacttatta ctgtgcgaga    300

gataagggaa tagcgtacta ctttgactat tggggccaag gcaccactct cacagtctcc    360

tcaggtggcg gtggctcggg cggtggtggg tcgggtggcg gcggatctca aattgttctc    420

tcccagtctc cagcaatcct gtttgcatct ccaggggaga aggtcacaat gacttgtagg    480

gccagctcaa gtgtaagtta cattcactgg taccagcaga agccaggatc ctcccccaaa    540

ccctggattc atggcacatc caacctggct tctggagtcc ctgctcgctt cagtggcagt    600

gggtctggga cctcttactc tctcacaatc agcagaatgg aggctgaaga tgccgccaca    660

tattactgcc agcagtggag tagtaattta tccacgttcg gaggggggac caagctggaa    720
```

```
ataaaaattg aagttatgta tcctcctcct tacctagaca atgagaagag caatggaacc    780
attatccatg tgaaagggaa acacctttgt ccaagtcccc tatttcccgg accttctaag    840
ccctttttggg tgctggtggt ggttggggga gtcctggctt gctatagctt gctagtaaca    900
gtggccttta ttattttctg ggtgaggagt aagaggagca ggctcctgca cagtgactac    960
atgaacatga ctccccgccg ccccgggccc acccgcaagc attaccagcc ctatgcccca   1020
ccacgcgact tcgcagccta tcgctccctg agagtgaagt tcagcaggag cgcagacgcc   1080
cccgcgtacc agcagggcca gaaccagctc tataacgagc tcaatctagg acgaagagag   1140
gagtacgatg ttttggacaa gagacgtggc cgggaccctg agatgggggg aaagccgaga   1200
aggaagaacc ctcaggaagg cctgtacaat gaactgcaga aagataagat ggcggaggcc   1260
tacagtgaga ttgggatgaa aggcgagcgc cggaggggca aggggcacga tggcctttac   1320
cagggtctca gtacagccac caaggacacc tacgacgccc ttcacatgca ggccctgccc   1380
cctcgcggat ctggcgccac caacttctct ctgctgaagc aggccggcga cgtggaggag   1440
aacccaggcc caatggtgag caagggcgag gagctgttca ccggggtggt gcccatcctg   1500
gtcgagctgg acggcgacgt aaacggccac aagttcagcg tgtccggcga gggcgagggc   1560
gatgccacct acggcaagct gaccctgaag ttcatctgca ccaccggcaa gctgcccgtg   1620
ccctggccca ccctcgtgac caccctgacc tacggcgtgc agtgcttcag ccgctacccc   1680
gaccacatga agcagcacga cttcttcaag tccgccatgc ccgaaggcta cgtccaggag   1740
cgcaccatct tcttcaagga cgacggcaac tacaagaccc gcgccgaggt gaagttcgag   1800
ggcgacaccc tggtgaaccg catcgagctg aagggcatcg acttcaagga ggacggcaac   1860
atcctggggc acaagctgga gtacaactac aacagccaca acgtctatat catggccgac   1920
aagcagaaga acggcatcaa ggtgaacttc aagatccgcc acaacatcga ggacggcagc   1980
gtgcagctcg ccgaccacta ccagcagaac acccccatcg gcgacggccc cgtgctgctg   2040
cccgacaacc actacctgag cacccagtcc gccctgagca aagaccccaa cgagaagcgc   2100
gatcacatgg tcctgctgga gttcgtgacc gccgccggga tcactctcgg catggacgag   2160
ctgtacaagt aa                                                       2172
```

<210> SEQ ID NO 114
<211> LENGTH: 2181
<212> TYPE: DNA
<213> ORGANISM: Artificial Sequence
<220> FEATURE:
<223> OTHER INFORMATION: Synthetic

<400> SEQUENCE: 114

```
caaattgttc tctcccagtc tccagcaatc ctgtttgcat ctccagggga gaaggtcaca     60
atgacttgta gggccagctc aagtgtaagt tacattcact ggtaccagca gaagccagga    120
tcctccccca aaccctggat tcatggcaca tccaacctgg cttctggagt ccctgctcgc    180
ttcagtggca gtgggtctgg gacctcttac tctctcacaa tcagcagaat ggaggctgaa    240
gatgccgcca catattactg ccagcagtgg agtagtaatt tatccacgtt cggagggggg    300
accaagctgg aaataaaagg tggcggtggc tcgggcggtg gtgggtcggg tggcggcgga    360
tctgaggtga agctggtgga gtctggagga ggcttggtcc agccgggggg gtctctgaga    420
ctctcctgtt caatttctgg attcaccttc actgattact acatgaactg ggtccgccag    480
tctccaggaa aggcacttga gtggttgggt tttattagaa acaaagttaa tggtgacaca    540
```

```
acagaatata gtgcatctgt gaagggtcgg ttcaccatct ccagagatat ttcccagagc    600
atcctctatc ttcaaatgaa caccctgaga actgaggaca gtgccactta ttactgtgcg    660
agagataagg gaatagcgta ctactttgac tattggggcc aaggcaccac tctcacagtc    720
tcctcaacca cgacgccagc gccgcgacca ccaacaccgg cgcccaccat cgcgtcgcag    780
cccctgtccc tgcgcccaga ggcgtgccgg ccagcggcgg ggggcgcagt gcacacgagg    840
gggctggact tcgcctgtga tatctacatc tgggcgccct tggccgggac ttgtggggtc    900
cttctcctgt cactggttat caccctttac tgcaaacggg gcagaaagaa actcctgtat    960
atattcaaac aaccatttat gagaccagta caaactactc aagaggaaga tggctgtagc   1020
tgccgatttc cagaagaaga agaaggagga tgtgaactga gagtgaagtt cagcaggagc   1080
gcagacgccc ccgcgtacca gcagggccag aaccagctct ataacgagct caatctagga   1140
cgaagagagg agtacgatgt tttggacaag agacgtggcc gggaccctga gatgggggga   1200
aagccgagaa ggaagaaccc tcaggaaggc ctgtacaatg aactgcagaa agataagatg   1260
gcggaggcct acagtgagat tgggatgaaa ggcgagcgcc ggaggggcaa ggggcacgat   1320
ggcctttacc agggtctcag tacagccacc aaggacacct acgacgccct tcacatgcag   1380
gccctgcccc ctcgcggatc tggcgccacc aacttctctc tgctgaagca ggccggcgac   1440
gtggaggaga acccaggccc aatggtgagc aagggcgagg agctgttcac cggggtggtg   1500
cccatcctgg tcgagctgga cggcgacgta aacggccaca agttcagcgt gtccggcgag   1560
ggcgagggcg atgccaccta cggcaagctg accctgaagt tcatctgcac caccggcaag   1620
ctgcccgtgc cctggcccac cctcgtgacc accctgacct acggcgtgca gtgcttcagc   1680
cgctaccccg accacatgaa gcagcacgac ttcttcaagt ccgccatgcc cgaaggctac   1740
gtccaggagc gcaccatctt cttcaaggac gacggcaact acaagacccg cgccgaggtg   1800
aagttcgagg gcgacaccct ggtgaaccgc atcgagctga agggcatcga cttcaaggag   1860
gacggcaaca tcctggggca caagctggag tacaactaca acagccacaa cgtctatatc   1920
atggccgaca agcagaagaa cggcatcaag gtgaacttca agatccgcca caacatcgag   1980
gacggcagcg tgcagctcgc cgaccactac cagcagaaca cccccatcgg cgacggcccc   2040
gtgctgctgc ccgacaacca ctacctgagc acccagtccg ccctgagcaa agaccccaac   2100
gagaagcgcg atcacatggt cctgctggag ttcgtgaccg ccgccgggat cactctcggc   2160
atggacgagc tgtacaagta a                                              2181
```

<210> SEQ ID NO 115
<211> LENGTH: 2157
<212> TYPE: DNA
<213> ORGANISM: Artificial Sequence
<220> FEATURE:
<223> OTHER INFORMATION: Synthetic

<400> SEQUENCE: 115

```
caggtgcagc tgaaggagtc aggacctggc ctggtggcgc cctcacagaa cctgtccatc     60
acatgcactg tctctgggtt ctcattaacc agctatgcta taaactgggt tcgccagcca    120
ccaggaaagg gtctggagtg gcttggaata atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtgcctc gggggtgtac    300
tactttgact actggggcct aggcaccact ctcacagtct cctcaggtgg cggtggctcg    360
ggcggtggtg ggtcgggtgg cggcggatct gacattgtga tgacccagtc tcacaaattc    420
```

```
atgtccacat cagtaggaga cagggtcagc atcacctgca aggccagtca ggatgtgact    480
actgctgtag cctggtatca acaaaaacca gggcaatctc ctaaagtact gattttctgg    540
gcatccaccc ggcacactgg agtccctgat cgcttcacag gcagtggatc tgggacagat    600
tatactctca ccatcagcag tgtgcaggct gaagacctgg cactttatta ctgtcagcaa    660
tattatagaa ctcctcggac gttcggtgga ggcaccaaac tggaaatcaa aattgaagtt    720
atgtatcctc ctccttacct agacaatgag aagagcaatg gaaccattat ccatgtgaaa    780
gggaaacacc tttgtccaag tcccctattt cccggacctt ctaagccctt ttgggtgctg    840
gtggtggttg gggggagtcct ggcttgctat agcttgctag taacagtggc ctttattatt    900
ttctgggtga ggagtaagag gagcaggctc ctgcacagtg actacatgaa catgactccc    960
cgccgccccg ggcccacccg caagcattac cagccctatg ccccaccacg cgacttcgca   1020
gcctatcgct ccctgagagt gaagttcagc aggagcgcag acgcccccgc gtaccagcag   1080
ggccagaacc agctctataa cgagctcaat ctaggacgaa gagaggagta cgatgttttg   1140
gacaagagac gtggccggga ccctgagatg gggggaaagc cgagaaggaa gaaccctcag   1200
gaaggcctgt acaatgaact gcagaaagat aagatggcgg aggcctacag tgagattggg   1260
atgaaaggcg agcgccggag gggcaagggg cacgatggcc tttaccaggg tctcagtaca   1320
gccaccaagg acacctacga cgcccttcac atgcaggccc tgccccctcg cggatctggc   1380
gccaccaact tctctctgct gaagcaggcc ggcgacgtgg aggagaaccc aggcccaatg   1440
gtgagcaagg gcgaggagct gttcaccggg gtggtgccca tcctggtcga gctggacggc   1500
gacgtaaacg gccacaagtt cagcgtgtcc ggcgagggcg agggcgatgc cacctacggc   1560
aagctgaccc tgaagttcat ctgcaccacc ggcaagctgc ccgtgccctg gcccaccctc   1620
gtgaccaccc tgacctacgg cgtgcagtgc ttcagccgct accccgacca catgaagcag   1680
cacgacttct tcaagtccgc catgcccgaa ggctacgtcc aggagcgcac catcttcttc   1740
aaggacgacg gcaactacaa gacccgcgcc gaggtgaagt tcgagggcga caccctggtg   1800
aaccgcatcg agctgaaggg catcgacttc aaggaggacg gcaacatcct ggggcacaag   1860
ctggagtaca actacaacag ccacaacgtc tatatcatgg ccgacaagca gaagaacggc   1920
atcaaggtga acttcaagat ccgccacaac atcgaggacg gcagcgtgca gctcgccgac   1980
cactaccagc agaacacccc catcggcgac ggccccgtgc tgctgcccga caaccactac   2040
ctgagcaccc agtccgccct gagcaaagac cccaacgaga agcgcgatca catggtcctg   2100
ctggagttcg tgaccgccgc cgggatcact ctcggcatgg acgagctgta caagtaa      2157
```

<210> SEQ ID NO 116
<211> LENGTH: 2166
<212> TYPE: DNA
<213> ORGANISM: Artificial Sequence
<220> FEATURE:
<223> OTHER INFORMATION: Synthetic

<400> SEQUENCE: 116

```
gacattgtga tgacccagtc tcacaaattc atgtccacat cagtaggaga cagggtcagc     60
atcacctgca aggccagtca ggatgtgact actgctgtag cctggtatca acaaaaacca    120
gggcaatctc ctaaagtact gattttctgg gcatccaccc ggcacactgg agtccctgat    180
cgcttcacag gcagtggatc tgggacagat tatactctca ccatcagcag tgtgcaggct    240
gaagacctgg cactttatta ctgtcagcaa tattatagaa ctcctcggac gttcggtgga    300
```

```
ggcaccaaac tggaaatcaa aggtggcggt ggctcgggcg gtggtgggtc gggtggcggc    360

ggatctcagg tgcagctgaa ggagtcagga cctggcctgg tggcgccctc acagaacctg    420

tccatcacat gcactgtctc tgggttctca ttaaccagct atgctataaa ctgggttcgc    480

cagccaccag gaaagggtct ggagtggctt ggaataatat ggactggtgg aggcacaaat    540

tataattcag ctctcaaatc cagactgagc atcagcaaag acaactccaa gagtcaagtt    600

ttcttaaaaa tgaacagtct gcaaactgat gacacagcca ggtactactg tgcctcgggg    660

gtgtactact ttgactactg gggcctaggc accactctca cagtctcctc aaccacgacg    720

ccagcgccgc gaccaccaac accggcgccc accatcgcgt cgcagcccct gtccctgcgc    780

ccagaggcgt gccggccagc ggcggggggc gcagtgcaca cgagggggct ggacttcgcc    840

tgtgatatct acatctgggc gcccttggcc gggacttgtg gggtccttct cctgtcactg    900

gttatcaccc tttactgcaa acggggcaga aagaaactcc tgtatatatt caaacaacca    960

tttatgagac cagtacaaac tactcaagag gaagatggct gtagctgccg atttccagaa   1020

gaagaagaag gaggatgtga actgagagtg aagttcagca ggagcgcaga cgcccccgcg   1080

taccagcagg gccagaacca gctctataac gagctcaatc taggacgaag agaggagtac   1140

gatgttttgg acaagagacg tggccgggac cctgagatgg ggggaaagcc gagaaggaag   1200

aaccctcagg aaggcctgta caatgaactg cagaaagata agatggcgga ggcctacagt   1260

gagattggga tgaaaggcga gcgccggagg ggcaaggggc acgatggcct ttaccagggt   1320

ctcagtacag ccaccaagga cacctacgac gcccttcaca tgcaggccct gccccctcgc   1380

ggatctggcg ccaccaactt ctctctgctg aagcaggccg gcgacgtgga ggagaaccca   1440

ggcccaatgg tgagcaaggg cgaggagctg ttcaccgggg tggtgcccat cctggtcgag   1500

ctggacggcg acgtaaacgg ccacaagttc agcgtgtccg gcgagggcga gggcgatgcc   1560

acctacggca agctgaccct gaagttcatc tgcaccaccg gcaagctgcc cgtgccctgg   1620

cccaccctcg tgaccaccct gacctacggc gtgcagtgct tcagccgcta ccccgaccac   1680

atgaagcagc acgacttctt caagtccgcc atgcccgaag gctacgtcca ggagcgcacc   1740

atcttcttca aggacgacgg caactacaag acccgcgccg aggtgaagtt cgagggcgac   1800

accctggtga accgcatcga gctgaagggc atcgacttca aggaggacgg caacatcctg   1860

gggcacaagc tggagtacaa ctacaacagc cacaacgtct atatcatggc cgacaagcag   1920

aagaacggca tcaaggtgaa cttcaagatc cgccacaaca tcgaggacgg cagcgtgcag   1980

ctcgccgacc actaccagca gaacaccccc atcggcgacg gccccgtgct gctgcccgac   2040

aaccactacc tgagcaccca gtccgccctg agcaaagacc ccaacgagaa gcgcgatcac   2100

atggtcctgc tggagttcgt gaccgccgcc gggatcactc tcggcatgga cgagctgtac   2160

aagtaa                                                              2166
```

<210> SEQ ID NO 117
<211> LENGTH: 2175
<212> TYPE: DNA
<213> ORGANISM: Artificial Sequence
<220> FEATURE:
<223> OTHER INFORMATION: Synthetic

<400> SEQUENCE: 117

```
gaggtgaagc tgcaggaatc tggagctgag ctggtgaagc ctggggcttc agtgaagatc     60

tcctgcaagg cttctggcta cacattcaat gactacaaca tggactatct gaagcagagc    120

catggaaaga gccttgagtg gattggagat attaatccta actatgatag cactatctac    180
```

```
aaccagaagt tcaagggcaa ggccacattg actgtagaca agtcctccag cacagcctac    240
atggagctcc gcagcctgac atctgaggac tctgcagtct attactgtgc aagacgagac    300
tacgatggta ggaggggggc ctggttttct tactggggcc aagggactct ggtcactgtc    360
tctgcaggtg gcggtggctc gggcggtggt gggtcgggtg gcggcggatc tcaaattgtt    420
ctcacccagt ctccagcact catgtctgca tctccagggg agaaggtcac cgtgacctgc    480
actgccagct caagtgtaag ttacatgtac tggtaccagc agaagccaag atcctccccc    540
aaaccctgga tttatctcac atccaacctg gcttctggag tccctactcg cttcagtggc    600
agtgggtctg ggacctctta ttctctcaca atcagcagca tggaggctga agatgctgcc    660
acttattact gccagcagtg ggatagtaac ccgctcacgt tcggtgctgg gaccaaactg    720
gagctgaaaa ttgaagttat gtatcctcct ccttacctag acaatgagaa gagcaatgga    780
accattatcc atgtgaaagg gaaacacctt tgtccaagtc ccctatttcc cggaccttct    840
aagccctttt gggtgctggt ggtggttggg ggagtcctgg cttgctatag cttgctagta    900
acagtggcct ttattatttt ctgggtgagg agtaagagga gcaggctcct gcacagtgac    960
tacatgaaca tgactccccg ccgccccggg cccacccgca agcattacca gccctatgcc   1020
ccaccacgcg acttcgcagc ctatcgctcc ctgagagtga agttcagcag gagcgcagac   1080
gcccccgcgt accagcaggg ccagaaccag ctctataacg agctcaatct aggacgaaga   1140
gaggagtacg atgttttgga caagagacgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg gcaaggggca cgatggcctt   1320
taccagggtc tcagtacagc caccaaggac acctacgacg cccttcacat gcaggccctg   1380
ccccctcgcg gatctggcgc caccaacttc tctctgctga agcaggccgg cgacgtggag   1440
gagaacccag gcccaatggt gagcaagggc gaggagctgt tcaccggggt ggtgcccatc   1500
ctggtcgagc tggacggcga cgtaaacggc cacaagttca gcgtgtccgg cgagggcgag   1560
ggcgatgcca cctacggcaa gctgaccctg aagttcatct gcaccaccgg caagctgccc   1620
gtgccctggc ccaccctcgt gaccaccctg acctacggcg tgcagtgctt cagccgctac   1680
cccgaccaca tgaagcagca cgacttcttc aagtccgcca tgcccgaagg ctacgtccag   1740
gagcgcacca tcttcttcaa ggacgacggc aactacaaga cccgcgccga ggtgaagttc   1800
gagggcgaca ccctggtgaa ccgcatcgag ctgaagggca tcgacttcaa ggaggacggc   1860
aacatcctgg ggcacaagct ggagtacaac tacaacagcc acaacgtcta tatcatggcc   1920
gacaagcaga agaacggcat caaggtgaac ttcaagatcc gccacaacat cgaggacggc   1980
agcgtgcagc tcgccgacca ctaccagcag aacaccccca tcggcgacgg ccccgtgctg   2040
ctgcccgaca accactacct gagcacccag tccgccctga gcaaagaccc caacgagaag   2100
cgcgatcaca tggtcctgct ggagttcgtg accgccgccg ggatcactct cggcatggac   2160
gagctgtaca agtaa                                                    2175
```

<210> SEQ ID NO 118
<211> LENGTH: 2184
<212> TYPE: DNA
<213> ORGANISM: Artificial Sequence
<220> FEATURE:
<223> OTHER INFORMATION: Synthetic

<400> SEQUENCE: 118

```
caaattgttc tcacccagtc tccagcactc atgtctgcat ctccagggga gaaggtcacc     60
gtgacctgca ctgccagctc aagtgtaagt tacatgtact ggtaccagca gaagccaaga    120
tcctccccca aaccctggat ttatctcaca tccaacctgg cttctggagt ccctactcgc    180
ttcagtggca gtgggtctgg gacctcttat tctctcacaa tcagcagcat ggaggctgaa    240
gatgctgcca cttattactg ccagcagtgg gatagtaacc cgctcacgtt cggtgctggg    300
accaaactgg agctgaaagg tggcggtggc tcgggcggtg gtgggtcggg tggcggcgga    360
tctgaggtga agctgcagga atctggagct gagctggtga agcctggggc ttcagtgaag    420
atctcctgca aggcttctgg ctacacattc aatgactaca acatggacta tctgaagcag    480
agccatggaa agagccttga gtggattgga gatattaatc ctaactatga tagcactatc    540
tacaaccaga agttcaaggg caaggccaca ttgactgtag acaagtcctc cagcacagcc    600
tacatggagc tccgcagcct gacatctgag gactctgcag tctattactg tgcaagacga    660
gactacgatg gtaggagggg ggcctggttt tcttactggg gccaagggac tctggtcact    720
gtctctgcaa ccacgacgcc agcgccgcga ccaccaacac cggcgcccac catcgcgtcg    780
cagcccctgt ccctgcgccc agaggcgtgc cggccagcgg cggggggcgc agtgcacacg    840
agggggctgg acttcgcctg tgatatctac atctgggcgc ccttggccgg gacttgtggg    900
gtccttctcc tgtcactggt tatcaccctt tactgcaaac ggggcagaaa gaaactcctg    960
tatatattca aacaaccatt tatgagacca gtacaaacta ctcaagagga agatggctgt   1020
agctgccgat ttccagaaga agaagaagga ggatgtgaac tgagagtgaa gttcagcagg   1080
agcgcagacg cccccgcgta ccagcagggc cagaaccagc tctataacga gctcaatcta   1140
ggacgaagag aggagtacga tgttttggac aagagacgtg gccgggaccc tgagatgggg   1200
ggaaagccga gaaggaagaa ccctcaggaa ggcctgtaca atgaactgca gaaagataag   1260
atggcggagg cctacagtga gattgggatg aaaggcgagc gccggagggg caaggggcac   1320
gatggccttt accagggtct cagtacagcc accaaggaca cctacgacgc ccttcacatg   1380
caggccctgc cccctcgcgg atctggcgcc accaacttct ctctgctgaa gcaggccggc   1440
gacgtggagg agaacccagg cccaatggtg agcaagggcg aggagctgtt caccggggtg   1500
gtgcccatcc tggtcgagct ggacggcgac gtaaacggcc acaagttcag cgtgtccggc   1560
gagggcgagg gcgatgccac ctacggcaag ctgaccctga agttcatctg caccaccggc   1620
aagctgcccg tgccctggcc caccctcgtg accaccctga cctacggcgt gcagtgcttc   1680
agccgctacc ccgaccacat gaagcagcac gacttcttca agtccgccat gcccgaaggc   1740
tacgtccagg agcgcaccat cttcttcaag gacgacggca actacaagac ccgcgccgag   1800
gtgaagttcg agggcgacac cctggtgaac cgcatcgagc tgaagggcat cgacttcaag   1860
gaggacggca acatcctggg gcacaagctg gagtacaact acaacagcca caacgtctat   1920
atcatggccg acaagcagaa gaacggcatc aaggtgaact tcaagatccg ccacaacatc   1980
gaggacggca gcgtgcagct cgccgaccac taccagcaga acacccccat cggcgacggc   2040
cccgtgctgc tgcccgacaa ccactacctg agcacccagt ccgccctgag caaagacccc   2100
aacgagaagc gcgatcacat ggtcctgctg gagttcgtga ccgccgccgg gatcactctc   2160
ggcatggacg agctgtacaa gtaa                                          2184
```

<210> SEQ ID NO 119
<211> LENGTH: 1377
<212> TYPE: DNA
<213> ORGANISM: Artificial Sequence
<220> FEATURE:
<223> OTHER INFORMATION: Synthetic

<400> SEQUENCE: 119

```
ggtgtccagt gtgacgtgaa gttggtggag tctgggggag gcttagtgaa gcctggaggg     60
tccctgaaac tctcctgtgc agcctctgga ttcactttca gtagatacac catgtcttgg    120
gttcgccaga ctccggagaa gaggctggag tgggtcgcaa ccattagtaa tagtggtagt    180
tatacctact atcgagacag tgtgaagggc cgattcacca tctccagaga caatgccaag    240
aacaccctgt acctgcaaat gagcagtctg aagtctgagg acacagccat gtattactgt    300
acaagggggt cgccctgggg ccaagggact ctggtcactg tctctgcagg tggcggtggc    360
tcgggcggtg gtgggtcggg tggcggcgga tctgacatcc agatgactca gtctccagat    420
tcactgtctg catctgtggg agaaactgtc accatcacat gtggagcaag tgagaacatt    480
tacggtgctt taaattggta tcagcggaaa cagggaaaat ctcctcagct cctgatctat    540
ggtgcaacca agttggcaga tggcatgtca tcgaggttca gtggcagtgg atctaataga    600
cagtattctc tcaagatcag tagcctgcat cctgacgatg ttgcaacgta ttactgtcaa    660
aatgtgttaa gtaagccgta cgcgttcgga ggggggacca aactggaaat aaaaattgaa    720
gttatgtatc ctcctcctta cctagacaat gagaagagca atggaaccat tatccatgtg    780
aaagggaaac acctttgtcc aagtccccta tttcccggac cttctaagcc cttttgggtg    840
ctggtggtgg ttgggggagt cctggcttgc tatagcttgc tagtaacagt ggcctttatt    900
attttctggg tgaggagtaa gaggagcagg ctcctgcaca gtgactacat gaacatgact    960
ccccgccgcc ccgggcccac ccgcaagcat taccagccct atgccccacc acgcgacttc   1020
gcagcctatc gctccctgag agtgaagttc agcaggagcg cagacgcccc cgcgtaccag   1080
cagggccaga accagctcta taacgagctc aatctaggac gaagagagga gtacgatgtt   1140
ttggacaaga gacgtggccg ggaccctgag atgggggggaa agccgagaag gaagaaccct   1200
caggaaggcc tgtacaatga actgcagaaa gataagatgg cggaggccta cagtgagatt   1260
gggatgaaag gcgagcgccg gaggggcaag gggcacgatg gcctttacca gggtctcagt   1320
acagccacca aggacaccta cgacgccctt cacatgcagg ccctgccccc tcgctaa      1377
```

<210> SEQ ID NO 120
<211> LENGTH: 1377
<212> TYPE: DNA
<213> ORGANISM: Artificial Sequence
<220> FEATURE:
<223> OTHER INFORMATION: Synthetic

<400> SEQUENCE: 120

```
gacatccaga tgactcagtc tccagattca ctgtctgcat ctgtgggaga aactgtcacc     60
atcacatgtg gagcaagtga gaacatttac ggtgctttaa attggtatca gcggaaacag    120
ggaaaatctc ctcagctcct gatctatggt gcaaccaagt tggcagatgg catgtcatcg    180
aggttcagtg gcagtggatc taatagacag tattctctca agatcagtag cctgcatcct    240
gacgatgttg caacgtatta ctgtcaaaat gtgttaagta agccgtacgc gttcggaggg    300
gggaccaaac tggaaataaa aggtggcggt ggctcgggcg gtggtgggtc gggtggcggc    360
ggatctggtg tccagtgtga cgtgaagttg gtggagtctg ggggaggctt agtgaagcct    420
ggagggtccc tgaaactctc ctgtgcagcc tctggattca ctttcagtag atacaccatg    480
tcttgggttc gccagactcc ggagaagagg ctggagtggg tcgcaaccat tagtaatagt    540
```

```
ggtagttata cctactatcg agacagtgtg aagggccgat tcaccatctc cagagacaat    600
gccaagaaca ccctgtacct gcaaatgagc agtctgaagt ctgaggacac agccatgtat    660
tactgtacaa gggggtcgcc ctggggccaa gggactctgg tcactgtctc tgcaattgaa    720
gttatgtatc ctcctcctta cctagacaat gagaagagca atggaaccat tatccatgtg    780
aaagggaaac acctttgtcc aagtccccta tttcccggac cttctaagcc cttttgggtg    840
ctggtggtgg ttgggggagt cctggcttgc tatagcttgc tagtaacagt ggcctttatt    900
attttctggg tgaggagtaa gaggagcagg ctcctgcaca gtgactacat gaacatgact    960
ccccgccgcc ccgggcccac ccgcaagcat taccagccct atgccccacc acgcgacttc   1020
gcagcctatc gctccctgag agtgaagttc agcaggagcg cagacgcccc cgcgtaccag   1080
cagggccaga accagctcta taacgagctc aatctaggac gaagagagga gtacgatgtt   1140
ttggacaaga gacgtggccg ggaccctgag atgggggaa agccgagaag gaagaaccct   1200
caggaaggcc tgtacaatga actgcagaaa gataagatgg cggaggccta cagtgagatt   1260
gggatgaaag gcgagcgccg gaggggcaag gggcacgatg gcctttacca gggtctcagt   1320
acagccacca aggacaccta cgacgccctt cacatgcagg ccctgccccc tcgctaa      1377
```

```
<210> SEQ ID NO 121
<211> LENGTH: 1404
<212> TYPE: DNA
<213> ORGANISM: Artificial Sequence
<220> FEATURE:
<223> OTHER INFORMATION: Synthetic

<400> SEQUENCE: 121
```

```
gaggtgaagc tgcagcaatc aggggctgac ctggcaacac ctggggcttc agtgaagttg     60
tcctgcaagg cttctggcta tacctttagt acctactgga tgcagtgggt aaaacagagg    120
cctggacagg gtctggaatg gattgggact atttatcctg gagatggtga tactaggtac    180
actcagaagt tcaagggcaa ggccacattg actgcagata aatcctccag tacagcccac    240
atgcaactca gcagcttggc atctgaggac tctgcggtct attattgtgc aagaggggga    300
ctctattatg gttacgacat tgcttactgg ggccaaggga ctctggtcac tgtctctgca    360
ggtggcggtg gctcgggcgg tggtgggtcg ggtggcggcg gatctgatat tttgatgacc    420
caaactccac tctccctgcc tgtcagtctt ggagatcaag cctccatctc ttgcagatct    480
agtcagagca ttgtacatag taatggaaac acctatttag aatggtacct gcagaaacca    540
ggccagtctc caaagcccct gataaagaaa gtctccaacc gattttctgg ggtcccagac    600
aggttcagtg gcagtggatc agggacagaa ttcacactca agatcagcag agtggaggct    660
gaggatctgg gagtttatta ctgctttcaa ggttcacatg ttccattcac gttcggctcg    720
gggacaaagt tggaaataaa aattgaagtt atgtatcctc ctccttacct agacaatgag    780
aagagcaatg gaaccattat ccatgtgaaa gggaaacacc tttgtccaag tcccctattt    840
cccggacctt ctaagccctt ttgggtgctg gtggtggttg ggggagtcct ggcttgctat    900
agcttgctag taacagtggc ctttattatt ttctgggtga ggagtaagag gagcaggctc    960
ctgcacagtg actacatgaa catgactccc cgccgccccg ggcccacccg caagcattac   1020
cagccctatg ccccaccacg cgacttcgca gcctatcgct ccctgagagt gaagttcagc   1080
aggagcgcag acgcccccgc gtaccagcag ggccagaacc agctctataa cgagctcaat   1140
ctaggacgaa gagaggagta cgatgttttg gacaagagac gtggccggga ccctgagatg   1200
gggggaaagc cgagaaggaa gaaccctcag gaaggcctgt acaatgaact gcagaaagat   1260
```

```
aagatggcgg aggcctacag tgagattggg atgaaaggcg agcgccggag gggcaagggg   1320

cacgatggcc tttaccaggg tctcagtaca gccaccaagg acacctacga cgcccttcac   1380

atgcaggccc tgccccctcg ctaa                                          1404
```

<210> SEQ ID NO 122
<211> LENGTH: 1404
<212> TYPE: DNA
<213> ORGANISM: Artificial Sequence
<220> FEATURE:
<223> OTHER INFORMATION: Synthetic

<400> SEQUENCE: 122

```
gatattttga tgacccaaac tccactctcc ctgcctgtca gtcttggaga tcaagcctcc     60

atctcttgca gatctagtca gagcattgta catagtaatg gaaacaccta tttagaatgg    120

tacctgcaga aaccaggcca gtctccaaag ctcctgataa agaaagtctc caaccgattt    180

tctggggtcc cagacaggtt cagtggcagt ggatcaggga cagaattcac actcaagatc    240

agcagagtgg aggctgagga tctgggagtt tattactgct ttcaaggttc acatgttcca    300

ttcacgttcg gctcggggac aaagttggaa ataaaaggtg gcggtggctc gggcggtggt    360

gggtcgggtg gcggcggatc tgaggtgaag ctgcagcaat caggggctga cctggcaaca    420

cctggggctt cagtgaagtt gtcctgcaag gcttctggct atacctttag tacctactgg    480

atgcagtggg taaaacagag gcctggacag ggtctggaat ggattgggac tatttatcct    540

ggagatggtg atactaggta cactcagaag ttcaagggca aggccacatt gactgcagat    600

aaatcctcca gtacagccca catgcaactc agcagcttgg catctgagga ctctgcggtc    660

tattattgtg caagaggggg actctattat ggttacgaca ttgcttactg gggccaaggg    720

actctggtca ctgtctctgc aattgaagtt atgtatcctc ctccttacct agacaatgag    780

aagagcaatg gaaccattat ccatgtgaaa gggaaacacc tttgtccaag tcccctattt    840

cccggacctt ctaagccctt ttgggtgctg gtggtggttg gggagtcct ggcttgctat     900

agcttgctag taacagtggc ctttattatt ttctgggtga ggagtaagag gagcaggctc    960

ctgcacagtg actacatgaa catgactccc cgccgccccg ggcccacccg caagcattac   1020

cagccctatg ccccaccacg cgacttcgca gcctatcgct ccctgagagt gaagttcagc   1080

aggagcgcag acgcccccgc gtaccagcag ggccagaacc agctctataa cgagctcaat   1140

ctaggacgaa gagaggagta cgatgttttg gacaagagac gtggccggga ccctgagatg   1200

gggggaaagc cgagaaggaa gaaccctcag gaaggcctgt acaatgaact gcagaaagat   1260

aagatggcgg aggcctacag tgagattggg atgaaaggcg agcgccggag gggcaagggg   1320

cacgatggcc tttaccaggg tctcagtaca gccaccaagg acacctacga cgcccttcac   1380

atgcaggccc tgccccctcg ctaa                                          1404
```

<210> SEQ ID NO 123
<211> LENGTH: 1389
<212> TYPE: DNA
<213> ORGANISM: Artificial Sequence
<220> FEATURE:
<223> OTHER INFORMATION: Synthetic

<400> SEQUENCE: 123

```
gaggtgaagc tggtggagtc tggaggaggc ttggtccagc cggggggggtc tctgagactc     60

tcctgttcaa tttctggatt caccttcact gattactaca tgaactgggt ccgccagtct    120
```

```
ccaggaaagg cacttgagtg gttgggtttt attagaaaca aagttaatgg tgacacaaca    180

gaatatagtg catctgtgaa gggtcggttc accatctcca gagatatttc ccagagcatc    240

ctctatcttc aaatgaacac cctgagaact gaggacagtg ccacttatta ctgtgcgaga    300

gataagggaa tagcgtacta ctttgactat tggggccaag gcaccactct cacagtctcc    360

tcaggtggcg gtggctcggg cggtggtggg tcgggtggcg gcggatctca aattgttctc    420

tcccagtctc cagcaatcct gtttgcatct ccaggggaga aggtcacaat gacttgtagg    480

gccagctcaa gtgtaagtta cattcactgg taccagcaga agccaggatc ctcccccaaa    540

ccctggattc atggcacatc caacctggct tctggagtcc ctgctcgctt cagtggcagt    600

gggtctggga cctcttactc tctcacaatc agcagaatgg aggctgaaga tgccgccaca    660

tattactgcc agcagtggag tagtaattta tccacgttcg gagggggac caagctggaa     720

ataaaaattg aagttatgta tcctcctcct tacctagaca atgagaagag caatggaacc    780

attatccatg tgaaagggaa acacctttgt ccaagtcccc tatttcccgg accttctaag    840

ccctttttggg tgctggtggt ggttggggga gtcctggctt gctatagctt gctagtaaca   900

gtggccttta ttattttctg ggtgaggagt aagaggagca ggctcctgca cagtgactac    960

atgaacatga ctccccgccg ccccgggccc acccgcaagc attaccagcc ctatgcccca   1020

ccacgcgact tcgcagccta tcgctccctg agagtgaagt tcagcaggag cgcagacgcc   1080

cccgcgtacc agcagggcca gaaccagctc tataacgagc tcaatctagg acgaagagag   1140

gagtacgatg ttttggacaa gagacgtggc cgggaccctg agatgggggg aaagccgaga   1200

aggaagaacc ctcaggaagg cctgtacaat gaactgcaga aagataagat ggcggaggcc   1260

tacagtgaga ttgggatgaa aggcgagcgc cggaggggca aggggcacga tggcctttac   1320

cagggtctca gtacagccac caaggacacc tacgacgccc ttcacatgca ggccctgccc   1380

cctcgctaa                                                           1389
```

```
<210> SEQ ID NO 124
<211> LENGTH: 1389
<212> TYPE: DNA
<213> ORGANISM: Artificial Sequence
<220> FEATURE:
<223> OTHER INFORMATION: Synthetic

<400> SEQUENCE: 124
```

```
caaattgttc tctcccagtc tccagcaatc ctgtttgcat ctccagggga gaaggtcaca     60

atgacttgta gggccagctc aagtgtaagt tacattcact ggtaccagca gaagccagga    120

tcctccccca aaccctggat tcatggcaca tccaacctgg cttctggagt ccctgctcgc    180

ttcagtggca gtgggtctgg gacctcttac tctctcacaa tcagcagaat ggaggctgaa    240

gatgccgcca catattactg ccagcagtgg agtagtaatt tatccacgtt cggagggggg    300

accaagctgg aaataaaagg tggcggtggc tcgggcggtg gtgggtcggg tggcggcgga    360

tctgaggtga agctggtgga gtctggagga ggcttggtcc agccgggggg gtctctgaga    420

ctctcctgtt caatttctgg attcaccttc actgattact acatgaactg ggtccgccag    480

tctccaggaa aggcacttga gtggttgggt tttattagaa acaaagttaa tggtgacaca    540

acagaatata gtgcatctgt gaagggtcgg ttcaccatct ccagagatat ttcccagagc    600

atcctctatc ttcaaatgaa caccctgaga actgaggaca gtgccactta ttactgtgcg    660

agagataagg gaatagcgta ctactttgac tattggggcc aaggcaccac tctcacagtc    720

tcctcaattg aagttatgta tcctcctcct tacctagaca atgagaagag caatggaacc    780
```

```
attatccatg tgaaagggaa acacctttgt ccaagtcccc tatttcccgg accttctaag    840
cccttttggg tgctggtggt ggttggggga gtcctggctt gctatagctt gctagtaaca    900
gtggccttta ttattttctg ggtgaggagt aagaggagca ggctcctgca cagtgactac    960
atgaacatga ctccccgccg ccccgggccc acccgcaagc attaccagcc ctatgcccca   1020
ccacgcgact tcgcagccta tcgctccctg agagtgaagt tcagcaggag cgcagacgcc   1080
cccgcgtacc agcagggcca gaaccagctc tataacgagc tcaatctagg acgaagagag   1140
gagtacgatg ttttggacaa gagacgtggc cgggaccctg agatgggggg aaagccgaga   1200
aggaagaacc ctcaggaagg cctgtacaat gaactgcaga aagataagat ggcggaggcc   1260
tacagtgaga ttgggatgaa aggcgagcgc cggaggggca aggggcacga tggcctttac   1320
cagggtctca gtacagccac caaggacacc tacgacgccc ttcacatgca ggccctgccc   1380
cctcgctaa                                                           1389
```

```
<210> SEQ ID NO 125
<211> LENGTH: 1374
<212> TYPE: DNA
<213> ORGANISM: Artificial Sequence
<220> FEATURE:
<223> OTHER INFORMATION: Synthetic

<400> SEQUENCE: 125

caggtgcagc tgaaggagtc aggacctggc ctggtggcgc cctcacagaa cctgtccatc     60
acatgcactg tctctgggtt ctcattaacc agctatgcta taaactgggt tcgccagcca    120
ccaggaaagg gtctggagtg gcttggaata atatggactg gtggaggcac aaattataat    180
tcagctctca aatccagact gagcatcagc aaagacaact ccaagagtca agttttctta    240
aaaatgaaca gtctgcaaac tgatgacaca gccaggtact actgtgcctc gggggtgtac    300
tactttgact actggggcct aggcaccact ctcacagtct cctcaggtgg cggtggctcg    360
ggcggtggtg ggtcgggtgg cggcggatct gacattgtga tgacccagtc tcacaaattc    420
atgtccacat cagtaggaga cagggtcagc atcacctgca aggccagtca ggatgtgact    480
actgctgtag cctggtatca acaaaaacca gggcaatctc ctaaagtact gattttctgg    540
gcatccaccc ggcacactgg agtccctgat cgcttcacag gcagtggatc tgggacagat    600
tatactctca ccatcagcag tgtgcaggct gaagacctgg cactttatta ctgtcagcaa    660
tattatagaa ctcctcggac gttcggtgga ggcaccaaac tggaaatcaa aattgaagtt    720
atgtatcctc ctccttacct agacaatgag aagagcaatg gaaccattat ccatgtgaaa    780
gggaaacacc tttgtccaag tcccctattt cccggacctt ctaagccctt ttgggtgctg    840
gtggtggttg ggggagtcct ggcttgctat agcttgctag taacagtggc ctttattatt    900
ttctgggtga ggagtaagag gagcaggctc ctgcacagtg actacatgaa catgactccc    960
cgccgccccg ggcccacccg caagcattac cagccctatg ccccaccacg cgacttcgca   1020
gcctatcgct ccctgagagt gaagttcagc aggagcgcag acgcccccgc gtaccagcag   1080
ggccagaacc agctctataa cgagctcaat ctaggacgaa gagaggagta cgatgttttg   1140
gacaagagac gtggccggga ccctgagatg gggggaaagc cgagaaggaa gaaccctcag   1200
gaaggcctgt acaatgaact gcagaaagat aagatggcgg aggcctacag tgagattggg   1260
atgaaaggcg agcgccggag gggcaagggg cacgatggcc tttaccaggg tctcagtaca   1320
gccaccaagg acacctacga cgcccttcac atgcaggccc tgccccctcg ctaa         1374
```

<210> SEQ ID NO 126
<211> LENGTH: 1374
<212> TYPE: DNA
<213> ORGANISM: Artificial Sequence
<220> FEATURE:
<223> OTHER INFORMATION: Synthetic

<400> SEQUENCE: 126
gacattgtga tgacccagtc tcacaaattc atgtccacat cagtaggaga cagggtcagc 60
atcacctgca aggccagtca ggatgtgact actgctgtag cctggtatca acaaaaacca 120
gggcaatctc ctaaagtact gattttctgg gcatccaccc ggcacactgg agtccctgat 180
cgcttcacag gcagtggatc tgggacagat tatactctca ccatcagcag tgtgcaggct 240
gaagacctgg cactttatta ctgtcagcaa tattatagaa ctcctcggac gttcggtgga 300
ggcaccaaac tggaaatcaa aggtggcggt ggctcgggcg gtggtgggtc gggtggcggc 360
ggatctcagg tgcagctgaa ggagtcagga cctggcctgg tggcgccctc acagaacctg 420
tccatcacat gcactgtctc tgggttctca ttaaccagct atgctataaa ctgggttcgc 480
cagccaccag gaaagggtct ggagtggctt ggaataatat ggactggtgg aggcacaaat 540
tataattcag ctctcaaatc cagactgagc atcagcaaag acaactccaa gagtcaagtt 600
ttcttaaaaa tgaacagtct gcaaactgat gacacagcca ggtactactg tgcctcgggg 660
gtgtactact ttgactactg gggcctaggc accactctca cagtctcctc aattgaagtt 720
atgtatcctc ctccttacct agacaatgag aagagcaatg gaaccattat ccatgtgaaa 780
gggaaacacc tttgtccaag tcccctattt cccggacctt ctaagccctt ttgggtgctg 840
gtggtggttg gggagtcct ggcttgctat agcttgctag taacagtggc ctttattatt 900
ttctgggtga ggagtaagag gagcaggctc ctgcacagtg actacatgaa catgactccc 960
cgccgccccg ggcccacccg caagcattac cagccctatg ccccaccacg cgacttcgca 1020
gcctatcgct ccctgagagt gaagttcagc aggagcgcag acgcccccgc gtaccagcag 1080
ggccagaacc agctctataa cgagctcaat ctaggacgaa gagaggagta cgatgttttg 1140
gacaagagac gtggccggga ccctgagatg gggggaaagc cgagaaggaa gaaccctcag 1200
gaaggcctgt acaatgaact gcagaaagat aagatggcgg aggcctacag tgagattggg 1260
atgaaaggcg agcgccggag gggcaagggg cacgatggcc tttaccaggg tctcagtaca 1320
gccaccaagg acacctacga cgcccttcac atgcaggccc tgccccctcg ctaa 1374

<210> SEQ ID NO 127
<211> LENGTH: 1392
<212> TYPE: DNA
<213> ORGANISM: Artificial Sequence
<220> FEATURE:
<223> OTHER INFORMATION: Synthetic

<400> SEQUENCE: 127
gaggtgaagc tgcaggaatc tggagctgag ctggtgaagc ctggggcttc agtgaagatc 60
tcctgcaagg cttctggcta cacattcaat gactacaaca tggactatct gaagcagagc 120
catggaaaga gccttgagtg gattggagat attaatccta actatgatag cactatctac 180
aaccagaagt tcaagggcaa ggccacattg actgtagaca agtcctccag cacagcctac 240
atggagctcc gcagcctgac atctgaggac tctgcagtct attactgtgc aagacgagac 300
tacgatggta ggaggggggc ctggttttct tactggggcc aagggactct ggtcactgtc 360
tctgcaggtg gcggtggctc gggcggtggt gggtcgggtg gcggcggatc tcaaattgtt 420

```
ctcacccagt ctccagcact catgtctgca tctccagggg agaaggtcac cgtgacctgc    480
actgccagct caagtgtaag ttacatgtac tggtaccagc agaagccaag atcctccccc    540
aaaccctgga tttatctcac atccaacctg gcttctggag tccctactcg cttcagtggc    600
agtgggtctg ggacctctta ttctctcaca atcagcagca tggaggctga agatgctgcc    660
acttattact gccagcagtg ggatagtaac ccgctcacgt tcggtgctgg gaccaaactg    720
gagctgaaaa ttgaagttat gtatcctcct ccttacctag acaatgagaa gagcaatgga    780
accattatcc atgtgaaagg gaaacacctt tgtccaagtc ccctatttcc cggaccttct    840
aagccctttt gggtgctggt ggtggttggg ggagtcctgg cttgctatag cttgctagta    900
acagtggcct ttattatttt ctgggtgagg agtaagagga gcaggctcct gcacagtgac    960
tacatgaaca tgactccccg ccgccccggg cccacccgca agcattacca gccctatgcc   1020
ccaccacgcg acttcgcagc ctatcgctcc ctgagagtga agttcagcag gagcgcagac   1080
gcccccgcgt accagcaggg ccagaaccag ctctataacg agctcaatct aggacgaaga   1140
gaggagtacg atgttttgga caagagacgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg gcaaggggca cgatggcctt   1320
taccagggtc tcagtacagc caccaaggac acctacgacg cccttcacat gcaggccctg   1380
ccccctcgct aa                                                       1392
```

<210> SEQ ID NO 128
<211> LENGTH: 1392
<212> TYPE: DNA
<213> ORGANISM: Artificial Sequence
<220> FEATURE:
<223> OTHER INFORMATION: Synthetic

<400> SEQUENCE: 128

```
caaattgttc tcacccagtc tccagcactc atgtctgcat ctccagggga gaaggtcacc     60
gtgacctgca ctgccagctc aagtgtaagt tacatgtact ggtaccagca gaagccaaga    120
tcctccccca aaccctggat ttatctcaca tccaacctgg cttctggagt ccctactcgc    180
ttcagtggca gtgggtctgg gacctcttat tctctcacaa tcagcagcat ggaggctgaa    240
gatgctgcca cttattactg ccagcagtgg gatagtaacc cgctcacgtt cggtgctggg    300
accaaactgg agctgaaagg tggcggtggc tcgggcggtg gtgggtcggg tggcggcgga    360
tctgaggtga agctgcagga atctggagct gagctggtga agcctggggc ttcagtgaag    420
atctcctgca aggcttctgg ctacacattc aatgactaca acatggacta tctgaagcag    480
agccatggaa agagccttga gtggattgga gatattaatc ctaactatga tagcactatc    540
tacaaccaga agttcaaggg caaggccaca ttgactgtag acaagtcctc cagcacagcc    600
tacatggagc tccgcagcct gacatctgag gactctgcag tctattactg tgcaagacga    660
gactacgatg gtaggagggg ggcctggttt tcttactggg gccaagggac tctggtcact    720
gtctctgcaa ttgaagttat gtatcctcct ccttacctag acaatgagaa gagcaatgga    780
accattatcc atgtgaaagg gaaacacctt tgtccaagtc ccctatttcc cggaccttct    840
aagccctttt gggtgctggt ggtggttggg ggagtcctgg cttgctatag cttgctagta    900
acagtggcct ttattatttt ctgggtgagg agtaagagga gcaggctcct gcacagtgac    960
tacatgaaca tgactccccg ccgccccggg cccacccgca agcattacca gccctatgcc   1020
```

```
ccaccacgcg acttcgcagc ctatcgctcc ctgagagtga agttcagcag gagcgcagac   1080

gcccccgcgt accagcaggg ccagaaccag ctctataacg agctcaatct aggacgaaga   1140

gaggagtacg atgttttgga caagagacgt ggccgggacc ctgagatggg gggaaagccg   1200

agaaggaaga accctcagga aggcctgtac aatgaactgc agaaagataa gatggcggag   1260

gcctacagtg agattgggat gaaaggcgag cgccggaggg gcaaggggca cgatggcctt   1320

taccagggtc tcagtacagc caccaaggac acctacgacg cccttcacat gcaggccctg   1380

ccccctcgct aa                                                        1392
```

<210> SEQ ID NO 129
<211> LENGTH: 21
<212> TYPE: DNA
<213> ORGANISM: Artificial Sequence
<220> FEATURE:
<223> OTHER INFORMATION: Synthetic

<400> SEQUENCE: 129
ggattcactt tcagtagata c 21

<210> SEQ ID NO 130
<211> LENGTH: 18
<212> TYPE: DNA
<213> ORGANISM: Artificial Sequence
<220> FEATURE:
<223> OTHER INFORMATION: Synthetic

<400> SEQUENCE: 130
agtaatagtg gtagttat 18

<210> SEQ ID NO 131
<211> LENGTH: 9
<212> TYPE: DNA
<213> ORGANISM: Artificial Sequence
<220> FEATURE:
<223> OTHER INFORMATION: Synthetic

<400> SEQUENCE: 131 gggtcgccc 9

<210> SEQ ID NO 132
<211> LENGTH: 33
<212> TYPE: DNA
<213> ORGANISM: Artificial Sequence
<220> FEATURE:
<223> OTHER INFORMATION: Synthetic

<400> SEQUENCE: 132
ggagcaagtg agaacattta cggtgcttta aat 33

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
ggtgcaacca agttggcaga t 21

<210> SEQ ID NO 134
<211> LENGTH: 27
<212> TYPE: DNA
<213> ORGANISM: Artificial Sequence
<220> FEATURE:
<223> OTHER INFORMATION: Synthetic

<400> SEQUENCE: 134
caaaatgtgt taagtaagcc gtacgcg 27

<210> SEQ ID NO 135
<211> LENGTH: 21
<212> TYPE: DNA
<213> ORGANISM: Artificial Sequence
<220> FEATURE:
<223> OTHER INFORMATION: Synthetic

<400> SEQUENCE: 135
ggctatacct ttagtaccta c 21

<210> SEQ ID NO 136
<211> LENGTH: 18
<212> TYPE: DNA
<213> ORGANISM: Artificial Sequence
<220> FEATURE:
<223> OTHER INFORMATION: Synthetic

<400> SEQUENCE: 136
tatcctggag atggtgat 18

<210> SEQ ID NO 137
<211> LENGTH: 33
<212> TYPE: DNA
<213> ORGANISM: Artificial Sequence
<220> FEATURE:
<223> OTHER INFORMATION: Synthetic

<400> SEQUENCE: 137
gggggactct attatggtta cgacattgct tac 33

<210> SEQ ID NO 138
<211> LENGTH: 48
<212> TYPE: DNA
<213> ORGANISM: Artificial Sequence
<220> FEATURE:
<223> OTHER INFORMATION: Synthetic

<400> SEQUENCE: 138
agatctagtc agagcattgt acatagtaat ggaaacacct atttagaa 48

<210> SEQ ID NO 139
<211> LENGTH: 21
<212> TYPE: DNA
<213> ORGANISM: Artificial Sequence
<220> FEATURE:
<223> OTHER INFORMATION: Synthetic

<400> SEQUENCE: 139
aaagtctcca accgattttc t 21

<210> SEQ ID NO 140
<211> LENGTH: 27
<212> TYPE: DNA
<213> ORGANISM: Artificial Sequence
<220> FEATURE:
<223> OTHER INFORMATION: Synthetic

<400> SEQUENCE: 140
tttcaaggtt cacatgttcc attcacg 27

<210> SEQ ID NO 141
<211> LENGTH: 21
<212> TYPE: DNA
<213> ORGANISM: Artificial Sequence
<220> FEATURE:
<223> OTHER INFORMATION: Synthetic

<400> SEQUENCE: 141
ggattcacct tcactgatta c 21

<210> SEQ ID NO 142
<211> LENGTH: 24
<212> TYPE: DNA
<213> ORGANISM: Artificial Sequence
<220> FEATURE:
<223> OTHER INFORMATION: Synthetic

<400> SEQUENCE: 142
agaaacaaag ttaatggtga caca 24

<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143
gataagggaa tagcgtacta ctttgactat 30

<210> SEQ ID NO 144
<211> LENGTH: 30
<212> TYPE: DNA
<213> ORGANISM: Artificial Sequence
<220> FEATURE:
<223> OTHER INFORMATION: Synthetic

<400> SEQUENCE: 144
agggccagct caagtgtaag ttacattcac 30

<210> SEQ ID NO 145
<211> LENGTH: 21
<212> TYPE: DNA
<213> ORGANISM: Artificial Sequence
<220> FEATURE:
<223> OTHER INFORMATION: Synthetic

<400> SEQUENCE: 145
ggcacatcca acctggcttc t 21

<210> SEQ ID NO 146
<211> LENGTH: 27
<212> TYPE: DNA
<213> ORGANISM: Artificial Sequence
<220> FEATURE:
<223> OTHER INFORMATION: Synthetic

<400> SEQUENCE: 146
cagcagtgga gtagtaattt atccacg 27

<210> SEQ ID NO 147
<211> LENGTH: 21
<212> TYPE: DNA
<213> ORGANISM: Artificial Sequence
<220> FEATURE:
<223> OTHER INFORMATION: Synthetic

<400> SEQUENCE: 147
gggttctcat taaccagcta t 21

<210> SEQ ID NO 148
<211> LENGTH: 15
<212> TYPE: DNA
<213> ORGANISM: Artificial Sequence
<220> FEATURE:
<223> OTHER INFORMATION: Synthetic

<400> SEQUENCE: 148
tggactggtg gaggc 15

<210> SEQ ID NO 149
<211> LENGTH: 21
<212> TYPE: DNA
<213> ORGANISM: Artificial Sequence
<220> FEATURE:
<223> OTHER INFORMATION: Synthetic

<400> SEQUENCE: 149
ggggtgtact actttgacta c 21

<210> SEQ ID NO 150
<211> LENGTH: 33
<212> TYPE: DNA
<213> ORGANISM: Artificial Sequence
<220> FEATURE:
<223> OTHER INFORMATION: Synthetic

<400> SEQUENCE: 150
aaggccagtc aggatgtgac tactgctgta gcc 33

<210> SEQ ID NO 151
<211> LENGTH: 21
<212> TYPE: DNA
<213> ORGANISM: Artificial Sequence
<220> FEATURE:
<223> OTHER INFORMATION: Synthetic

<400> SEQUENCE: 151
tgggcatcca cccggcacac t 21

<210> SEQ ID NO 152
<211> LENGTH: 27
<212> TYPE: DNA
<213> ORGANISM: Artificial Sequence
<220> FEATURE:
<223> OTHER INFORMATION: Synthetic

<400> SEQUENCE: 152
cagcaatatt atagaactcc tcggacg 27

<210> SEQ ID NO 153
<211> LENGTH: 21
<212> TYPE: DNA
<213> ORGANISM: Artificial Sequence
<220> FEATURE:
<223> OTHER INFORMATION: Synthetic

<400> SEQUENCE: 153
ggctacacat tcaatgacta c 21

<210> SEQ ID NO 154

<211> LENGTH: 18
<212> TYPE: DNA
<213> ORGANISM: Artificial Sequence
<220> FEATURE:
<223> OTHER INFORMATION: Synthetic

<400> SEQUENCE: 154
aatcctaact atgatagc 18

<210> SEQ ID NO 155
<211> LENGTH: 39
<212> TYPE: DNA
<213> ORGANISM: Artificial Sequence
<220> FEATURE:
<223> OTHER INFORMATION: Synthetic

<400> SEQUENCE: 155
cgagactacg atggtaggag gggggcctgg ttttcttac 39

<210> SEQ ID NO 156
<211> LENGTH: 30
<212> TYPE: DNA
<213> ORGANISM: Artificial Sequence
<220> FEATURE:
<223> OTHER INFORMATION: Synthetic

<400> SEQUENCE: 156
actgccagct caagtgtaag ttacatgtac 30

<210> SEQ ID NO 157
<211> LENGTH: 21
<212> TYPE: DNA
<213> ORGANISM: Artificial Sequence
<220> FEATURE:
<223> OTHER INFORMATION: Synthetic

<400> SEQUENCE: 157
ctcacatcca acctggcttc t 21

<210> SEQ ID NO 158
<211> LENGTH: 27
<212> TYPE: DNA
<213> ORGANISM: Artificial Sequence
<220> FEATURE:
<223> OTHER INFORMATION: Synthetic

<400> SEQUENCE: 158
cagcagtggg atagtaaccc gctcacg 27

<210> SEQ ID NO 159
<211> LENGTH: 29
<212> TYPE: DNA
<213> ORGANISM: Artificial Sequence
<220> FEATURE:
<223> OTHER INFORMATION: Synthetic

<400> SEQUENCE: 159
gcggatccgg tgtccagtgt gacgtgaag 29

<210> SEQ ID NO 160
<211> LENGTH: 28
<212> TYPE: DNA
<213> ORGANISM: Artificial Sequence
<220> FEATURE:
<223> OTHER INFORMATION: Synthetic

<400> SEQUENCE: 160
gcggatccga catccagatg actcagtc 28

<210> SEQ ID NO 161
<211> LENGTH: 28
<212> TYPE: DNA
<213> ORGANISM: Artificial Sequence
<220> FEATURE:
<223> OTHER INFORMATION: Synthetic

<400> SEQUENCE: 161
gcggatccga ggtgaagctg cagcaatc 28

<210> SEQ ID NO 162
<211> LENGTH: 28
<212> TYPE: DNA
<213> ORGANISM: Artificial Sequence
<220> FEATURE:
<223> OTHER INFORMATION: Synthetic

<400> SEQUENCE: 162
gcggatccga tattttgatg acccaaac 28

<210> SEQ ID NO 163
<211> LENGTH: 30
<212> TYPE: DNA
<213> ORGANISM: Artificial Sequence
<220> FEATURE:
<223> OTHER INFORMATION: Synthetic

<400> SEQUENCE: 163
gcggatccga ggtgaagctg gtggagtctg 30

<210> SEQ ID NO 164
<211> LENGTH: 28
<212> TYPE: DNA
<213> ORGANISM: Artificial Sequence
<220> FEATURE:
<223> OTHER INFORMATION: Synthetic

<400> SEQUENCE: 164
gcggatccca aattgttctc tcccagtc 28

<210> SEQ ID NO 165
<211> LENGTH: 30
<212> TYPE: DNA
<213> ORGANISM: Artificial Sequence
<220> FEATURE:
<223> OTHER INFORMATION: Synthetic

<400> SEQUENCE: 165
gcggatccca ggtgcagctg aaggagtcag 30

<210> SEQ ID NO 166
<211> LENGTH: 28
<212> TYPE: DNA
<213> ORGANISM: Artificial Sequence
<220> FEATURE:
<223> OTHER INFORMATION: Synthetic

<400> SEQUENCE: 166
gcggatccca aattgttctc tcccagtc 28

<210> SEQ ID NO 167
<211> LENGTH: 30
<212> TYPE: DNA

<213> ORGANISM: Artificial Sequence
<220> FEATURE:
<223> OTHER INFORMATION: Synthetic

<400> SEQUENCE: 167
gcggatccga ggtgaagctg caggaatctg 30

<210> SEQ ID NO 168
<211> LENGTH: 28
<212> TYPE: DNA
<213> ORGANISM: Artificial Sequence
<220> FEATURE:
<223> OTHER INFORMATION: Synthetic

<400> SEQUENCE: 168
gcggatccca aattgttctc acccagtc 28

<210> SEQ ID NO 169
<211> LENGTH: 29
<212> TYPE: DNA
<213> ORGANISM: Artificial Sequence
<220> FEATURE:
<223> OTHER INFORMATION: Synthetic

<400> SEQUENCE: 169
gcgaattctt acttgtacag ctcgtccat 29

<210> SEQ ID NO 170
<211> LENGTH: 29
<212> TYPE: DNA
<213> ORGANISM: Artificial Sequence
<220> FEATURE:
<223> OTHER INFORMATION: Synthetic

<400> SEQUENCE: 170
gcgaattctt agcgaggggg cagggcctg 29

<210> SEQ ID NO 171
<211> LENGTH: 238
<212> TYPE: PRT
<213> ORGANISM: Artificial Sequence
<220> FEATURE:
<223> OTHER INFORMATION: Synthetic

<400> SEQUENCE: 171

```
Gly Val Gln Cys Asp Val Lys Leu Val Glu Ser Gly Gly Gly Leu Val
1               5                   10                  15

Lys Pro Gly Gly Ser Leu Lys Leu Ser Cys Ala Ala Ser Gly Phe Thr
            20                  25                  30

Phe Ser Arg Tyr Thr Met Ser Trp Val Arg Gln Thr Pro Glu Lys Arg
        35                  40                  45

Leu Glu Trp Val Ala Thr Ile Ser Asn Ser Gly Ser Tyr Thr Tyr Tyr
    50                  55                  60

Arg Asp Ser Val Lys Gly Arg Phe Thr Ile Ser Arg Asp Asn Ala Lys
65                  70                  75                  80

Asn Thr Leu Tyr Leu Gln Met Ser Ser Leu Lys Ser Glu Asp Thr Ala
                85                  90                  95

Met Tyr Tyr Cys Thr Arg Gly Ser Pro Trp Gly Gln Gly Thr Leu Val
            100                 105                 110

Thr Val Ser Ala Gly Gly Gly Gly Ser Gly Gly Gly Gly Ser Gly Gly
        115                 120                 125

Gly Gly Ser Asp Ile Gln Met Thr Gln Ser Pro Asp Ser Leu Ser Ala
```

```
    130                 135                 140

Ser Val Gly Glu Thr Val Thr Ile Thr Cys Gly Ala Ser Glu Asn Ile
145                 150                 155                 160

Tyr Gly Ala Leu Asn Trp Tyr Gln Arg Lys Gln Gly Lys Ser Pro Gln
                165                 170                 175

Leu Leu Ile Tyr Gly Ala Thr Lys Leu Ala Asp Gly Met Ser Ser Arg
            180                 185                 190

Phe Ser Gly Ser Gly Ser Asn Arg Gln Tyr Ser Leu Lys Ile Ser Ser
        195                 200                 205

Leu His Pro Asp Asp Val Ala Thr Tyr Tyr Cys Gln Asn Val Leu Ser
    210                 215                 220

Lys Pro Tyr Ala Phe Gly Gly Gly Thr Lys Leu Glu Ile Lys
225                 230                 235


<210> SEQ ID NO 172
<211> LENGTH: 247
<212> TYPE: PRT
<213> ORGANISM: Artificial Sequence
<220> FEATURE:
<223> OTHER INFORMATION: Synthetic

<400> SEQUENCE: 172

Glu Val Lys Leu Gln Gln Ser Gly Ala Asp Leu Ala Thr Pro Gly Ala
1               5                   10                  15

Ser Val Lys Leu Ser Cys Lys Ala Ser Gly Tyr Thr Phe Ser Thr Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala His
65                  70                  75                  80

Met Gln Leu Ser Ser Leu Ala Ser Glu Asp Ser Ala Val Tyr Tyr Cys
                85                  90                  95

Ala Arg Gly Gly Leu Tyr Tyr Gly Tyr Asp Ile Ala Tyr Trp Gly Gln
            100                 105                 110

Gly Thr Leu Val Thr Val Ser Ala Gly Gly Gly Gly Ser Gly Gly Gly
        115                 120                 125

Gly Ser Gly Gly Gly Gly Ser Asp Ile Leu Met Thr Gln Thr Pro Leu
    130                 135                 140

Ser Leu Pro Val Ser Leu Gly Asp Gln Ala Ser Ile Ser Cys Arg Ser
145                 150                 155                 160

Ser Gln Ser Ile Val His Ser Asn Gly Asn Thr Tyr Leu Glu Trp Tyr
                165                 170                 175

Leu Gln Lys Pro Gly Gln Ser Pro Lys Pro Leu Ile Lys Lys Val Ser
            180                 185                 190

Asn Arg Phe Ser Gly Val Pro Asp Arg Phe Ser Gly Ser Gly Ser Gly
        195                 200                 205

Thr Glu Phe Thr Leu Lys Ile Ser Arg Val Glu Ala Glu Asp Leu Gly
    210                 215                 220

Val Tyr Tyr Cys Phe Gln Gly Ser His Val Pro Phe Thr Phe Gly Ser
225                 230                 235                 240

Gly Thr Lys Leu Glu Ile Lys
                245
```

<210> SEQ ID NO 173
<211> LENGTH: 242
<212> TYPE: PRT
<213> ORGANISM: Artificial Sequence
<220> FEATURE:
<223> OTHER INFORMATION: Synthetic

<400> SEQUENCE: 173

```
Glu Val Lys Leu Val Glu Ser Gly Gly Gly Leu Val Gln Pro Gly Gly
1               5                   10                  15

Ser Leu Arg Leu Ser Cys Ser Ile Ser Gly Phe Thr Phe Thr Asp Tyr
            20                  25                  30

Tyr Met Asn Trp Val Arg Gln Ser Pro Gly Lys Ala Leu Glu Trp Leu
        35                  40                  45

Gly Phe Ile Arg Asn Lys Val Asn Gly Asp Thr Thr Glu Tyr Ser Ala
    50                  55                  60

Ser Val Lys Gly Arg Phe Thr Ile Ser Arg Asp Ile Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Asp Lys Gly Ile Ala Tyr Tyr Phe Asp Tyr Trp Gly
            100                 105                 110

Gln Gly Thr Thr Leu Thr Val Ser Ser Gly Gly Gly Gly Ser Gly Gly
        115                 120                 125

Gly Gly Ser Gly Gly Gly Gly Ser Gln Ile Val Leu Ser Gln Ser Pro
    130                 135                 140

Ala Ile Leu Phe Ala Ser Pro Gly Glu Lys Val Thr Met Thr Cys Arg
145                 150                 155                 160

Ala Ser Ser Ser Val Ser Tyr Ile His Trp Tyr Gln Gln Lys Pro Gly
                165                 170                 175

Ser Ser Pro Lys Pro Trp Ile His Gly Thr Ser Asn Leu Ala Ser Gly
            180                 185                 190

Val Pro Ala Arg Phe Ser Gly Ser Gly Ser Gly Thr Ser Tyr Ser Leu
        195                 200                 205

Thr Ile Ser Arg Met Glu Ala Glu Asp Ala Ala Thr Tyr Tyr Cys Gln
    210                 215                 220

Gln Trp Ser Ser Asn Leu Ser Thr Phe Gly Gly Gly Thr Lys Leu Glu
225                 230                 235                 240

Ile Lys
```

<210> SEQ ID NO 174
<211> LENGTH: 237
<212> TYPE: PRT
<213> ORGANISM: Artificial Sequence
<220> FEATURE:
<223> OTHER INFORMATION: Synthetic

<400> SEQUENCE: 174

```
Gln Val Gln Leu Lys Glu Ser Gly Pro Gly Leu Val Ala Pro Ser Gln
1               5                   10                  15

Asn Leu Ser Ile Thr Cys Thr Val Ser Gly Phe Ser Leu Thr Ser Tyr
            20                  25                  30

Ala Ile Asn Trp Val Arg Gln Pro Pro Gly Lys Gly Leu Glu Trp Leu
        35                  40                  45

Gly Ile Ile Trp Thr Gly Gly Gly Thr Asn Tyr Asn Ser Ala Leu Lys
    50                  55                  60

Ser Arg Leu Ser Ile Ser Lys Asp Asn Ser Lys Ser Gln Val Phe Leu
```

```
65                  70                  75                  80

Lys Met Asn Ser Leu Gln Thr Asp Asp Thr Ala Arg Tyr Tyr Cys Ala
                85                  90                  95

Ser Gly Val Tyr Tyr Phe Asp Tyr Trp Gly Leu Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Ser His Lys Phe Met Ser Thr Ser
    130                 135                 140

Val Gly Asp Arg Val Ser Ile Thr Cys Lys Ala Ser Gln Asp Val Thr
145                 150                 155                 160

Thr Ala Val Ala Trp Tyr Gln Gln Lys Pro Gly Gln Ser Pro Lys Val
                165                 170                 175

Leu Ile Phe Trp Ala Ser Thr Arg His Thr Gly Val Pro Asp Arg Phe
            180                 185                 190

Thr Gly Ser Gly Ser Gly Thr Asp Tyr Thr Leu Thr Ile Ser Ser Val
        195                 200                 205

Gln Ala Glu Asp Leu Ala Leu Tyr Tyr Cys Gln Gln Tyr Tyr Arg Thr
    210                 215                 220

Pro Arg Thr Phe Gly Gly Gly Thr Lys Leu Glu Ile Lys
225                 230                 235


<210> SEQ ID NO 175
<211> LENGTH: 243
<212> TYPE: PRT
<213> ORGANISM: Artificial Sequence
<220> FEATURE:
<223> OTHER INFORMATION: Synthetic

<400> SEQUENCE: 175

Glu Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Asn Asp Tyr
            20                  25                  30

Asn Met Asp Tyr Leu Lys Gln Ser His Gly Lys Ser Leu Glu Trp Ile
        35                  40                  45

Gly Asp Ile Asn Pro Asn Tyr Asp Ser Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Asp Tyr Asp Gly Arg Arg Gly Ala Trp Phe Ser Tyr Trp
            100                 105                 110

Gly Gln Gly Thr Leu Val Thr Val Ser Ala Gly Gly Gly Gly Ser Gly
        115                 120                 125

Gly Gly Gly Ser Gly Gly Gly Gly Ser Gln Ile Val Leu Thr Gln Ser
    130                 135                 140

Pro Ala Leu Met Ser Ala Ser Pro Gly Glu Lys Val Thr Val Thr Cys
145                 150                 155                 160

Thr Ala Ser Ser Ser Val Ser Tyr Met Tyr Trp Tyr Gln Gln Lys Pro
                165                 170                 175

Arg Ser Ser Pro Lys Pro Trp Ile Tyr Leu Thr Ser Asn Leu Ala Ser
            180                 185                 190

Gly Val Pro Thr Arg Phe Ser Gly Ser Gly Ser Gly Thr Ser Tyr Ser
```

```
        195                 200                 205

Leu Thr Ile Ser Ser Met Glu Ala Glu Asp Ala Ala Thr Tyr Tyr Cys
    210                 215                 220

Gln Gln Trp Asp Ser Asn Pro Leu Thr Phe Gly Ala Gly Thr Lys Leu
225                 230                 235                 240

Glu Leu Lys


<210> SEQ ID NO 176
<211> LENGTH: 238
<212> TYPE: PRT
<213> ORGANISM: Artificial Sequence
<220> FEATURE:
<223> OTHER INFORMATION: Synthetic

<400> SEQUENCE: 176

Asp Ile Gln Met Thr Gln Ser Pro Asp Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Lys Leu Ala Asp Gly Met Ser Ser Arg Phe Ser Gly
    50                  55                  60

Ser Gly Ser Asn Arg Gln Tyr Ser Leu Lys Ile Ser Ser Leu His Pro
65                  70                  75                  80

Asp Asp Val Ala Thr Tyr Tyr Cys Gln Asn Val Leu Ser Lys Pro Tyr
                85                  90                  95

Ala Phe Gly Gly Gly Thr Lys Leu Glu Ile Lys Gly Gly Gly Gly Ser
            100                 105                 110

Gly Gly Gly Gly Ser Gly Gly Gly Gly Ser Gly Val Gln Cys Asp Val
        115                 120                 125

Lys Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Arg Tyr Thr Met
145                 150                 155                 160

Ser Trp Val Arg Gln Thr Pro Glu Lys Arg Leu Glu Trp Val Ala Thr
                165                 170                 175

Ile Ser Asn Ser Gly Ser Tyr Thr Tyr Tyr Arg Asp Ser Val Lys Gly
            180                 185                 190

Arg Phe Thr Ile Ser Arg Asp Asn Ala Lys Asn Thr Leu Tyr Leu Gln
        195                 200                 205

Met Ser Ser Leu Lys Ser Glu Asp Thr Ala Met Tyr Tyr Cys Thr Arg
    210                 215                 220

Gly Ser Pro Trp Gly Gln Gly Thr Leu Val Thr Val Ser Ala
225                 230                 235


<210> SEQ ID NO 177
<211> LENGTH: 247
<212> TYPE: PRT
<213> ORGANISM: Artificial Sequence
<220> FEATURE:
<223> OTHER INFORMATION: Synthetic

<400> SEQUENCE: 177

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
```

```
            20                  25                  30

Asn Gly Asn Thr Tyr Leu Glu Trp Tyr Leu Gln Lys Pro Gly Gln Ser
        35                  40                  45

Pro Lys Pro Leu Ile Lys Lys Val Ser Asn Arg Phe Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Gly Gly Gly Gly Ser Gly Gly Gly Gly Ser Gly Gly Gly Gly Ser Glu
        115                 120                 125

Val Lys Leu Gln Gln Ser Gly Ala Asp Leu Ala Thr Pro Gly Ala Ser
    130                 135                 140

Val Lys Leu Ser Cys Lys Ala Ser Gly Tyr Thr Phe Ser Thr Tyr Trp
145                 150                 155                 160

Met Gln Trp Val Lys Gln Arg Pro Gly Gln Gly Leu Glu Trp Ile Gly
                165                 170                 175

Thr Ile Tyr Pro Gly Asp Gly Asp Thr Arg Tyr Thr Gln Lys Phe Lys
            180                 185                 190

Gly Lys Ala Thr Leu Thr Ala Asp Lys Ser Ser Ser Thr Ala His Met
        195                 200                 205

Gln Leu Ser Ser Leu Ala Ser Glu Asp Ser Ala Val Tyr Tyr Cys Ala
    210                 215                 220

Arg Gly Gly Leu Tyr Tyr Gly Tyr Asp Ile Ala Tyr Trp Gly Gln Gly
225                 230                 235                 240

Thr Leu Val Thr Val Ser Ala
                245


<210> SEQ ID NO 178
<211> LENGTH: 242
<212> TYPE: PRT
<213> ORGANISM: Artificial Sequence
<220> FEATURE:
<223> OTHER INFORMATION: Synthetic

<400> SEQUENCE: 178

Gln Ile Val Leu Ser Gln Ser Pro Ala Ile Leu Phe Ala Ser Pro Gly
1               5                   10                  15

Glu Lys Val Thr Met Thr Cys Arg Ala Ser Ser Ser Val Ser Tyr Ile
            20                  25                  30

His Trp Tyr Gln Gln Lys Pro Gly Ser Ser Pro Lys Pro Trp Ile His
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Asn Leu Ser Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Gly Ser Glu Val Lys Leu Val Glu Ser
        115                 120                 125

Gly Gly Gly Leu Val Gln Pro Gly Gly Ser Leu Arg Leu Ser Cys Ser
```

```
    130                 135                 140

Ile Ser Gly Phe Thr Phe Thr Asp Tyr Tyr Met Asn Trp Val Arg Gln
145                 150                 155                 160

Ser Pro Gly Lys Ala Leu Glu Trp Leu Gly Phe Ile Arg Asn Lys Val
                165                 170                 175

Asn Gly Asp Thr Thr Glu Tyr Ser Ala Ser Val Lys Gly Arg Phe Thr
            180                 185                 190

Ile Ser Arg Asp Ile Ser Gln Ser Ile Leu Tyr Leu Gln Met Asn Thr
        195                 200                 205

Leu Arg Thr Glu Asp Ser Ala Thr Tyr Tyr Cys Ala Arg Asp Lys Gly
    210                 215                 220

Ile Ala Tyr Tyr Phe Asp Tyr Trp Gly Gln Gly Thr Thr Leu Thr Val
225                 230                 235                 240

Ser Ser


<210> SEQ ID NO 179
<211> LENGTH: 237
<212> TYPE: PRT
<213> ORGANISM: Artificial Sequence
<220> FEATURE:
<223> OTHER INFORMATION: Synthetic

<400> SEQUENCE: 179

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Thr Ala
            20                  25                  30

Val Ala Trp Tyr Gln Gln Lys Pro Gly Gln Ser Pro Lys Val Leu Ile
        35                  40                  45

Phe Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln Tyr Tyr Arg Thr Pro Arg
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Gly Ser Gln Val Gln Leu Lys Glu
        115                 120                 125

Ser Gly Pro Gly Leu Val Ala Pro Ser Gln Asn Leu Ser Ile Thr Cys
    130                 135                 140

Thr Val Ser Gly Phe Ser Leu Thr Ser Tyr Ala Ile Asn Trp Val Arg
145                 150                 155                 160

Gln Pro Pro Gly Lys Gly Leu Glu Trp Leu Gly Ile Ile Trp Thr Gly
                165                 170                 175

Gly Gly Thr Asn Tyr Asn Ser Ala Leu Lys Ser Arg Leu Ser Ile Ser
            180                 185                 190

Lys Asp Asn Ser Lys Ser Gln Val Phe Leu Lys Met Asn Ser Leu Gln
        195                 200                 205

Thr Asp Asp Thr Ala Arg Tyr Tyr Cys Ala Ser Gly Val Tyr Tyr Phe
    210                 215                 220

Asp Tyr Trp Gly Leu Gly Thr Thr Leu Thr Val Ser Ser
225                 230                 235


<210> SEQ ID NO 180
```

```
<211> LENGTH: 243
<212> TYPE: PRT
<213> ORGANISM: Artificial Sequence
<220> FEATURE:
<223> OTHER INFORMATION: Synthetic

<400> SEQUENCE: 180

Gln Ile Val Leu Thr Gln Ser Pro Ala Leu Met Ser Ala Ser Pro Gly
1               5                   10                  15

Glu Lys Val Thr Val Thr Cys Thr Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Thr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asp Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Gly Ser Glu Val Lys Leu Gln Glu Ser
        115                 120                 125

Gly Ala Glu Leu Val Lys Pro Gly Ala Ser Val Lys Ile Ser Cys Lys
    130                 135                 140

Ala Ser Gly Tyr Thr Phe Asn Asp Tyr Asn Met Asp Tyr Leu Lys Gln
145                 150                 155                 160

Ser His Gly Lys Ser Leu Glu Trp Ile Gly Asp Ile Asn Pro Asn Tyr
                165                 170                 175

Asp Ser Thr Ile Tyr Asn Gln Lys Phe Lys Gly Lys Ala Thr Leu Thr
            180                 185                 190

Val Asp Lys Ser Ser Ser Thr Ala Tyr Met Glu Leu Arg Ser Leu Thr
        195                 200                 205

Ser Glu Asp Ser Ala Val Tyr Tyr Cys Ala Arg Arg Asp Tyr Asp Gly
    210                 215                 220

Arg Arg Gly Ala Trp Phe Ser Tyr Trp Gly Gln Gly Thr Leu Val Thr
225                 230                 235                 240

Val Ser Ala


<210> SEQ ID NO 181
<211> LENGTH: 24
<212> TYPE: DNA
<213> ORGANISM: Artificial Sequence
<220> FEATURE:
<223> OTHER INFORMATION: 8His fragment

<400> SEQUENCE: 181

caccatcacc atcaccatca ccat                                              24
```

SINGLE-CHAIN ANTIBODY SPECIFICALLY BINDING MG7, HIGHLY GLYCOSYLATED CEA AND USE THEREOF IN DETECTION AND THERAPY

CROSS-REFERENCE TO RELATED APPLICATIONS

This application is a 371(c) National Phase of international Appl. No. PCT/CN2017/094755, filed Jul. 27, 2017, which claims priority to Chinese Appl. No. CN 201610614701.3, filed Jul. 29, 2016, the disclosures of each of which are hereby incorporated by reference in their entireties.

SEQUENCE LISTING DISCLOSURE

This application includes as part of its disclosure a biological sequence listing which is being concurrently submitted through EFS-Web. Said biological sequence listing is contained in a file named "2954060o003201.txt" which was created Dec. 30, 2021, and has a size of 213,510 bytes, and is hereby incorporated by reference in its entirety.

TECHNICAL FIELD

The present invention relates to the field of tumor immunotherapy, and more particularly, the present invention relates to a glycosylated CEA-specific single-chain antibody, and to the field of transgenic modified adoptive T lymphocyte therapy for a tumor that overexpresses glycosylated CEA.

BACKGROUND ART

The incidence of gastric cancer ranks first in the digestive tract malignant tumors in China, and second in the world. The annual deaths account for about 24% of the malignant tumor deaths, and the five-year survival rate is only about 27%. The diagnosis of gastric cancer patients is often late, so the prognosis is extremely poor. There is no effective target therapy for gastric cancer. CEA (carcinoembryonic antigen) is a membrane-bound protein, and generally expressed in fetal liver, intestine and pancreas. Normally, it is secreted into the intestine, and its serum level is low. When the cell is cancerous, the serum level is elevated, which has auxiliary significance for the early diagnosis of pancreatic cancer and colon cancer, and has certain reference value for tumor spread, curative effect, recurrence and prognosis. Professor Fan Daiming from the Fourth Military Medical University found that the glycosylated CEA is highly sensitive and specific to a variety of digestive tract cancers. Clinical studies have shown that the positive rate of glycosylated CEA in gastric cancer tissues is above 80%, the positive rate in colon cancer tissues is above 40%, the positive rate in gastric precancerous lesions is above 30%, and the positive rate in esophageal cancer tissues is 18% or more. At the same time, the results of clinical trials showed that the positive rate of serum glycosylated CEA in 28 patients with gastric cancer decreased significantly in comparison with that before surgery, suggesting that there is a close relationship between glycosylated CEA and gastric cancer (Gadler et al., Int J Cancer 25 (1): 91-4, 1980).

At present, the emerging chimeric antigen receptor T cell (CAR-T) with targeted adoptive cell therapy technology plays an important role in the treatment of various malignant tumors. CAR-T is a fusion of a tumor-associated antigen (TAA)-specific recognition peptide, such as a single-chain antibody, a specific receptor, with a T cell activation signal such as CD3zeta, and the fusion protein is specifically expressed on T cell surface by a lentivirus or the like, allowing the modified T cell to specifically recognize and kill tumor cells, being independent of major histocompatibility antigen (MHC), and avoiding tumor immune escape due to MHC deletion.

The chimeric antigen receptor includes an extracellular antigen targeting and recognizing region, a hinge region, a transmembrane region, and an intracellular costimulatory signaling region. The antigen recognizing region is mostly a single-chain antibody or a specific receptor, which ensures that the modified T cell can specifically recognize the target cell and be activated to specifically kill the target cell; the hinge region generally adopts CD8α, CD28ECD, IgG Fc fragment and the like, which ensures that the T cell contacts the target cell and affects the T cell action; and the intracellular signal region adopts an immunoreceptor tyrosine activation motif (ITAM), for example CD3zeta and costimulatory signal such as CD28, CD137, CD27, ICOS, OX40, DAP10, etc. (Sadelain et al., Cancer Discov 3(4): 388-98, 2013).

Although CAR-T has shown good application value in the treatment of hematological malignancies, CAR-T often does not achieve the expected results in the treatment of solid tumors. Even in some clinical studies, CAR-T may exhibit toxicity due to off-target effects. The important reason is that there is often no effective and specific target in solid tumors. For many tumor-associated antigens, there is often a certain degree of expression in normal tissues. For example, HER2 is an important target for malignant tumors such as malignant glioma and breast cancer, but in the CAR-T clinical trial for HER2 target, the patient suffered pulmonary failure after CAR-T re-infusion, and "cytokine storm" was triggered and caused the death of patients in a short period of time. Therefore, finding a highly specific and sensitive target in solid tumors is a key point in the application of CAR-T treatments in solid tumors (Morgan et al., Mol Ther 18(4): 843-51, 2010).

NK cells are lymphocytes that express CD16 and CD56 and are important components in innate immunity. NK cells can kill MHC-deficient target cells. Compared with T cells, NK cells do not express T-cell receptors and thus do not undergo graft versus host response (GVHD). NK cell activation is in the equilibrium state of signals for KAR (Killer Activation Receptor) and KIR (Killer Inhibition Receptor). The main MR ligand in vivo is MHC. For mismatch or deletion of MR ligand, it will cause the activation of NK cells. CAR-NK technology is an emerging technology that uses CAR structure expression on the surface of NK cells or NK cell lines (such as NK92) for the treatment of cancers, which advantage is that NK cells do not secrete IL6, NK cells have a very short circulating half-life in the periphery blood, NK cells have a high transfection efficiency (non-viral vector), and NK cell lines can be cultured on a large scale at GMP level. The CAR structure expression on the surface of NK cells or NK cell lines can endow NK cells with targeting ability. At the same time, in CAR-NK allograft, the mismatch of MR receptor may enhance the activation of NK cells to achieve better tumor elimination. The circulation time of NK cell lines in vivo is very short, thus providing safety considerations (Han et al., Sci Rep 5: 11483, 2015).

SUMMARY OF THE INVENTION

In a first aspect, the invention provides a chimeric antigen receptor (CAR), wherein the CAR comprises:

i) an antigen-binding domain targeting a glycosylated CEA;

ii) a transmembrane domain, and iii) an intracellular signaling domain comprising a costimulatory domain, wherein the antigen-binding domain targeting the glycosylated CEA comprises a heavy chain variable region and a light chain variable region, characterized in that the heavy chain variable region and the light chain variable region are selected from any one of the following combinations:

a. the heavy chain variable region comprises one or more CDRs as described below: CDR-H1 set forth in SEQ ID NO: 1, CDR-H2 set forth in SEQ ID NO: 2, or CDR-H3 set forth in SEQ ID NO: 3; and the light chain variable region comprises one or more CDRs as described below: CDR-L1 set forth in SEQ ID NO: 4, CDR-L2 set forth in SEQ ID NO: 5, or CDR-L3 set forth in SEQ ID NO: 6;

b. the heavy chain variable region comprises one or more CDRs as described below: CDR-H1 set forth in SEQ ID NO:7, CDR-H2 set forth in SEQ ID NO:8, or CDR-H3 set forth in SEQ ID NO:9; and the light chain variable region comprises one or more CDRs as described below: CDR-L1 set forth in SEQ ID NO: 10, CDR-L2 set forth in SEQ ID NO: 11, or CDR-L3 set forth in SEQ ID NO: 12;

c. the heavy chain variable region comprises one or more CDRs as described below: CDR-H1 set forth in SEQ ID NO: 13, CDR-H2 set forth in SEQ ID NO: 14, or CDR-H3 set forth in SEQ ID NO: 15; and the light chain variable region comprises one or more CDRs as described below: CDR-L1 set forth in SEQ ID NO: 16, CDR-L2 set forth in SEQ ID NO: 17, or CDR-L3 set forth in SEQ ID NO: 18;

d. the heavy chain variable region comprises one or more CDRs as described below: CDR-H1 set forth in SEQ ID NO: 19, CDR-H2 set forth in SEQ ID NO: 20, or CDR-H3 set forth in SEQ ID NO: 21; and the light chain variable region comprises one or more CDRs as described below: CDR-L1 set forth in SEQ ID NO: 22, CDR-L2 set forth in SEQ ID NO: 23, or CDR-L3 set forth in SEQ ID NO: 24; or e. the heavy chain variable region comprises one or more CDRs as described below: CDR-H1 set forth in SEQ ID NO: 25, CDR-H2 set forth in SEQ ID NO: 26, or CDR-H3 set forth in SEQ ID NO: 27; and the light chain variable region comprises one or more CDRs as described below: CDR-L1 set forth in SEQ ID NO: 28, CDR-L2 set forth in SEQ ID NO: 29, or CDR-L3 set forth in SEQ ID NO:30.

In a specific embodiment, the heavy chain variable region and the light chain variable region are selected from any one of the following combinations: a) the heavy chain variable region comprises a polypeptide fragment set forth in SEQ ID NO: 31, and the light chain variable region comprises a polypeptide fragment set forth in SEQ ID NO: 32; b) the heavy chain variable region comprises a polypeptide fragment set forth in SEQ ID NO: 33, and the light chain variable region comprises a polypeptide fragment set forth in SEQ ID NO: 34; c) the heavy chain variable region comprises a polypeptide fragment set forth in SEQ ID NO: 35, and the light chain variable region comprises a polypeptide fragment set forth in SEQ ID NO: 36; d) the heavy chain variable region comprises a polypeptide fragment set forth in SEQ ID NO: 37, and the light chain variable region comprises a polypeptide fragment set forth in SEQ ID NO: 38; or e) the heavy chain variable region comprises a polypeptide fragment set forth in SEQ ID NO: 39, and the light chain variable region comprises a polypeptide fragment set forth in SEQ ID NO:40.

In another embodiment, the antigen-binding domain of the invention is a single-chain antibody that specifically recognizes a glycosylated CEA, the amino acid sequence of the single-chain antibody is set forth in any one of SEQ ID NOs: 171-180; most preferably, the amino acid sequence of the single-chain antibody is SEQ ID NO: 173 or SEQ ID NO: 178.

Preferably, in the chimeric antigen receptor of the present invention, the transmembrane domain comprises CD8α and/or CD28, and the intracellular signaling domain comprises one or more of CD28, CD137, and CD3zeta, wherein the CD8α hinge region is encoded by the sequence set forth in SEQ ID NO: 52, the CD8α transmembrane region is encoded by the sequence set forth in SEQ ID NO:54, the CD28 hinge region is encoded by the sequence set forth in SEQ ID NO:53, the CD28 transmembrane region is encoded by the sequence set forth in SEQ ID NO: 55, the CD28 costimulatory domain is encoded by the sequence set forth in SEQ ID NO:56, the CD137 costimulatory domain is encoded by the sequence set forth in SEQ ID NO:57, and CD3zeta is encoded by the sequence set forth in SEQ ID NO:58.

In another aspect, the invention provides a nucleic acid molecule encoding a chimeric antigen receptor of the invention.

In another aspect, the invention provides a cell expressing a chimeric antigen receptor of the invention, preferably the cell is selected from the group consisting of a T cell, an NK cell and a B cell, more preferably the cell is a T cell.

In another aspect, the invention provides a lymphocyte expressing a chimeric antigen receptor, the chimeric antigen receptor comprises an extracellular targeted recognition antigen sequence, a hinge region sequence, a transmembrane region sequence, and an intracellular signal sequence, where are connected in order. Wherein the extracellular recognition antigen sequence is a single-chain antibody that specifically recognizes the glycosylated CEA as described in the present invention, which is defined as above. The hinge region is selected from the group consisting of CD8α, CD28ECD, and IgG Fc fragments. The intracellular signal region may employ an immunoreceptor tyrosine activation motif (ITAM) such as CD3zeta and costimulatory signals such as CD28, CD137, CD27, ICOS, OX40, DAP10. In one embodiment, the hinge region sequence in the chimeric antigen receptor comprises CD8α or CD28, encoded by the sequence set forth in SEQ ID NO: 52 or SEQ ID NO: 53, respectively; the transmembrane region sequence in the chimeric antigen receptor comprises CD8α or CD28, encoded by the sequence set forth in SEQ ID NO: 54 or SEQ ID NO: 55, respectively; the intracellular signal sequence in the chimeric antigen receptor comprises CD28, CD137, CD3zeta and combination thereof, CD28 is encoded by the sequence set forth in SEQ ID NO: 56, CD137 is encoded by the sequence set forth in SEQ ID NO: 57, and CD3zeta is encoded by the sequence set forth in SEQ ID NO:58. In one embodiment, the lymphocyte may be a T cell, a B cell or a NK cell, and the like. In a specific embodiment, the lymphocyte is a T cell and the chimeric antigen receptor is expressed as follows:

scFv-CD8α-CD137-CD3zeta,
scFv-CD28-CD28-CD137-CD3zeta,
scFv-CD28-CD28-CD3zeta.

In a preferred embodiment, the chimeric antigen receptor as constructed in the invention has a sequence set forth in SEQ ID NOs: 69-128.

When the antigen-binding domain of the chimeric antigen receptor binds its corresponding antigen, the cell comprising the chimeric antigen receptor exhibits anti-tumor immunity.

The present invention constructs a series of single-chain antibodies against glycosylated CEA. The single-chain antibodies of the present invention can be used for detection and treatment of tumors such as gastric cancer, colorectal cancer, and esophageal cancer. These single-chain antibodies can be expressed on the surface of lymphocytes such as T cells and NK cells to construct and form chimeric antigen receptor T cells or chimeric antigen receptor NK cells against glycosylated CEA, for specific killing glycosylated CEA expression-positive cells and tissues.

In a second aspect, the present invention provides single-chain antibodies against glycosylated CEA, which are FM2, FM3, FM4, FM5, FM6, respectively, wherein the CDR sequences of their heavy chain variable regions and light chain variable regions are SEQ ID NO: 1-30, their coding nucleotides are SEQ ID NO: 129-158, respectively, see the sequence listing.

The present invention provides single-chain antibodies against glycosylated CEA, which are FM2, FM3, FM4, FM5, FM6, respectively, and their heavy chain variable regions are SEQ ID NO: 31, SEQ ID NO: 33, SEQ ID NO: 35. SEQ ID NO: 37 or SEQ ID NO: 39; their light chain variable regions are SEQ ID NO: 32, SEQ ID NO: 34, SEQ ID NO: 36, SEQ ID NO: 38 or SEQ ID NO: 40, respectively. In one embodiment, the invention provides a single-chain antibody against glycosylated CEA, which is arranged in the form of VH-Linker-VL or VL-Linker-VH, wherein VH is selected from the heavy chain variable region sequences described above, VL is selected from the light chain variable region sequences described above. In a preferred embodiment, the Linker, i.e., linker peptide, is the sequence set forth in SEQ ID NO:41.

The invention provides an isolated nucleic acid molecule encoding the single-chain antibody of the invention. In one embodiment, the nucleotide sequence encoding the heavy chain variable region of the single-chain antibody is SEQ ID NO: 42, SEQ ID NO: 44, SEQ ID NO: 46, SEQ ID NO: 48 or SEQ ID NO: 50. In one embodiment, the nucleotide sequence encoding the light chain variable region of the single-chain antibody is SEQ ID NO: 43, SEQ ID NO: 45, SEQ ID NO: 47, SEQ ID NO: 49 or SEQ ID NO: 51.

The invention also provides a vector comprising a nucleic acid sequence encoding a chimeric antigen receptor. In a specific embodiment, the vector is pGC-EIF1α-MCS (CV185, Genechem) and pGC-EIF1α-MCS-2A-EGFP (CV178, Genechem).

A use of the chimeric antigen receptor and the single-chain antibody according to the present invention in the manufacture of a reagent for diagnosing a tumor or a medicament for treating a tumor, preferably wherein the tumor is a digestive tract tumor, more preferably selected from the group consisting of gastric cancer, colorectal cancer, esophageal cancer.

The invention also provides a method of providing anti-tumor immunity in a mammal. In one embodiment, the method comprises administering to the mammal an effective amount of the chimeric antigen receptor T cell of the invention, thereby providing anti-tumor immunity in the mammal.

The invention also comprises a method of treating a mammal having a disease, disorder or condition associated with an elevated tumor antigen expression, for example treatment of a gastrointestinal tumor with high expression of CEA. In one embodiment, the method comprises administering to the mammal an effective amount of the chimeric antigen receptor T cell of the invention, thereby treating a tumor in the mammal.

The invention also comprises a method of diagnosing a disease, disorder, or condition associated with an elevated tumor antigen expression, for example diagnosing a digestive tract tumor with high CEA expression. In one embodiment, the method comprises expression of an amount of glycosylated CEA for detecting a tumor and a surrounding tissue of the tumor.

SPECIFIC MODELS FOR CARRYING OUT THE INVENTION

Figure 1:
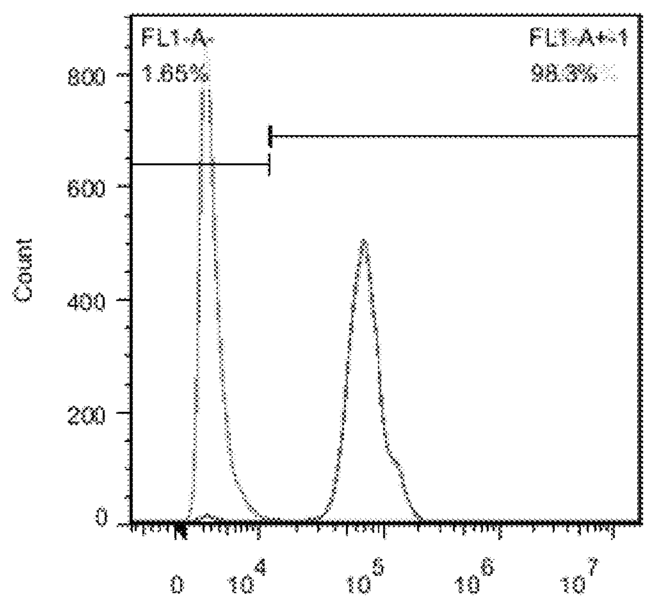
FIG. 1. Detection of CEA expression in SW620-CEA by flow cytometry.
Figure 2:
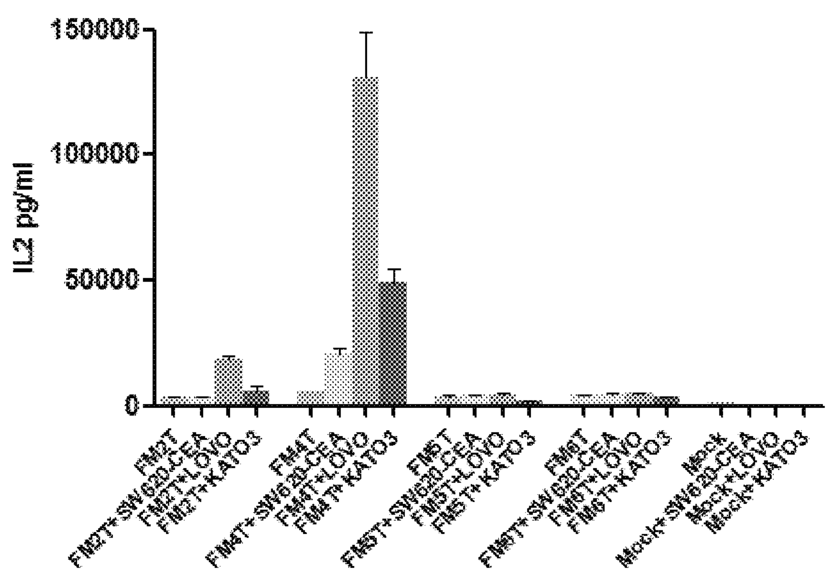
FIG. 2. $FM2_{(VL \to VH)}$, $FM4_{(VL \to VH)}$, $FM5_{(VL \to VH)}$, $FM6_{(VL \to VH)}$ were designed according to the structure scFv-CD8α-CD137-CD3zeta and infected human T cells as lentivirus, cultured until day 10, incubated with the target cells (SW620-CEA, LOVO, KATO3) in the figure for 16 hours and IL2 release was measured.
Figure 3:
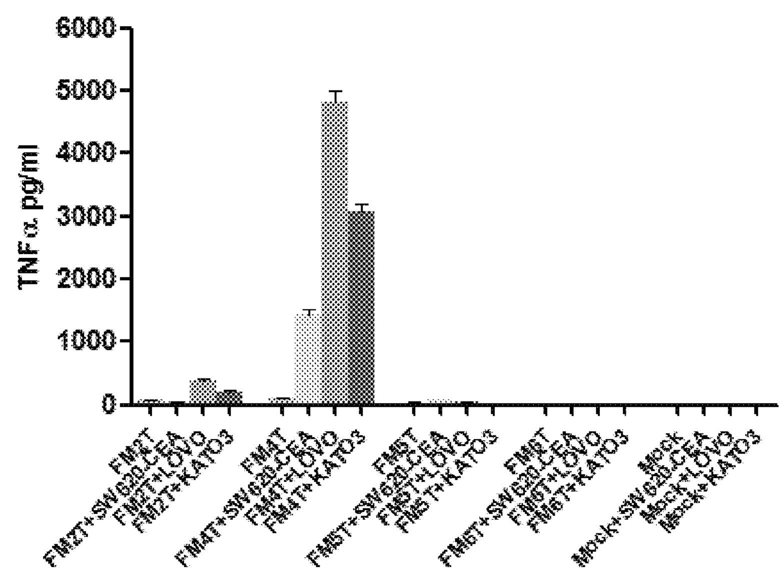
FIG. 3. $FM2_{(VL \to VH)}$, $FM4_{(VL \to VH)}$, $FM5_{(VL \to VH)}$, $FM6_{(VL \to VH)}$ were designed according to the structure scFv-CD8α-CD137-CD3zeta and infected human T cells as lentivirus, cultured until day 10, incubated with the target cells (SW620-CEA, LOVO, KATO3) in the figure for 16 hours and TNFα release was measured.
Figure 4:
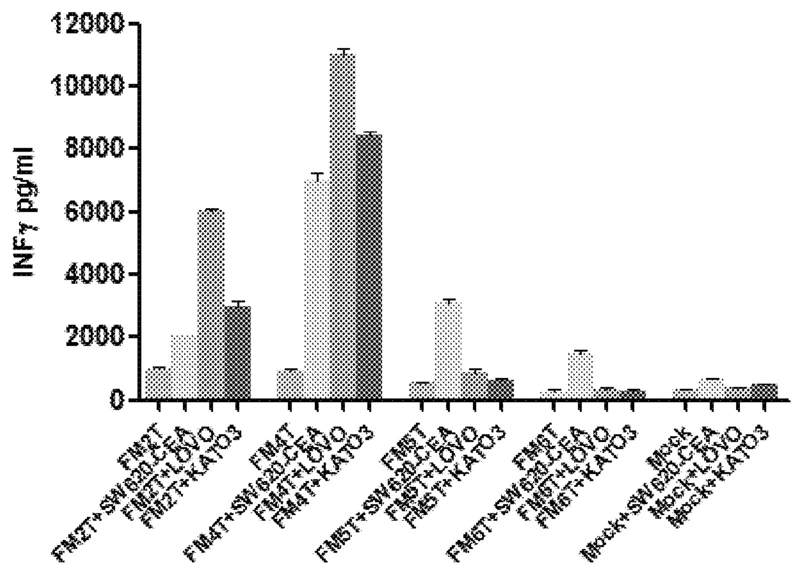
FIG. 4. $FM2_{(VL \to VH)}$, $FM4_{(VL \to VH)}$, $FM5_{(VL \to VH)}$, $FM6_{(VL \to VH)}$ were designed according to the structure scFv-CD8α-CD137-CD3zeta and infected human T cells as lentivirus, cultured until day 10, incubated with the target cells (SW620-CEA, LOVO, KATO3) in the figure for 16 hours and INFγ release was measured.
Figure 5:
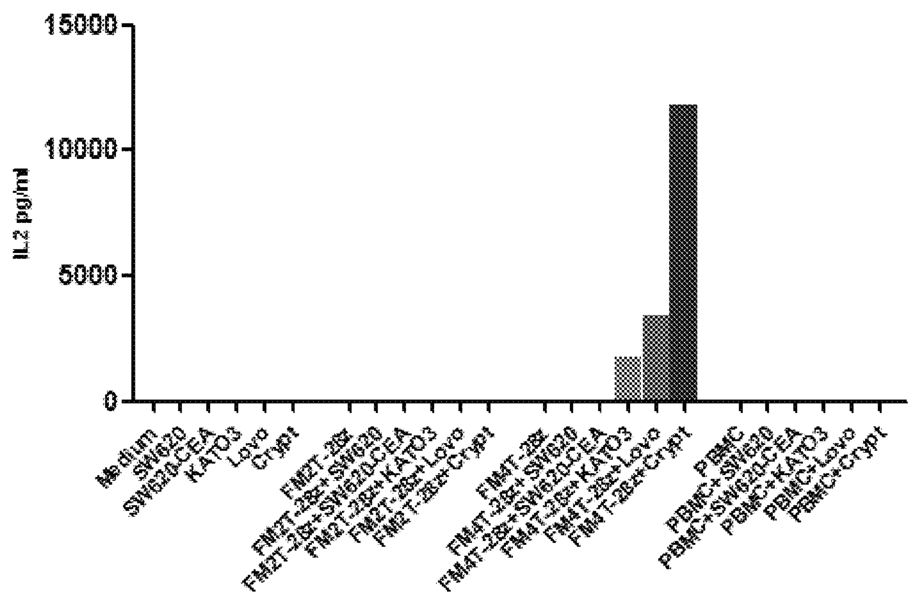
FIG. 5. $FM2_{(VL \to VH)}$, $FM4_{(VL \to VH)}$ were designed according to the structure scFv-CD28-CD28-CD3zeta and infected human T cells as lentivirus, cultured until day 10, incubated with the target cells (SW620, SW620-CEA, LOVO, KATO3, CRYPT) in the figure for 16 hours and IL2 release was measured.
Figure 6:
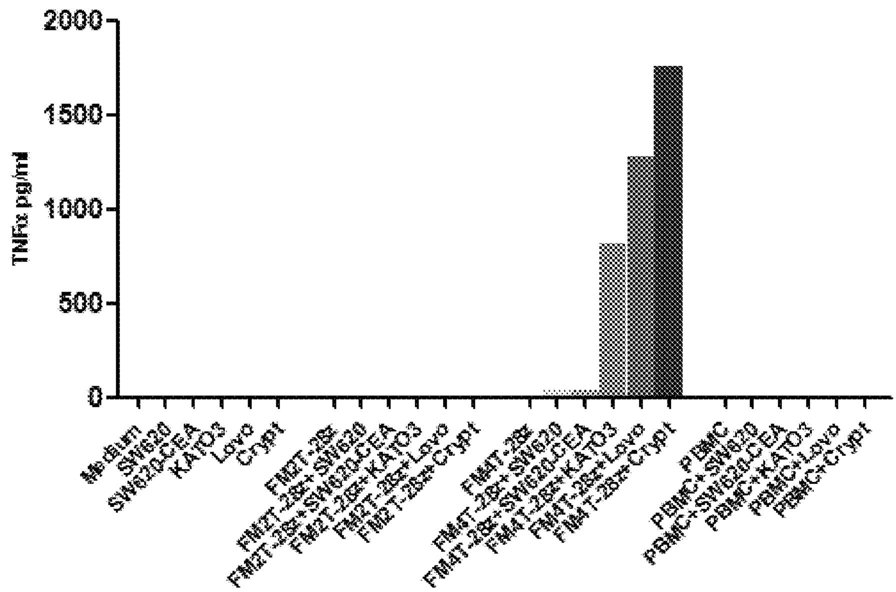
FIG. 6. $FM2_{(VL \to VH)}$, $FM4_{(VL \to VH)}$ were designed according to the structure scFv-CD28-CD28-CD3zeta and infected human T cells as lentivirus, cultured until day 10, incubated with the target cells (SW620, SW620-CEA, LOVO, KATO3, CRYPT) in the figure for 16 hours and TNFα release was measured.
Figure 7:
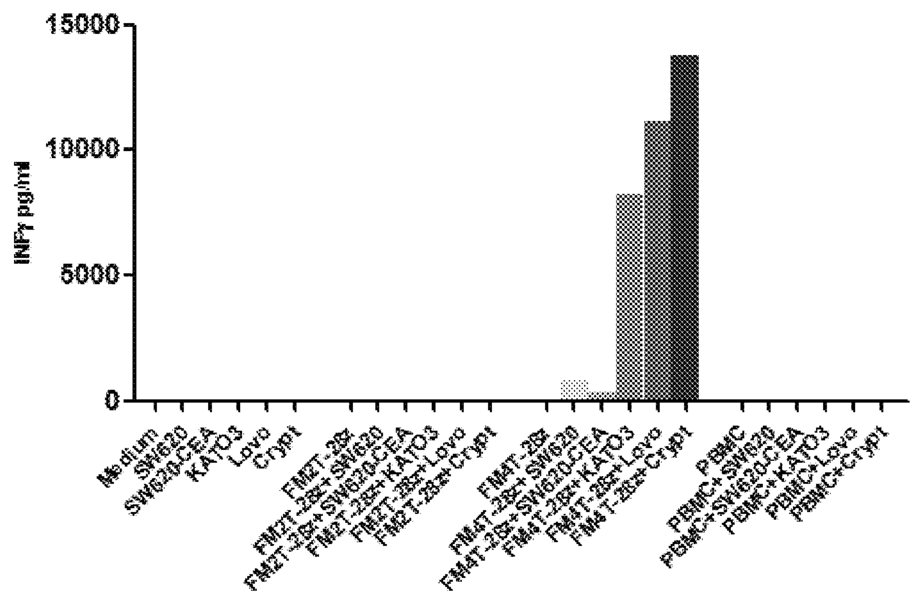
FIG. 7. $FM2_{(VL \to VH)}$, $FM4_{(VL \to VH)}$ were designed according to the structure scFv-CD28-CD28-CD3zeta and infected human T cells as lentivirus, cultured until day 10, incubated with the target cells (SW620, SW620-CEA, LOVO, KATO3, CRYPT) in the figure for 16 hours and INFγ release was measured.

Firstly, certain terms are defined so that the invention can be more readily understood. All technical and scientific terms used herein have the same meaning as commonly understood by one of ordinary skill in the art to which the invention belongs, unless otherwise indicated. Although methods and materials similar or equivalent to those described herein can be used in the practice or testing of the present invention, suitable methods and materials are described below. All publications, patent applications, patents, and other references cited herein are hereby incorporated by reference in their entirety herein. In case of conflict, the present specification (including definitions) shall prevail. In addition, the materials, methods, and examples are illustrative only and not limiting.

Single-Chain Antibody

As used herein, the "single-chain antibody (single-chain Fv, scFv)" is a recombinant protein formed by linking a heavy chain variable region (VH) and a light chain variable region (VL) of an immunoglobulin through a ligation peptide, which is the smallest antibody fragment with a complete antigen binding site. Human immunoglobulin (Ig) comprises five subtypes of IgA, IgD, IgM, IgE and IgG, of which IgG accounts for 75% of human immunoglobulin; IgG is a "Y" type antibody structure formed by two heavy chain IgH and two light chain IgL via interchain disulfide bonds; wherein IgH comprises a heavy chain variable region (VH) and a constant region (Constant Region); IgL comprises a light chain variable region (VL) and a constant region (Constant Region). The diversity of VH and VL is the basis for the binding of immunoglobulins to antigens. VH and VL are composed of a frame region (FR) and a complementary determining region (CDR), the CDR regions are highly variable and determine the specific binding of antigens and antibodies; wherein VH comprises three CDR regions, designated CDRH1, CDRH2, CDRH3; VL comprises three CDR regions, designated CDRL1, CDRL2, CDRL3.

The invention also comprises the variants, derivatives and analogs of the single-chain antibodies. As used in the text, the terms "variant", "derivative" and "analog" refer to a polypeptide that substantially retains the same biological function or activity of the single-chain antibody of the invention. The polypeptide variant, derivative or analog of the invention can be (i) a polypeptide in which one or more conservative or non-conservative amino acid residues (preferably conservative amino acid residues) are substituted, and such substituted amino acid residues may or may not be encoded by genetic codes, or (ii) a polypeptide in which one or more amino acid residues have substituent groups, or (iii) a polypeptide which is formed by fusing an additional amino acid sequence into the polypeptide sequence (such as a leader sequence or a secretory sequence or a sequence or polypeptide sequence used to purify the polypeptide, or a fusion polypeptide). These variants, derivatives and analogs are within the purview of those skilled in the art in accordance with the definitions herein.

A "single-chain antibody" of the invention refers to a polypeptide that specifically binds to a glycosylated CEA. The term also comprises variant forms having a polypeptide sequence capable of specifically binding a glycosylated CEA. These variants comprises (but are not limited to): deletion, insertion and/or substitution of several (usually 1-50, preferably 1-30, more preferably 1-20, most preferably 1-10, further more preferably 1-8 or 1-5) amino acids, and addition or deletion of one or more (usually within 20, preferably within 10, more preferably 5 or less) amino acids at C-terminal and/or N-terminal. For example, in the art, the substitution with an amino acid of close or similar property usually does not change the function of protein. As another example, the addition or deletion of one or more amino acids at the C-terminal and/or N-terminal generally does not change the function of protein as well.

The invention also provides analogs of the single-chain antibody. The difference between these analogs and the natural single-chain antibody may be a difference in amino acid sequence, a difference in modification form which does not affect the sequence, or a combination thereof These polypeptides comprises natural or induced genetic variants. Induced variants can be obtained by a variety of techniques, such as random mutagenesis by irradiation or exposure to a mutagen, or site-directed mutagenesis or other known techniques of molecular biology. The analogs also comprise analogs having residues other than the native L-amino acids (e.g., D-amino acids), as well as analogs having non-naturally occurring or synthetic amino acids (e.g., β-, γ-amino acids). It should be understood that the polypeptides of the present invention are not limited to the representative polypeptides exemplified above.

Furthermore, other amino acid sequences which do not substantially affect the activity, expression amount and stability of the single-chain antibody of the present invention may be added to the amino terminus or the carboxy terminus of the single-chain antibody. Preferably, these added amino acid sequences facilitate expression (e.g., signal peptides), facilitate purification (e.g., 6×His sequences), or other sequences that promote the activity, expression, or stability of the single-chain antibody.

The present invention also comprises DNA molecules encoding the single-chain antibodies of the present invention or variants, derivatives thereof. The DNA molecules can be all artificially synthesized or obtained by PCR amplification.

In order to further increase the expression level of the host cell, the coding sequence of the single-chain antibody of the present invention can be engineered, for example, using a host cell-preferred codon to eliminate sequences which are not conducive to gene transcription and translation.

Expression of Single-Chain Antibody

After obtaining the DNA sequence encoding the novel single-chain antibody of the present invention or a variant or derivative thereof, it is cloned into a suitable expression vector and transferred into a suitable host cell. Finally, the transformed host cell is cultured, and the novel single-chain antibody of the present invention is obtained by isolation and purification.

The term "vector" as used herein comprises plasmids, cosmids, expression vectors, cloning vectors, viral vectors, and the like.

In the present invention, various vectors known in the art can be used. For example, a commercially available vector is selected, and then a nucleotide sequence encoding a novel single-chain antibody of the present invention is operably linked to an expression regulatory sequence to form an expression vector.

In the present invention, the term "host cell" comprises prokaryotic cells and eukaryotic cells. Examples of commonly used prokaryotic host cells include *Escherichia coli,*

*Bacillus subtilis* and the like. Host cells for expressing single-chain antibodies include *Escherichia coli*, yeast cells, insect cells, COS cells, CHO cells, and the like. Preferably, the host cell is a prokaryotic cell, more preferably an *E. coli* cell.

After obtaining the transformed host cell, the cell can be cultured under conditions suitable for expression of the single-chain antibody of the present invention to express a single-chain antibody; and then the expressed single-chain antibody can be isolated.

Linker Peptide

As used herein, the term "linker peptide" (linker) refers to a short peptide between a heavy chain variable region of antibody (or a variant thereof) and a light chain variable region of antibody (or a variant thereof), which acts as a linker and allows the heavy and light chain variable regions to fold freely, leaving the antigen binding site in an appropriate configuration without causing a change in molecular dynamics. In general, the linker peptide does not affect or not significantly affect the formation of correct folding and spatial conformation of the amino acid sequences of the heavy chain variable region (VH) and the light chain variable region (VL); alternatively, the linker peptide constitutes a flexible connection between the heavy chain variable region (VH) and the light chain variable region (VL), which facilitates their normal folding. The length of the linker peptide is not particularly limited as long as it allows the heavy and light chain variable regions to be freely folded, and the antigen binding site to be in an appropriate configuration without causing a change in molecular dynamics. For example, the length of the linker peptide can also be 4-30 aa. Preferably, the sequence of the linker peptide of the present invention is set forth in SEQ ID NO: 1.

Chimeric Antigen Receptor (CAR)

The single-chain antibody of the present invention can be used for detection and treatment of a tumor such as gastric cancer, colorectal cancer, and esophageal cancer. The single-chain antibody of the present invention can be specifically expressed on the surface of T cells to construct a chimeric antigen receptor T cell against glycosylated CEA, and specifically kill glycosylated CEA expression-positive cells and tissues. For each of the single-chain antibodies of the present invention, CAR-Ts of three structures are constructed separately and the functional differences of the three structures under each antibody are compared, and a suitable CAR-T structure is adopted for an appropriate target cell. The CAR-Ts of three structures separately are:

scFv-CD8α-CD137-CD3zeta, scFv-CD28-CD28-CD137-CD3zeta, scFv-CD28-CD28-CD3zeta.

In the chimeric antigen receptor structure of the invention:

The hinge region can be an extracellular region selected from the group consisting of CD8α, CD28, human IgG1 Fc, human IgG4 Fc, DAP10 and the like.

The transmembrane regions can be an transmembrane region selected from the group consisting of CD8α, CD28, DAP10 and the like.

The costimulatory domain can be an intracellular region selected from the group consisting of CD28, CD134 (OX40), CD137 (4-1BB), ICOS, DAP10 and the like.

The essential signal domain can be selected from: CD3zeta.

EXAMPLES

The invention is further described below in conjunction with the specific examples and the accompanying drawings, which are not intended to limit the invention. The experimental methods in the following examples which conditions are not specifically described are performed according to the conventional conditions such as those described by J. Sambrook et al., Molecular Cloning Experiment Guide, Science Press, 2002, or according to the manufacturer's recommended conditions. Percentages and parts are by weight unless otherwise stated.

Example 1: Construction of Single-Chain Antibody

TABLE 1

| Single-chain antibody | Seq ID | VH Seq ID | VL Seq ID |
|---|---|---|---|
| $FM2_{(VH\to VL)}$ | SEQ ID NO: 59 | SEQ ID NO: 31 | SEQ ID NO: 32 |
| $FM2_{(VL\to VH)}$ | SEQ ID NO: 64 | SEQ ID NO: 31 | SEQ ID NO: 32 |
| $FM3_{(VH\to VL)}$ | SEQ ID NO: 60 | SEQ ID NO: 33 | SEQ ID NO: 34 |
| $FM3_{(VL\to VH)}$ | SEQ ID NO: 65 | SEQ ID NO: 33 | SEQ ID NO: 34 |
| $FM4_{(VH\to VL)}$ | SEQ ID NO: 61 | SEQ ID NO: 35 | SEQ ID NO: 36 |
| $FM4_{(VL\to VH)}$ | SEQ ID NO: 66 | SEQ ID NO: 35 | SEQ ID NO: 36 |
| $FM5_{(VH\to VL)}$ | SEQ ID NO: 62 | SEQ ID NO: 37 | SEQ ID NO: 38 |
| $FM5_{(VL\to VH)}$ | SEQ ID NO: 67 | SEQ ID NO: 37 | SEQ ID NO: 38 |
| $FM6_{(VH\to VL)}$ | SEQ ID NO: 63 | SEQ ID NO: 39 | SEQ ID NO: 40 |
| $FM6_{(VL\to VH)}$ | SEQ ID NO: 68 | SEQ ID NO: 39 | SEQ ID NO: 40 |

Expression Method of Single-Chain Antibody

Each of the synthesized nucleotide sequences FM2, 3, 4, 5, and 6 was added with 8His (CACCATCACCATCACCATCACCAT (SEQ ID NO: 181)) at 3'-terminal, the amplified fragment was added with sfiI and NotI restriction sites at both ends thereof, and then inserted into a pCANTABSE vector (GE HealthCare). The constructed pCANTABSE (GE) vector was transformed into *E. coli*-HB2151 strain and induced by IPTG to express overnight. The cells were resuspended in PBS buffer, sonicated on ice for 10 min. After centrifugation, the supernatant was purified by His Trap Column (GE), washed with PBS buffer containing 20 mM imidazole for 5-10 column volumes, and then eluted with PBS containing 500 mM imidazole; the subsequent imidazole was desalted with Desalting G25 column (GE) to obtain a single-chain antibody dissolved in PBS.

Example 2: Construction of CAR Recombinant Lentiviral Vector

The virus constructed in the present invention is shown in Table 2:

TABLE 2

| Virus Number | Name | Structure | Seq ID |
|---|---|---|---|
| 1 | $FM2_{(VH\to VL)}$-BBz-EGFP | $FM2_{(VH\to VL)}$-CD8α-CD137-CD3zeta-2A-EGFP | SEQ ID NO: 69 |
| 2 | $FM2_{(VL\to VH)}$-BBz-EGFP | $FM2_{(VL\to VH)}$-CD8α-CD137-CD3zeta-2A-EGFP | SEQ ID NO: 70 |
| 3 | $FM3_{(VH\to VL)}$-BBz-EGFP | $FM3_{(VH\to VL)}$-CD8α-CD137-CD3zeta-2A-EGFP | SEQ ID NO: 71 |
| 4 | $FM3_{(VL\to VH)}$-BBz-EGFP | $FM3_{(VL\to VH)}$-CD8α-CD137-CD3zeta-2A-EGFP | SEQ ID NO: 72 |
| 5 | $FM4_{(VH\to VL)}$-BBz-EGFP | $FM4_{(VH\to VL)}$-CD8α-CD137-CD3zeta-2A-EGFP | SEQ ID NO: 73 |

TABLE 2-continued

| Virus Number | Name | Structure | Seq ID |
|---|---|---|---|
| 6 | FM4$_{(VL\rightarrow VH)}$-BBz-EGFP | FM4$_{(VL\rightarrow VH)}$-CD8α-CD137-CD3zeta-2A-EGFP | SEQ ID NO: 74 |
| 7 | FM5$_{(VH\rightarrow VL)}$-BBz-EGFP | FM5$_{(VH\rightarrow VL)}$-CD8α-CD137-CD3zeta-2A-EGFP | SEQ ID NO: 75 |
| 8 | FM5$_{(VL\rightarrow VH)}$-BBz-EGFP | FM5$_{(VL\rightarrow VH)}$-CD8α-CD137-CD3zeta-2A-EGFP | SEQ ID NO: 76 |
| 9 | FM6$_{(VH\rightarrow VL)}$-BBz-EGFP | FM6$_{(VH\rightarrow VL)}$-CD8α-CD137-CD3zeta-2A-EGFP | SEQ ID NO: 77 |
| 10 | FM6$_{(VL\rightarrow VH)}$-BBz-EGFP | FM6$_{(VL\rightarrow VH)}$-CD8α-CD137-CD3zeta-2A-EGFP | SEQ ID NO: 78 |
| 11 | FM2$_{(VH\rightarrow VL)}$-BBz | FM2$_{(VH\rightarrow VL)}$-CD8α-CD137-CD3zeta | SEQ ID NO: 79 |
| 12 | FM2$_{(VL\rightarrow VH)}$-BBz | FM2$_{(VL\rightarrow VH)}$-CD8α-CD137-CD3zeta | SEQ ID NO: 80 |
| 13 | FM3$_{(VH\rightarrow VL)}$-BBz | FM3$_{(VH\rightarrow VL)}$-CD8α-CD137-CD3zeta | SEQ ID NO: 81 |
| 14 | FM3$_{(VL\rightarrow VH)}$-BBz | FM3$_{(VL\rightarrow VH)}$-CD8α-CD137-CD3zeta | SEQ ID NO: 82 |
| 15 | FM4$_{(VH\rightarrow VL)}$-BBz | FM4$_{(VH\rightarrow VL)}$-CD8α-CD137-CD3zeta | SEQ ID NO: 83 |
| 16 | FM4$_{(VL\rightarrow VH)}$-BBz | FM4$_{(VL\rightarrow VH)}$-CD8α-CD137-CD3zeta | SEQ ID NO: 84 |
| 17 | FM5$_{(VH\rightarrow VL)}$-BBz | FM5$_{(VH\rightarrow VL)}$-CD8α-CD137-CD3zeta | SEQ ID NO: 85 |
| 18 | FM5$_{(VL\rightarrow VH)}$-BBz | FM5$_{(VL\rightarrow VH)}$-CD8α-CD137-CD3zeta | SEQ ID NO: 86 |
| 19 | FM6$_{(VH\rightarrow VL)}$-BBz | FM6$_{(VH\rightarrow VL)}$-CD8α-CD137-CD3zeta | SEQ ID NO: 87 |
| 20 | FM6$_{(VL\rightarrow VH)}$-BBz | FM6$_{(VL\rightarrow VH)}$-CD8α-CD137-CD3zeta | SEQ ID NO: 88 |
| 21 | FM2$_{(VH\rightarrow VL)}$--28BBz-EGFP | FM2$_{(VH\rightarrow VL)}$-CD28-CD28-CD137-CD3zeta-2A-EGFP | SEQ ID NO: 89 |
| 22 | FM2$_{(VL\rightarrow VH)}$--28BBz-EGFP | FM2$_{(VL\rightarrow VH)}$-CD28-CD28-CD137-CD3zeta-2A-EGFP | SEQ ID NO: 90 |
| 23 | FM3$_{(VH\rightarrow VL)}$--28BBz-EGFP | FM3$_{(VH\rightarrow VL)}$-CD28-CD28-CD137-CD3zeta-2A-EGFP | SEQ ID NO: 91 |
| 24 | FM3$_{(VL\rightarrow VH)}$--28BBz-EGFP | FM3$_{(VL\rightarrow VH)}$-CD28-CD28-CD137-CD3zeta-2A-EGFP | SEQ ID NO: 92 |
| 25 | FM4$_{(VH\rightarrow VL)}$--28BBz-EGFP | FM4$_{(VH\rightarrow VL)}$-CD28-CD28-CD137-CD3zeta-2A-EGFP | SEQ ID NO: 93 |
| 26 | FM4$_{(VL\rightarrow VH)}$--28BBz-EGFP | FM4$_{(VL\rightarrow VH)}$-CD28-CD28-CD137-CD3zeta-2A-EGFP | SEQ ID NO: 94 |
| 27 | FM5$_{(VH\rightarrow VL)}$--28BBz-EGFP | FM5$_{(VH\rightarrow VL)}$-CD28-CD28-CD137-CD3zeta-2A-EGFP | SEQ ID NO: 95 |
| 28 | FM5$_{(VL\rightarrow VH)}$--28BBz-EGFP | FM5$_{(VL\rightarrow VH)}$-CD28-CD28-CD137-CD3zeta-2A-EGFP | SEQ ID NO: 96 |
| 29 | FM6$_{(VH\rightarrow VL)}$--28BBz-EGFP | FM6$_{(VH\rightarrow VL)}$-CD28-CD28-CD137-CD3zeta-2A-EGFP | SEQ ID NO: 97 |
| 30 | FM6$_{(VL\rightarrow VH)}$--28BBz-EGFP | FM6$_{(VL\rightarrow VH)}$-CD28-CD28-CD137-CD3zeta-2A-EGFP | SEQ ID NO: 98 |
| 31 | FM2$_{(VH\rightarrow VL)}$--28BBz | FM2$_{(VH\rightarrow VL)}$-CD28-CD28-CD137-CD3zeta | SEQ ID NO: 99 |
| 32 | FM2$_{(VL\rightarrow VH)}$--28BBz | FM2$_{(VL\rightarrow VH)}$-CD28-CD28-CD137-CD3zeta | SEQ ID NO: 100 |
| 33 | FM3$_{(VH\rightarrow VL)}$--28BBz | FM3$_{(VH\rightarrow VL)}$-CD28-CD28-CD137-CD3zeta | SEQ ID NO: 101 |
| 34 | FM3$_{(VL\rightarrow VH)}$--28BBz | FM3$_{(VL\rightarrow VH)}$-CD28-CD28-CD137-CD3zeta | SEQ ID NO: 102 |
| 35 | FM4$_{(VH\rightarrow VL)}$--28BBz | FM4$_{(VH\rightarrow VL)}$-CD28-CD28-CD137-CD3zeta | SEQ ID NO: 103 |
| 36 | FM4$_{(VL\rightarrow VH)}$--28BBz | FM4$_{(VL\rightarrow VH)}$-CD28-CD28-CD137-CD3zeta | SEQ ID NO: 104 |
| 37 | FM5$_{(VH\rightarrow VL)}$--28BBz | FM5$_{(VH\rightarrow VL)}$-CD28-CD28-CD137-CD3zeta | SEQ ID NO: 105 |
| 38 | FM5$_{(VL\rightarrow VH)}$--28BBz | FM5$_{(VL\rightarrow VH)}$-CD28-CD28-CD137-CD3zeta | SEQ ID NO: 106 |
| 39 | FM6$_{(VH\rightarrow VL)}$--28BBz | FM6$_{(VH\rightarrow VL)}$-CD28-CD28-CD137-CD3zeta | SEQ ID NO: 107 |
| 40 | FM6$_{(VL\rightarrow VH)}$--28BBz | FM6$_{(VL\rightarrow VH)}$-CD28-CD28-CD137-CD3zeta | SEQ ID NO: 108 |
| 41 | FM2$_{(VH\rightarrow VL)}$-28z-EGFP | FM2$_{(VH\rightarrow VL)}$-CD28-CD28-CD3zeta-2A-EGFP | SEQ ID NO: 109 |
| 42 | FM2$_{(VL\rightarrow VH)}$-28z-EGFP | FM2$_{(VL\rightarrow VH)}$-CD28-CD28-CD3zeta-2A-EGFP | SEQ ID NO: 110 |
| 43 | FM3$_{(VH\rightarrow VL)}$-28z-EGFP | FM3$_{(VH\rightarrow VL)}$-CD28-CD28-CD3zeta-2A-EGFP | SEQ ID NO: 111 |
| 44 | FM3$_{(VL\rightarrow VH)}$-28z-EGFP | FM3$_{(VL\rightarrow VH)}$-CD28-CD28-CD3zeta-2A-EGFP | SEQ ID NO: 112 |
| 45 | FM4$_{(VH\rightarrow VL)}$-28z-EGFP | FM4$_{(VH\rightarrow VL)}$-CD28-CD28-CD3zeta-2A-EGFP | SEQ ID NO: 113 |
| 46 | FM4$_{(VL\rightarrow VH)}$-28z-EGFP | FM4$_{(VL\rightarrow VH)}$-CD28-CD28-CD3zeta-2A-EGFP | SEQ ID NO: 114 |
| 47 | FM5$_{(VH\rightarrow VL)}$-28z-EGFP | FM5$_{(VH\rightarrow VL)}$-CD28-CD28-CD3zeta-2A-EGFP | SEQ ID NO: 115 |
| 48 | FM5$_{(VL\rightarrow VH)}$-28z-EGFP | FM5$_{(VL\rightarrow VH)}$-CD28-CD28-CD3zeta-2A-EGFP | SEQ ID NO: 116 |
| 49 | FM6$_{(VH\rightarrow VL)}$-28z-EGFP | FM6$_{(VH\rightarrow VL)}$-CD28-CD28-CD3zeta-2A-EGFP | SEQ ID NO: 117 |
| 50 | FM6$_{(VL\rightarrow VH)}$-28z-EGFP | FM6$_{(VL\rightarrow VH)}$-CD28-CD28-CD3zeta-2A-EGFP | SEQ ID NO: 118 |
| 51 | FM2$_{(VH\rightarrow VL)}$-28z | FM2$_{(VH\rightarrow VL)}$-CD28-CD28-CD3zeta | SEQ ID NO: 119 |
| 52 | FM2$_{(VL\rightarrow VH)}$-28z | FM2$_{(VL\rightarrow VH)}$-CD28-CD28-CD3zeta | SEQ ID NO: 120 |
| 53 | FM3$_{(VH\rightarrow VL)}$--28z | FM3$_{(VH\rightarrow VL)}$-CD28-CD28-CD3zeta | SEQ ID NO: 121 |
| 54 | FM3$_{(VL\rightarrow VH)}$-28z | FM3$_{(VL\rightarrow VH)}$-CD28-CD28-CD3zeta | SEQ ID NO: 122 |
| 55 | FM4$_{(VH\rightarrow VL)}$-28z | FM4$_{(VH\rightarrow VL)}$-CD28-CD28-CD3zeta | SEQ ID NO: 123 |
| 56 | FM4$_{(VL\rightarrow VH)}$-28z | FM4$_{(VL\rightarrow VH)}$-CD28-CD28-CD3zeta | SEQ ID NO: 124 |
| 57 | FM5$_{(VH\rightarrow VL)}$-28z | FM5$_{(VH\rightarrow VL)}$-CD28-CD28-CD3zeta | SEQ ID NO: 125 |
| 58 | FM5$_{(VL\rightarrow VH)}$-28z | FM5$_{(VL\rightarrow VH)}$-CD28-CD28-CD3zeta | SEQ ID NO: 126 |
| 59 | FM6$_{(VH\rightarrow VL)}$-28z | FM6$_{(VH\rightarrow VL)}$-CD28-CD28-CD3zeta | SEQ ID NO: 127 |
| 60 | FM6$_{(VL\rightarrow VH)}$-28z | FM6$_{(VL\rightarrow VH)}$-CD28-CD28-CD3zeta | SEQ ID NO: 128 |

1. Construction of Lentiviral Plasmid Vector

1) Whole Gene Synthesis of Gene Sequences

To construct the lentivirus of Table 2, the essential gene sequences were subjected to whole gene synthesis according to the structure shown in Table 2.

2) Amplification of Nucleic Acid Fragments

The synthesized gene products numbered as SEQ ID NO. 69-78, 89-98, 109-118 were amplified with the upstream primers (SEQ ID NO. 159-168) and the downstream primer (SEQ ID NO. 169). The PCR amplification conditions were: pre-denaturation: 95° C. for 5 minutes; denaturation: 95° C. for 30 seconds; annealing: 55° C. for 30 seconds; extension 72° C. for 1 minute, 35 cycles; final extension: 72° C. for 10 minutes.

The synthesized gene products numbered as SEQ ID NO. 79-88, 99-108, 119-128 were amplified with the upstream primers (SEQ ID NO. 159-168) and the downstream primer (SEQ ID NO. 170). The PCR amplification conditions were the same as above.

3) Construction of Viral Plasmid Vector a) The amplified fragments of SEQ ID NO. 79-88, 99-108, 119-128 were subjected to restriction endonuclease digestion. The restriction enzymes used were BamHI and EcoRI, and the digestion system was as follows: 0.5 μl of BamHI, 0.5 μl of EcoRI, 2 μl of Buffer, 2 μl of BSA, 2 μg of amplified fragment, supplemented with sterile water to 20 μl. After being incubated for 2 hours at 37° C., the enzyme digestion system was subjected to DNA cleaning and recovery. The recovery method was as follows: after adding 80 μl of Buffer PCR-A to the digestion system, the mixture was transferred to a preparation tube, and the preparation tube was placed in a 2 ml centrifuge tube, centrifuged at 12,000×g for 1 min, and the filtrate was discarded. The preparation tube was placed back in a 2 ml centrifuge tube, added with 700 μl of Buffer W2, centrifuged at 12,000×g for 1 min, and the filtrate was discarded. The preparation tube was placed in a clean 1.5 ml centrifuge tube, and 25-30 μl of Eluent or deionized water was added to the membrane center of the preparation tube, stood for 1 min at room temperature. The DNA was eluted by centrifugation at 12,000×g for 1 min.

The amplified fragments of SEQ ID NO. 69-78, 89-98, 109-118 were subjected to restriction endonuclease digestion. The restriction endonuclease used was BamHI. The digestion system was as follows: 0.5 μl of BamHI, 0.5 μl of EcoRI, 2 μl of Buffer, 2 μl of BSA, 2 μg of amplified fragment, supplemented with sterile water to 20 μl. After being incubated for 2 hours at 37° C., the enzyme digestion system was subjected to DNA cleaning and recovery. The recycling method was the same as above.

b) The vector fragments were subjected to restriction endonuclease digestion, and the enzyme digestion system and method were the same as shown above. After the digestion, the system was subjected to DNA agarose gel electrophoresis, and the vector fragments (about 8 Kb) were recovered by gel. The recovery system was as follows: the DNA fragment of interest was separated from other DNA bands by agarose electrophoresis, and then the agarose gel block containing the DNA to be recovered was cut by a clean scalpel and placed in a pre-numbered 1.5 ml EP tube. The agarose gel block should be cut as thin as possible, and the time of ultraviolet light irradiation should be as short as possible. 500 μl of the gel solution was added to each tube, and was incubated with a warm bath at 65° C. for 5 to 10 minutes, during which time the mixture was inverted every 2 minutes to completely melt the gel. The dissolved gel was taken out of the water bath and allowed to stand at room temperature for 2 min until it was cooled to room temperature. A UNIQ-10 recovery column was added with 500 μl of an equilibration solution, centrifuged at 12,000 rpm for 1 min, and the collection solution was discarded, set aside. The liquid was transferred to a UNIQ-10 column and stood for 1 minute at room temperature, centrifuged at 8,000 rpm for 1 minute. The UNIQ-10 column was got down and the waste liquid in the collection tube was discarded (if the target strip was very light, the liquid in the collection tube can pass the UNIQ-10 column again), the UNIQ-10 column was placed in the same collection tube, added with 700 μl of Wash buffer, centrifuged at 10,000 rpm for 30 seconds, and repeated once. The UNIQ-10 column was got down, the waste liquid in the collection tube was discarded, the UNIQ-10 column was placed in the same collection tube, and centrifuged at 12,000 rpm for 2 min. The UNIQ-10 column was placed in a new 1.5 ml EP tube, the lid of the UNIQ-10 column was opened, and placed in an oven at 65° C. for 10 min to allow the ethanol to evaporate sufficiently. 40 μl of Elution Buffer was added to the column membrane center (note: the tip should be replaced to avoid contamination), the lid of the UNIQ-10 column was closed, and placed in an oven at 65° C. for 2 minutes. The DNA of interest was recovered by centrifugation at 12,000 rpm for 1 minute.

The EGFP expression vector was subjected to restriction endonuclease digestion, the restriction enzyme used was BamHI, and the enzyme digestion system and the gel recovery method were the same as described above.

c) Ligation of Plasmid Vector and Fragment of Interest

The digestion products of SEQ ID NO. 79-88, 99-108, 119-128 were ligated to the EGFP expression-free vector (CV185, Genechem); and the amplified digestion products of SEQ ID NO. 69-78, 89-98, 109-118 were ligated to the EGFP expression vector (CV178, Genechem).

The ligation system was as follows: 25 ng of insertion fragment, 100 ng of vector fragment, 2 μl of T4 ligase buffer, 1 μl of T4 ligase, supplemented with sterile water to 20 μl, and ligated at 22° C. for 1 hour.

2. Lentiviral Packaging

The third generation of lentiviral packaging system was used: Transfer plasmid: CV178 or CV185 (Genechem), Envelop plasmid: H1 (Genechem), Packaging plasmid: H2 (Genechem) (Zufferey et al., J Virol 72 (12): 9873-80, 1998).

HEK-293T cells were supplied according to the 24 h passage period, and the medium was exchanged before transfection. Each plate of cells was replaced with 5 ml of DMEM medium containing 2% FBS using an electric pipette. HBW, H1 (12 μg/plate, the plate referred to a 10 cm cell culture dish, similarly hereinafter), recombinant H2 (10 μg/plate), Vector (24 μg/plate), $CaCl_2$ (50 μl/plate) were added in sequence, and finally oscillated on a vortex oscillator with an addition of 2×HBS (500 μl/disc) dropwise, and the transfection system was 1 ml/plate. Among them, the Vector was the vector constructed in the Step 1. The transfection system was carefully pipetted, 1000 μl of the mixture was taken and added dropwise to 293T cells after mixing, and the operation was kept stable and the transfection system was evenly distributed on the 10 cm plate. The plate was kept level and the liquid in the plate was shaken ten times in each of the front, rear, left and right directions, and the mixing process should be sufficient, but no liquid could be spilled or flowed to the outside of the plate, and then placed in a 37° C., 5% $CO_2$ incubator. Eight hours after transfection, the supernatant was discarded and the DMEM medium was replaced with an electric pipette. Between 28 and 30 hours after the end of transfection, the supernatant was collected for the first time, and 10 ml of DMEM medium was added for supplement. Between 48 to 50 hours after the end of transfection, the supernatant was collected for the second time. After ultracentrifugation, it was resuspended in 100 μl of DMEM for later use.

Example 3: Infection of T Lymphocytes with Recombinant Lentivirus

Infection experiments were performed according to conventional methods known to those skilled in the art. The infection steps were briefly described as follows:

1. Peripheral blood mononuclear lymphocytes (PBMC) were obtained, and $>1\times10^7$ cells were obtained by the blood apheresis system.

2. Experimental anti-human CD3/CD28 antibody treatment of cell culture dishes.

Anti-human CD3 antibody (OKT3 clone, MACS) and anti-human CD28 antibody (15E8 clone, MACS) were diluted with PBS to a final concentration of 1 μg/ml, and the diluted antibody mixtures were added to a cell culture dish to spread the culture in the dish. After incubation for 2 hours at room temperature, the dish was washed once with PBS, set aside.

3. Activation of T lymphocytes

The isolated PBMCs were resuspended in T lymphocyte culture medium (TexMACS medium+10% FBS+30 IU/recombinant human IL-2) to a final concentration of $1*10^6$ cells/ml, placed and cultured in the dish treated in the Step 2. The culture condition was 37° C.+5% $CO_2$ and the culture time was 24 hours.

4. Infection of the activated T lymphocytes

1) Preparation of Infection Reagents

A certain amount of T cell culture medium was taken, added with synperonic F108 to reach a final concentration of 1 mg/ml, mixed well, and heated to 37° C. in a water bath, set aside.

2) Treatment of Culture Plate 1 mg/ml CD3 and 0.5 mg/ml CD28 antibodies were taken and diluted at a 1:1000 volume ratio to an appropriate amount of PBS buffer, and retronectin reagent (takara, Cat. No. T100A) was taken and diluted to the PBS buffer at a volume ratio of 1:40. After well mixing, the buffer was spread evenly to cell dishes and incubated for 2 hours at room temperature. After 2 hours, the dishes were washed with PBS and set aside.

3) Infection of T Lymphocytes with Lentivirus and Maintaining T Lymphocytes

The infection reagents prepared in 1) was used to dilute the activated T lymphocytes, lentivirus was added according to MOI=3, and mixed. The mixture was spread evenly in the dish as treated in 2).

The cell density was monitored after infection to maintain the cells at $1*10^6$ cells/ml; typically, after 14 days, the cells were amplified for 30-100 folds.

Example 4: Detection of Glycosylated CEA Expression in Cancer Cell Lines of Digestive Tract Source Flow cytometry was used to detect the expression level of glycosylated CEA in various target cells. The specific detection method was as follows:

1. $6*10^5$ cells/group as shown in Table 3, were taken, centrifuged at 200 g for 5 minutes, and the supernatant was discarded;

2. After being resuspended in 200 μl PBS, the resuspended cells were divided into two groups, one of which was added with 1 μg of the single-chain antibody against glycosylated CEA of the present invention, and incubated at 4° C. for 2 hours;

3. 1 ml of PBS was added to each group, mixed and centrifuged at 200 g for 5 min, the supernatant was discarded; After the cells were resuspended with 100 μl of PBS, 5 μl of goat anti-mouse IgG1 FITC-labeled secondary antibody was added to the cell suspension, and incubated at 4° C. for 1 hour;

4. The cells were washed three times with PBS, measured and analyzed with flow cytometry.

The results are shown in Table 3. The expression of glycosylated CEA antigen was not detected in SW620, while the glycosylated CEA expression in different degrees was detected in KATO3, CRYPT as well as SW620-CEA and LOVO cell lines overexpressing CEA.

Construction method of SW620-CEA cell line: SW620 cells were maintained and cultured in 1640 medium which was added with 10% FBS; CEA gene (CEACAM5, NM-004363) in full length was obtained by whole gene synthesis; after being cloned into GV348 vector (Genechem), the gene with two helper plasmids transfected 293T cells by calcium phosphate and were packaged to form lentiviruses. SW620 cells were inoculated to a 24-well plate, $10^5$/well, and cultured overnight; the SW620 was infected with CEA-expressing lentivirus according to MOI=3, and puromycin was added to reach a final concentration of 1 μg/ml 24 hours after infection; the cells were screened by puromycin to obtain monoclone. The CEA expression was detected by FACS. The results are shown in FIG. 1.

TABLE 3

| Name of cell | Source | Property |
|---|---|---|
| SW620 | ATCC CCL-227 | Not expressing CEA |
| SW620-CEA | Constructed and preserved in the inventors' laboratory | Expressing CEA |
| LOVO | ATCC CCL-229 | Expressing CEA |
| KATO3 | ATCC HTB103 | Expressing glycosylated CEA antigen |
| CRYPT | Fan Daiming Laboratory, Fourth Military Medical University | Expressing glycosylated CEA antigen |

Example 4a: Detection of CEA Expression in Tumor Samples Using FM4 Single-Chain Antibody and CEA Antibody The patient's gastric cancer tumor tissue samples were embedded in liquid paraffin and frozen, the sections were fixed on glass slides; after dewaxing with xylene, antigen recovery was performed using citric acid buffer; the repaired samples were blocked with 5% FBS in PBS buffer for half an hour, 2 μg/ml of the FM4 single-chain antibody of the present invention or CEA antibody (clone CB30) (ebioscience, Cat. No. 14-0669-82) was added to the refrigerator at 4° C. overnight; the tissue slides were washed 3 times with PBS, added with second antibody and subjected to color development.

The FM4 single-chain antibody showed higher sensitivity and tissue specificity (as shown in Table 4).

TABLE 4

| Antibody | Gastric cancer | Para-carcinoma |
|---|---|---|
| FM4 | 73% | 24% |
| CEA antibody | 51% | 20% |

Example 5: Study on Specificity of CAR-T on Glycosylated CEA Positive Cells

In order to investigate whether CAR-T specifically recognizes and produces specific functions in glycosylated CEA-positive cells (LoVo, KATO3, CRYPT, and SW620-CEA with low-level expression of antigen), the present laboratory detected the specific cytokine release and target cell-specific killing of the four constructed CAR-Ts, i.e., $FM2_{(VL\rightarrow VH)}$-BBz, $FM4_{(VL\rightarrow VH)}$-BBz, $FM5_{(VL\rightarrow VH)}$-BBz, and $FM6_{(VL\rightarrow VH)}$-BBz (SEQ ID NO. 80, SEQ ID NO. 84, SEQ ID NO. 86, SEQ ID NO. 88), after being co-cultured with target cells, under similar infection efficiency, using T lymphocytes not infected with CAR virus as control.

1. Flow Detection of CAR-T Infection Efficiency

Since EGFP protein and CAR protein were co-expressed in CAR-T cells, the percentage of EGFP-positive cells detected by flow cytometry could represent CAR-positive cells. The T cells not infected with CAR virus were used as control, and the test results were shown in the following table (Table 5):

TABLE 5

| Name | CD3 + T lymphocyte EGFP positive rate |
|---|---|
| Mock T cell | 0% |
| $FM2_{(VL\rightarrow VH)}$-BBz | 27% |

TABLE 5-continued

| Name | CD3 + T lymphocyte EGFP positive rate |
|---|---|
| $FM4_{(VL\rightarrow VH)}$-BBz | 71% |
| $FM5_{(VL\rightarrow VH)}$-BBz | 50% |
| $FM6_{(VL\rightarrow VH)}$-BBz | 93% |

2. Cytokine Secretion Levels after Interaction of CAR-T with Target Cells

The target cells were SW620, SW620-CEA, LoVo, and KATO3 cells. The effector cells were the five cells mentioned in Table 5, and the cytokine secretion was detected 10 days after the CAR virus infection.

The method was as follows: $1*10^5$ target cells were separately mixed with effector cells at a ratio of 1:1 in 100 μl of RPMI 1640+2% FBS medium, and incubated for about 16 hours in a 37° C. 5% $CO_2$ incubator. After 16 hours, centrifugation was carried out for 5 minutes at 200 g, and the supernatant was taken to measure the level of cytokine secretion in the supernatant. The cytokine content was measured by HU TH1-TH2 CBA KIT produced by BD Company. The mechanism of the measurement was that the cytokines in the reaction solution could bind to the antibodies on the corresponding beads, and the beads corresponding to each cytokine had APC fluorescence labels with different intensity; after the cytokines bound to the beads, the cytokines bound to the beads were further labeled with another PE fluorescence labeled antibody, and the content of cytokines was determined by measuring the fluorescence intensity of PE, and different cytokine species were distinguished by the differences in APC fluorescence intensities. In this study, the secretion levels of three cytokines, i.e., IL-2, IFN-γ and TNF-α, were detected. The specific test methods referred to the kit instructions. The test results were analyzed by FCAP Array v3 software, and the results are shown in FIGS. 2, 3, 4, 5, 6, and 7.

The results showed that IL-2, TNF-α, IFN-γ and other cytokines increased significantly after $FM2_{(VL\rightarrow VH)}$-BBz and $FM4_{(VL\rightarrow VH)}$-BBz interacted with the target cells.

3. In Vitro Killing Toxicity to Target Cells after Interaction of CAR-T with Target Cells In order to verify the killing effect of CAR-T on glycosylated CEA-positive target cells, the antigen expression-positive cells LoVo, KATO3 and CRYPT, as well as SW620-CEA with low level of antigen expression were used in this study. The used kits were Cytotox96 non-radioactive cytotoxicity assay kit (Promega). The mechanism of this method was that the traditional radioactive elements were replaced with lactate dehydrogenase (LDH) which was stably expressed in the cells and was not secreted; when apoptosis of the cells occurred, LDH was released extracellularly, the content of formazan oxidized by LDH was detected to determine the level of enzyme in the supernatant, thereby determining the level of apoptosis. The effector cells were $FM4_{(VL\rightarrow VH)}$-28z, and the ratio of effector cells to target cells was 1:2, 1:5, 1:10, 1:20, 1:30, respectively. The number of target cells was 10,000 cells/well, two accessory wells were set in each group, and the detection time was 4 hours after the interaction.

Among them, each of the experimental groups and the control groups were set as follows:

Experimental groups: CAR-T cells with different ratios of effector cells to target cells and different target cells;

Control group 1: group with maximum release of LDH in those of target cells;

Control group 2: group with spontaneous release of LDH in those of target cells;

Control group 3: group with spontaneous release in those of effector cells;

The specific experimental methods referred to the kit instructions. The cytotoxicity was calculated by the formula of:

Specific lysis=(experimental group−control group 2−control group 3)/(control group 1−control group 2).

Figure 8:
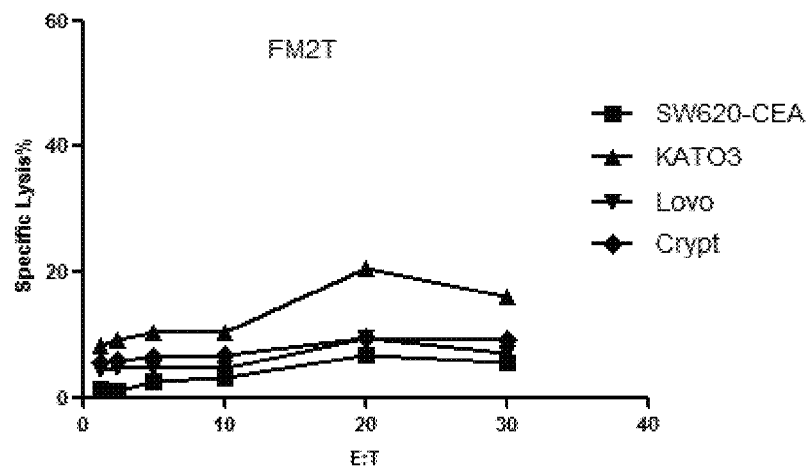
FIG. 8. $FM2_{(VL \to VH)}$-BBz was mixed with target cells for 4 hours in an E:T ratio, and LDH release in the supernatant was measured to determine the killing of target cells by $FM2_{(VL \to VH)}$-BBz.
Figure 9:
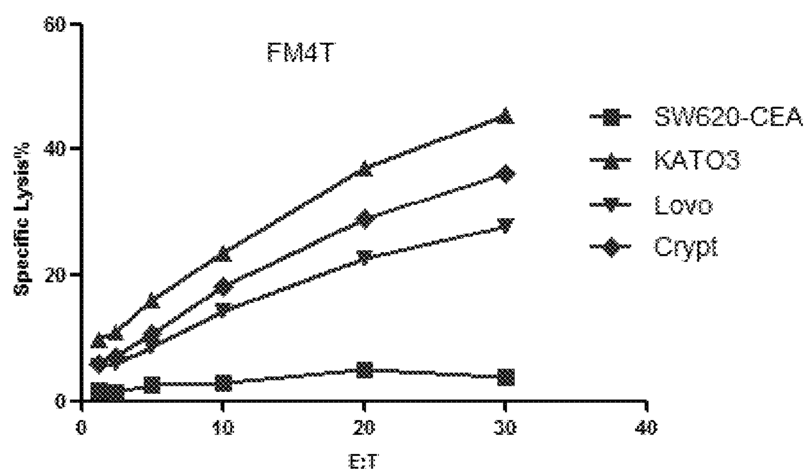
FIG. 9. $FM4_{(VL \to VH)}$-BBz was mixed with target cells for 4 hours in an E:T ratio, and LDH release in the supernatant was measured to determine the killing of target cells by $FM4_{(VL \to VH)}$-BBz.

The results showed that $FM4_{(VL\rightarrow VH)}$-28z had a strong killing effect on LoVo, KATO3 and CRYPT cells, but almost no killing effect on SW620-CEA. The relevant results are shown in FIGS. 8 and 9.

This study demonstrates that $FM4_{(VL\rightarrow VH)}$-28z specifically recognizes glycosylated CEA antigens and is less sensitive to CEA antigens with a lower degree of glycosylation.

Example 6: Effect of CAR-T on Glycosylated CEA-Positive PDX Tumor Model

NCG mice (purchased from the Institute of Model Biology of Nanjing University) were subcutaneously injected with glycosylated CEA antigen-positive patient-derived tumor cells. After the patient's tumor tissue was removed, the connective tissue and blood vessels on the surface were removed; the tumor mass was cut along the midline, and the necrotic tissues, the large calcification points and the secretions were removed, and after careful cleaning, tumor tissues with good quality and toughness were transferred to fresh, ice-cold RPMI-1640 medium. The tumor tissues were cut into small tumor masses of about 3×3 $mm^2$ and transplanted unilaterally into the NSG mice. When the average tumor volume reached 160-180 $mm^3$, the model animals were intratumorally injected with effector cells.

The effector cells used in this study were $FM4_{(VL\rightarrow VH)}$-BBz, and the control group was T cells not transfected with CAR and an equal amount of PBS. Before the injection, the effector cells were washed twice with PBS, and resuspended in PBS to reach 3E7/ml and 1E8/ml, respectively, and recorded as low dose group and high dose group, respectively. Each mouse was intratumorally injected with 30 μl of effector cells/PBS.

The research contents of this study included:

Mouse body weight and tumor volume/3 days/time;

Mouse peripheral blood cytokine detection/7 days/time;

Mouse peripheral blood CAR copy number/7 days/time.

Figure 10:
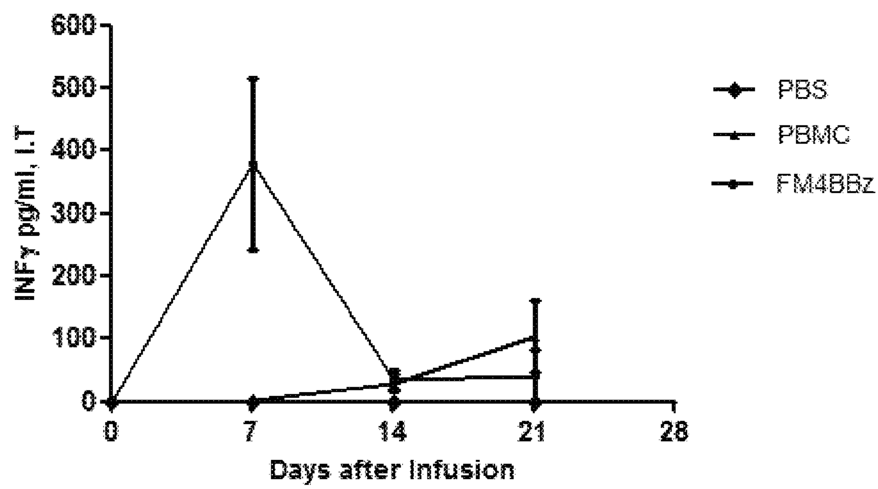
FIG. 10. Detection of IFNγ release in peripheral blood of PDX model mice.

The tumor volume results are shown in FIG. 10. From the fourth day after injection of CAR-T, the tumor volume of the $FM4_{(VL\rightarrow VH)}$-BBz high-dose group began to decline, while the empty T-cell group and the PBS group showed no downward trend. This indicates that CAR-T has a significant inhibitory effect on the glycosylated CEA-positive tumors. After injection of CAR-T, there was no significant difference in body weight of the mice injected with CAR-T in comparison with the empty T cell group and the PBS control group.

Figure 11:
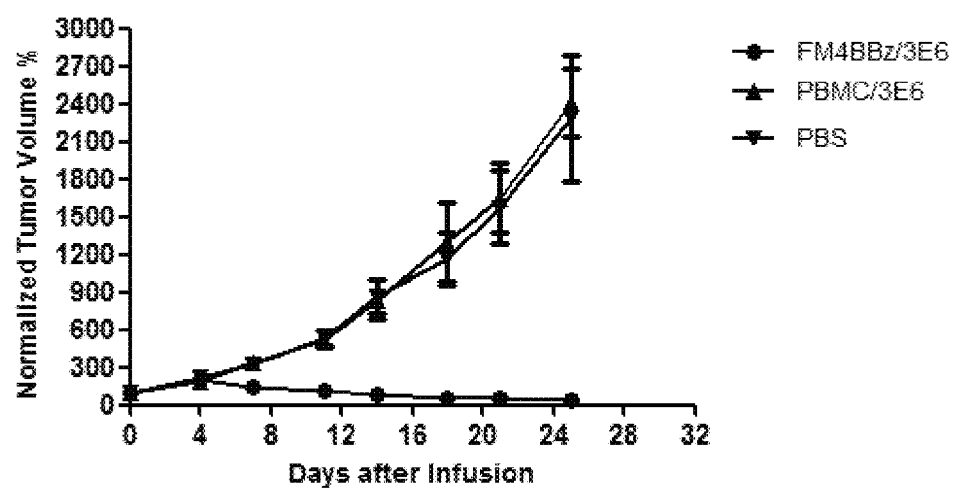
FIG. 11. Tumor growth curve of the PDX model.

The cytokine secretion trend in peripheral blood is shown in FIG. 11. In the CAR-T injection group, the secretion of a variety of human cytokines (IL-2, TNF-α, IFN-γ) was detected in peripheral blood, and the secretion amount of cytokines gradually decreased with the decrease of tumor volume, which proved that CAR-T produced a significant activation response to tumor cells.

Example 6a: Mouse Tumor Model

NSG mice (NOD scid IL2Rγnull) were inoculated subcutaneously with 1E7/mouse of Lovo cells (CCL229, ATCC) to form tumors with volume of 200 $mm^3$–300 $mm^3$. The tumors were injected with PBMC as control and $FM4_{(VL \rightarrow VH)}$-BBz, and the specific groups are as follows:

| Group (5NSG/groups) | Treatment |
|---|---|
| PBMC | 3E6 PBMC/100 µl PBS, intratumoral injection |
| FM4BBz high-dose | 3E6 FM4BBz/100 µl PBS, intratumoral injection |
| FM4BBz low-dose | 1E6 FM4BBz/100 µl PBS, intratumoral injection |

NSG mice that were transfused with PBMC or FM4BBz T cells were bled 40 µl (day 3 and day 7) through tail vein, the samples were resuspended in equal volume of PBS and centrifuged, the supernatant was used for cytokine release assay (BD Cytometric Bead Array). The results are shown in FIG. 14.

Figure 14:
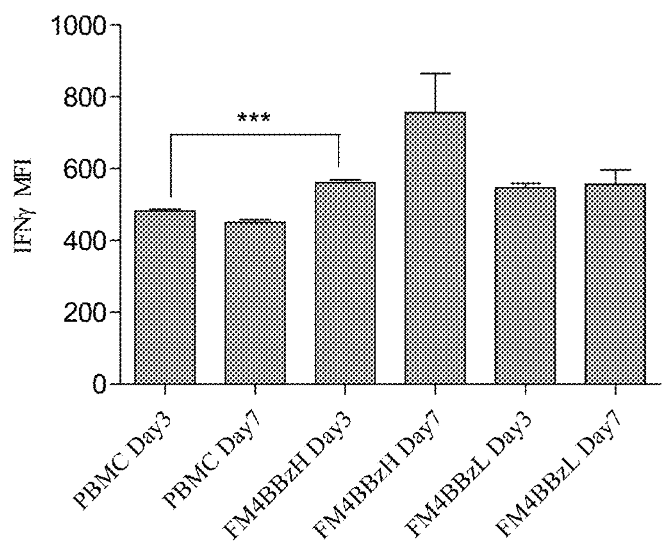
FIG. 14. Detection of INFγ release in mice of tumor model.

As shown in FIG. 14, IFNγ was detected in peripheral blood in both high-dose or low-dose FM4BBz-transfused groups, suggesting that FM4BBz contacted tumor cells and caused the release of cytokines, while in the control group, PBMC did not induce the release of cytokines (FM4BBzH/L vs. PBMC group, p value <0.001). The tumor volume was measured twice a week, for 35 days, and the tumor growth curve is shown in FIG. 15.

Figure 15:
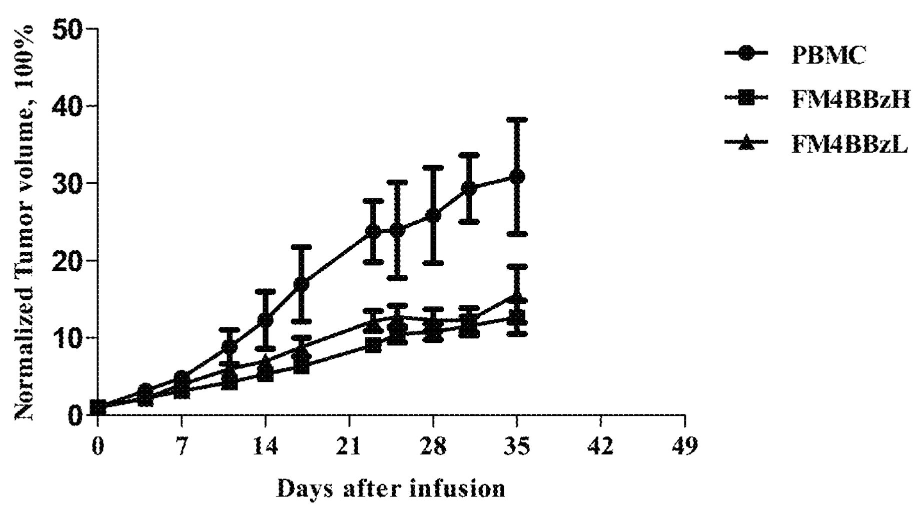
FIG. 15. Tumor killing effect in mice of tumor model.

As shown in FIG. 15, both high- and low-dose FM4BBz groups exhibited significant inhibition on tumor growth, suggesting that FM4BBz had effects of killing tumor.

Figure 12:
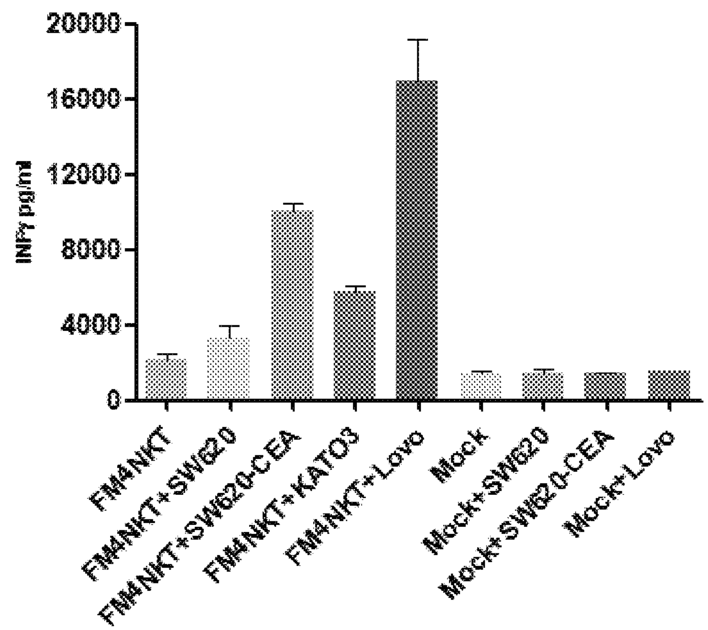
FIG. 12. $FM4_{(VL \to VH)}$-BBz-NK92 cytokine secretion assay.
Figure 13:
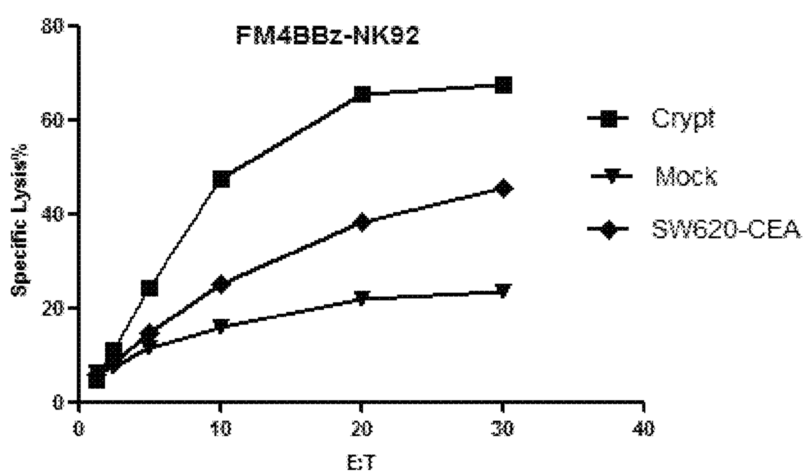
FIG. 13. $FM4_{(VL\rightarrow VH)}$-BBz-NK92 cell killing assay.

Example 7: Infection of NK92 Cells with $FM4_{(VL \rightarrow VH)}$-BBz Lentivirus NK92 cells were cultured in 1640 medium containing 20% FBS, 150 IU/ml hIL-2. According to the method of Example 3, the NK92 cell line was infected with $FM4_{(VL \rightarrow VH)}$-BBz CAR virus, and cultured continuously for 10 days. $FM4_{(VL \rightarrow VH)}$-BBz-NK92 cells were used for killing experiments and cytokine release assays, and the results are shown in FIGS. 12 and 13.

Example 8: Antibody-Cell Binding Assay

The antibodies FM2, FM4, FM5, and FM6 were diluted with PBS buffer containing 1% BSA, and incubated with SW620-CEA or CRYPT cells (final concentrations: 50 µg/ml, 5 µg/ml, 0.5 µg/ml, 0.05 µg/ml, 0.005 µg/ml, 0.0005 µg/ml) for 1 hour at room temperature; the cells were washed twice with PBS buffer containing 1% BSA, and then incubated with Goat Anti Mouse IgG-APC for 1 hour; the cells were washed twice with PBS buffer containing 1% BSA and resuspended in PBS buffer; the APC fluorescence values of the cells were read using BD Accuri C6 FACS.

Using the median fluorescence value (MFI) as the ordinate and the antibody concentration (µg/ml) as the abscissa, the S-curve was fitted using a logistic equation to calculate the antibody binding EC50, the results are shown in the following table:

TABLE 6

| Antibody | EC50-SW620-CEA µg/ml | EC50-CRYPT µg/ml |
|---|---|---|
| FM2 | 0.8 | 0.02 |
| FM4 | >50 | 0.51 |
| FM5 | 0.2 | 0.04 |
| FM6 | 0.3 | 0.02 |

CONCLUSIONS

SW620-CEA is CEA overexpressed in the SW620 cell line (CEACAM5), and its surface CEA is in a non-glycosylated state; CRYPT is a tumor cell line expressing glycosylated CEA.

It can be concluded from the EC50 values of antibody calculated according to the antibody-cell binding assay that the antibody FM4 specifically binds to the glycosylated CEA and has high specificity (selective >100-fold).

What is claimed is:

1. A chimeric antigen receptor (CAR), wherein the CAR comprises:

i) an antigen-binding domain targeting a glycosylated CEA;

ii) a transmembrane domain, and iii) an intracellular signaling domain comprising a costimulatory domain, wherein the antigen-binding domain targeting the glycosylated CEA comprises a heavy chain variable region and a light chain variable region, characterized in that the heavy chain variable region and the light chain variable region are selected from any one of the following combinations:

a. the heavy chain variable region comprises CDR-H1 set forth in SEQ ID NO: 1, CDR-H2 set forth in SEQ ID NO: 2, and CDR-H3 set forth in SEQ ID NO: 3; and the light chain variable region comprises CDR-L1 set forth in SEQ ID NO: 4, CDR-L2 set forth in SEQ ID NO: 5, and CDR-L3 set forth in SEQ ID NO: 6;

b. the heavy chain variable region comprises CDR-H1 set forth in SEQ ID NO:7, CDR-H2 set forth in SEQ ID NO:8, and CDR-H3 set forth in SEQ ID NO:9; and the light chain variable region comprises CDR-L1 set forth in SEQ ID NO: 10, CDR-L2 set forth in SEQ ID NO: 11, and CDR-L3 set forth in SEQ ID NO: 12;

c. the heavy chain variable region comprises CDR-H1 set forth in SEQ ID NO: 13, CDR-H2 set forth in SEQ ID NO: 14, and CDR-H3 set forth in SEQ ID NO: 15; and the light chain variable region comprises CDR-L1 set forth in SEQ ID NO: 16, CDR-L2 set forth in SEQ ID NO: 17, and CDR-L3 set forth in SEQ ID NO: 18;

d. the heavy chain variable region comprises CDR-H1 set forth in SEQ ID NO: 19, CDR-H2 set forth in SEQ ID NO: 20, and CDR-H3 set forth in SEQ ID NO: 21; and the light chain variable region comprises CDR-L1 set forth in SEQ ID NO: 22, CDR-L2 set forth in SEQ ID NO: 23, and CDR-L3 set forth in SEQ ID NO: 24; or e. the heavy chain variable region comprises CDR-H1 set forth in SEQ ID NO: 25, CDR-H2 set forth in SEQ ID NO: 26, and CDR-H3 set forth in SEQ ID NO: 27; and the light chain variable region comprises CDR-L1 set forth in SEQ ID NO: 28, CDR-L2 set forth in SEQ ID NO: 29, and CDR-L3 set forth in SEQ ID NO:30.

2. The chimeric antigen receptor according to claim 1, wherein the heavy chain variable region and the light chain variable region are selected from any one of the following combinations: a) the heavy chain variable region comprises a polypeptide fragment set forth in SEQ ID NO: 31, and the light chain variable region comprises a polypeptide fragment set forth in SEQ ID NO: 32; b) the heavy chain variable region comprises a polypeptide fragment set forth in SEQ ID NO: 33, and the light chain variable region comprises a polypeptide fragment set forth in SEQ ID NO: 34; c) the heavy chain variable region comprises a polypeptide fragment set forth in SEQ ID NO: 35, and the light chain variable region comprises a polypeptide fragment set forth in SEQ ID NO: 36; d) the heavy chain variable region comprises a polypeptide fragment set forth in SEQ ID NO: 37, and the light chain variable region comprises a polypeptide fragment set forth in SEQ ID NO: 38; or e) the heavy chain variable region comprises a polypeptide fragment set forth in SEQ ID NO: 39, and the light chain variable region comprises a polypeptide fragment set forth in SEQ ID NO:40.

3. The chimeric antigen receptor according to claim 1, wherein the antigen-binding domain is a single-chain antibody that specifically recognizes a human glycosylated CEA, the amino acid sequence of the single-chain antibody is set forth in any one of SEQ ID NOs: 171-180.

4. The chimeric antigen receptor according to claim 1, further comprising a hinge region, wherein the transmembrane domain comprises CD8α and/or CD28, and the intracellular signaling domain comprises one or more of CD28, CD137, and CD3zeta.

5. A nucleic acid molecule encoding the chimeric antigen receptor according to claim 1.

6. A cell expressing the chimeric antigen receptor according to claim 1, wherein the cell is selected from the group consisting of a T cell, an NK cell and a B cell.

7. A single-chain antibody that specifically binds to a human glycosylated CEA, the single-chain antibody comprising a heavy chain variable region and a light chain variable region, characterized in that the heavy chain variable region and the light chain variable region are selected from any of the following combinations:

a. the heavy chain variable region comprises CDR-H1 set forth in SEQ ID NO: 1, CDR-H2 set forth in SEQ ID NO: 2, and CDR-H3 set forth in SEQ ID NO: 3; and the light chain variable region comprises CDR-L1 set forth in SEQ ID NO: 4, CDR-L2 set forth in SEQ ID NO: 5, and CDR-L3 set forth in SEQ ID NO: 6;

b. the heavy chain variable region comprises CDR-H1 set forth in SEQ ID NO:7, CDR-H2 set forth in SEQ ID NO:8, and CDR-H3 set forth in SEQ ID NO:9; and the light chain variable region comprises CDR-L1 set forth in SEQ ID NO: 10, CDR-L2 set forth in SEQ ID NO: 11, and CDR-L3 set forth in SEQ ID NO: 12;

c. the heavy chain variable region comprises CDR-H1 set forth in SEQ ID NO: 13, CDR-H2 set forth in SEQ ID NO: 14, and CDR-H3 set forth in SEQ ID NO: 15; and the light chain variable region comprises CDR-L1 set forth in SEQ ID NO: 16, CDR-L2 set forth in SEQ ID NO: 17, and CDR-L3 set forth in SEQ ID NO: 18;

d. the heavy chain variable region comprises CDR-H1 set forth in SEQ ID NO: 19, CDR-H2 set forth in SEQ ID NO: 20, and CDR-H3 set forth in SEQ ID NO: 21; and the light chain variable region comprises CDR-L1 set forth in SEQ ID NO: 22, CDR-L2 set forth in SEQ ID NO: 23, and CDR-L3 set forth in SEQ ID NO: 24; or e. the heavy chain variable region comprises CDR-H1 set forth in SEQ ID NO: 25, CDR-H2 set forth in SEQ ID NO: 26, and CDR-H3 set forth in SEQ ID NO: 27; and the light chain variable region comprises CDR-L1 set forth in SEQ ID NO: 28, CDR-L2 set forth in SEQ ID NO: 29, and CDR-L3 set forth in SEQ ID NO:30.

8. The single-chain antibody according to claim 7, wherein the heavy chain variable region and the light chain variable region are selected from any one of the following combinations: a) the heavy chain variable region comprises a polypeptide fragment set forth in SEQ ID NO: 31, and the light chain variable region comprises a polypeptide fragment set forth in SEQ ID NO: 32; b) the heavy chain variable region comprises a polypeptide fragment set forth in SEQ ID NO: 33, and the light chain variable region comprises a polypeptide fragment set forth in SEQ ID NO: 34; c) the heavy chain variable region comprises a polypeptide fragment set forth in SEQ ID NO: 35, and the light chain variable region comprises a polypeptide fragment set forth in SEQ ID NO: 36; d) the heavy chain variable region comprises a polypeptide fragment set forth in SEQ ID NO: 37, and the light chain variable region comprises a polypeptide fragment set forth in SEQ ID NO: 38; or e) the heavy chain variable region comprises a polypeptide fragment set forth in SEQ ID NO: 39, and the light chain variable region comprises a polypeptide fragment set forth in SEQ ID NO:40.

9. The single-chain antibody according to claim 7, wherein its amino acid sequence is set forth in any one of SEQ ID NOs: 171-180.

10. A method for treating a digestive tract tumor selected from the group consisting of gastric cancer, colorectal cancer, and esophageal cancer, comprising administering an effective amount of the chimeric antigen receptor according to claim 1 to a subject in need thereof.

11. A method for treating a digestive tract tumor selected from the group consisting of gastric cancer, colorectal cancer, and esophageal cancer, comprising administering an effective amount of the cell according to claim 6 to a subject in need thereof.

12. A method for treating a digestive tract tumor selected from the group consisting of gastric cancer, colorectal cancer, and esophageal cancer, comprising administering an effective amount of the single chain antibody according to claim 7 to a subject in need thereof.

13. The chimeric antigen receptor according to claim 4, wherein the hinge region is encoded by the sequence set forth in SEQ ID NO: 52 or SEQ ID NO: 53, the transmembrane region is encoded by the sequence set forth in SEQ ID NO:54 or SEQ ID NO: 55, the intracellular signaling domain is encoded by the sequence set forth in SEQ ID NO:56 or SEQ ID NO: 57 or SEQ ID NO: 58.

14. The chimeric antigen receptor according to claim 3, wherein the amino acid sequence of the single-chain antibody is set forth in SEQ ID NO: 173 or SEQ ID NO: 178.

15. The single-chain antibody according to claim 9, wherein its amino acid sequence is set forth in SEQ ID NO: 173 or SEQ ID NO: 178.

16. The cell according to claim 6, wherein said cell is a T cell.

* * * * *

UNITED STATES PATENT AND TRADEMARK OFFICE
CERTIFICATE OF CORRECTION

PATENT NO. : 11,266,688 B2
APPLICATION NO. : 16/321529
DATED : March 8, 2022
INVENTOR(S) : Fan et al.

It is certified that error appears in the above-identified patent and that said Letters Patent is hereby corrected as shown below:

In the Specification

In the Sequence Listing section Column 25 in sequence no. 15, on Line 10, please delete "Gly Gly Leu Tyr Tyr Gly Tyr Asp Ile Ala Tyr" and insert --Asp Lys Gly Ile Ala Tyr Tyr Phe Asp Tyr-- therefor.

In the Sequence Listing section Column 25 in sequence no. 16, on Line 23, please delete "Asp Lys Gly Ile Ala Tyr Tyr Phe Asp Tyr" and insert --Arg Ala Ser Ser Ser Val Ser Tyr Ile His-- therefor.

Signed and Sealed this
Twenty-sixth Day of April, 2022

Katherine Kelly Vidal
*Director of the United States Patent and Trademark Office*